United States Patent
Quattropani et al.

(10) Patent No.: US 9,233,982 B2
(45) Date of Patent: Jan. 12, 2016

(54) SPIRO TETRAHYDRO—BENZOTHIOPHEN DERIVATIVES USEFUL FOR THE TREATMENT NEURODEGENERATIVE DISEASES

(71) Applicant: Ares Trading S.A., Aubonne (CH)

(72) Inventors: Anna Quattropani, Rolle (CH); Dominique Swinnen, Braine L'Alleud (BE)

(73) Assignee: Ares Trading S.A., Aubonne (CH)

( * ) Notice: Subject to any disclaimer, the term of this patent is extended or adjusted under 35 U.S.C. 154(b) by 0 days.

(21) Appl. No.: 14/401,959

(22) PCT Filed: May 10, 2013

(86) PCT No.: PCT/EP2013/001389
§ 371 (c)(1),
(2) Date: Nov. 18, 2014

(87) PCT Pub. No.: WO2013/178322
PCT Pub. Date: Dec. 5, 2013

(65) Prior Publication Data
US 2015/0111882 A1  Apr. 23, 2015

Related U.S. Application Data

(60) Provisional application No. 61/655,078, filed on Jun. 4, 2012.

(30) Foreign Application Priority Data

May 31, 2012  (EP) ..................................... 12170227

(51) Int. Cl.
| | | |
|---|---|---|
| C07D 513/10 | (2006.01) | |
| C07D 495/10 | (2006.01) | |
| C07D 498/10 | (2006.01) | |
| A61K 31/547 | (2006.01) | |
| A61K 31/4188 | (2006.01) | |
| A61K 31/4439 | (2006.01) | |
| A61K 31/4245 | (2006.01) | |

(52) U.S. Cl.
CPC .......... *C07D 513/10* (2013.01); *A61K 31/4188* (2013.01); *A61K 31/4245* (2013.01); *A61K 31/4439* (2013.01); *A61K 31/547* (2013.01); *C07D 495/10* (2013.01); *C07D 498/10* (2013.01)

(58) Field of Classification Search
CPC .. C07D 513/10; C07D 495/10; C07D 498/10; A61K 31/547; A61K 31/4188; A61K 31/4439; A61K 31/4245
USPC ........................................... 544/6; 514/222.5
See application file for complete search history.

(56) References Cited

FOREIGN PATENT DOCUMENTS

| WO | 2010013794 A1 | 2/2010 |
|---|---|---|
| WO | 2011106414 A1 | 9/2011 |

OTHER PUBLICATIONS

Greene and Wuts, "Protective Groups in Organic Synthesis", Wiley Interscience, 3rd Edition, 1999.
Hardy, "Has the Amyloid Cascade Hypothesis for Alzheimer's Disease been Proved?", Current Alzheimer Research, 2006, 3: 71-73.
Houben-Weyl, Methoden der organischen Chemie [Methods of Organic Chemistry], Georg-Thieme-Verlag, Stuttgar.
Hussain, "Identification of a Novel Aspartic Protease (Asp 2) as B-Secretase", Mol. Cell Neurosci., 1999, 14(6): 419-427.
Kocienski Philip J., "Protecting Groups", Georg Thieme Verlag Stuttgart, New York, 1994.
Tanzi, "Twenty Years of the Alzheimer's Disease Amyloid Hypothesis: A Genetic Perspective", Cell, 2005, 120: 545-555.
Tyle, "Iontophoretic Devices for Drug Delivery", Pharmaceutical Research, 1986, 3(6): 318-319.
Yoshida, "Study of biodegradable copoly (L-lactic acid/glycolic acid) formulations with controlled release of Z-100 for application in radiation therapy", Int. J. Pharm., 1995, 115: 61-67.

*Primary Examiner* — Kahsay Habte
(74) *Attorney, Agent, or Firm* — Dwight D. Kim; EMD Serono Research and Development Institute

(57) ABSTRACT

The present invention provide compounds of Formula (I) used as BACE inhibitors for the treatment of neurodegenerative diseases.

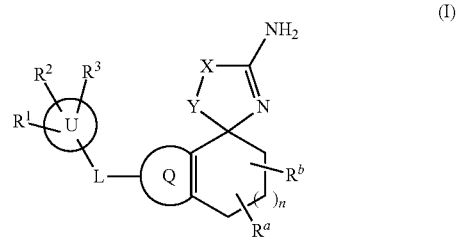

11 Claims, No Drawings

SPIRO TETRAHYDRO—BENZOTHIOPHEN DERIVATIVES USEFUL FOR THE TREATMENT NEURODEGENERATIVE DISEASES

RELATED APPLICATIONS

This application is a U.S. national stage application of PCT international application PCT/EP2013/001389, filed on May 10, 2013, which claims the benefit of U.S. provisional Application No. 61/655,078, filed on Jun. 4, 2012, and EP application EP12170227.8, filed on May 31, 2012. The entire contents of the aforementioned applications are hereby incorporated by reference.

The present invention relates to a spiro tetrahydro-benzothiophen derivatives and pharmaceutical use thereof. More particularly, the present invention relates to compounds which decrease amyloid-β (hereinafter referred to as Aβ) peptide production via inhibition of beta-site amyloid precursor protein cleaving enzyme 1 (hereinafter referred to as BACE-1) and are effective for treating neurodegenerative diseases caused by Aβ protein, in particular, Alzheimer's disease, Down's syndrome or the like, and to a pharmaceutical composition comprising such compound as an active ingredient.

Alzheimer's disease (AD) is a progressive neurodegenerative disorder marked by loss of memory, cognition, and behavioral stability. AD afflicts 6-10% of the population over age 65 and up to 50% over age 85. It is the leading cause of dementia and the third leading cause of death after cardiovascular disease and cancer. At present, there are no effective treatments for AD and treatment is limited to the use of symptomatic agents such as the cholinesterase inhibitor, donepezil (Aricept®, Pfizer). The total net cost related to AD in the U.S. exceeds $100 billion annually.

AD is characterised pathologically by the presence of specific lesions in the limbic and cortical regions of the brain. These include intracellular neurofibrillary tangles consisting of hyperphosphorylated tau protein and the extracellular deposition of fibrillar aggregates of amyloid-beta peptides in the form of amyloid plaques (senile plaques). The major components of amyloid plaques are amyloid-beta (A-beta, Abeta or Aβ) peptides of various lengths (39-42 amino acids). A variant thereof, which is the Aβ1-42 (Abeta1-42, Aβ42) peptide, is believed to be the major pathogenic species in AD brain and can act as a seed for amyloid plaque formation. Another variant is the Aβ1-40 (Abeta1-40, Aβ40) peptide.

The identification of mutations in the beta-Amyloid Precursor Protein (beta-APP, β-APP or APP), Presenilin-1 (PS-1) and Presenilin-2 (PS-2) genes that increase Aβ production and lead to early-onset familial forms of AD have given strong support to the "amyloid cascade hypothesis" of AD (Hardy, 2006 Curr Alzheimer Res. 3(1):71-73; Tanzi and Bertram, 2005 Cell 120, 545) and therapeutic approaches targeting Aβ production. There is emerging data on the role of Aβ peptides in other diseases including, but not limited to Down's syndrome (DS), mild cognitive impairment (MCI), cerebral amyloid angiopathy (CAA), inclusion body myositis (IBM) and age-related macular degeneration. Hence, Aβ lowering agents could be beneficial for the treatment of diverse pathologies in which Aβ peptides are implicated.

Aβ peptides are generated following proteolytic processing of APP. The generation of Aβ peptides is regulated by at least two proteolytic activities referred to as BACE-1 and γ-secretase. APP is initially cleaved by BACE-1 at the N-terminus (Met-Asp bond) of the Aβ domain leading to the secretion of soluble APPβ (sAPPβ) and the retention of a 12 kDa membrane-bound carboxy terminal fragment (CTFβ). The latter is subsequently cleaved by γ-secretase to generate Aβ peptides of varying length and an APP intracellular domain (AICD).

BACE-1 is a type I transmembrane aspartic protease that comprises a large extracellular domain containing the catalytic active site, a single transmembrane domain and a short cytoplasmic tail (Hussain et al. 1999, Mol Cell Neurosci. 14(6): 419-427). Due to its pivotal role in Aβ generation, BACE-1 is an attractive therapeutic target for AD. Already known beta-secretase inhibitors are reported in WO2010/013794.

In one embodiment, the present invention provides compounds of Formula (I)

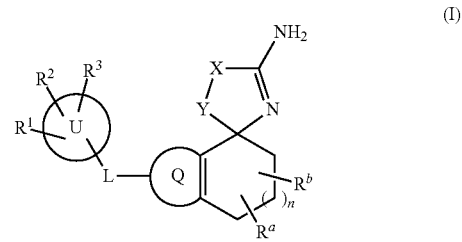

Wherein

X denotes a group selected from —S—$CH_2$—, —SO—$CH_2$—, while Y denotes a —$CH_2$— group, or alternatively X—Y together form a group —$NR^5$—O—, —$NR^5$—CO—, Q denotes a thiophene ring, L denotes a simple bond or a group —$NR^5$—CO—, U denotes a phenyl, pyridine, or pyrimidine group, $R^1$, $R^2$, $R^3$ are independently from one another selected from H, CN, halogen, Ar, Het, A, OA, $SO_2A$, $CO_2A$, $O(CH_2)Ar$, or 2 of $R^1$, $R^2$ and $R^3$ are linked together to form a 5 to 8 membered ring fused to the ring U and optionally containing 1 to 3 heteroatoms independently selected from O, N or S, $R^a$, $R^b$ are independently from one another H, A, Ar, $(CH_2)$Ar, $(CH_2)$Het, $R^5$ is selected from H, A, $(CH_2)$—Ar, A is a linear or branched alkyl having 1 to 6 carbon atoms wherein 1 to 6 hydrogen atoms may be independently replaced by a group selected from halogen, —$OC_1$-$C_6$-alkyl, CN, Ar is a 6-membered aromatic ring, preferably a phenyl, which may be substituted with 1 to 3 groups selected from A, OA, phenyl, pyridine, CN, OH, $CO_2A$, Het is a 4- to 8-membered heterocyclic ring containing 1 to 3 heteroatoms independently selected from O, S, N or CO, and optionally substituted with 1 to 3 groups selected from A, OA, phenyl, pyridine, CN, OH, $CO_2A$, n is 0, 1, 2, preferably 1, as well as enantiomers, diastereoisomers, tautomers thereof in all ratios, and salts thereof.

In another embodiment, the present invention also encompass compounds of Formula (I'), that are tautomers of the compounds of Formula (I)

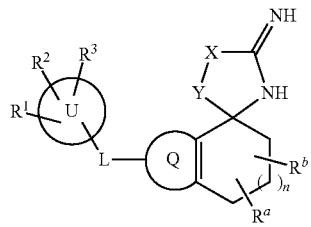
(I')

Wherein $R^1$, $R^2$, $R^3$, $R^a$, $R^b$, U, Q, L X, n and Y are as above defined.

In another embodiment the present invention provides compounds of Formula (Ia), (Ib) and (Ic):

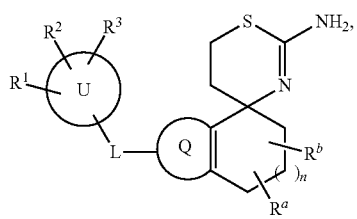
(I-1)

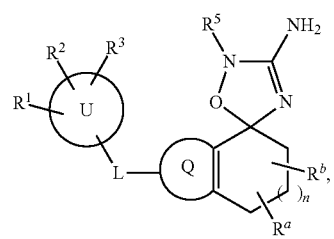
(I-2)

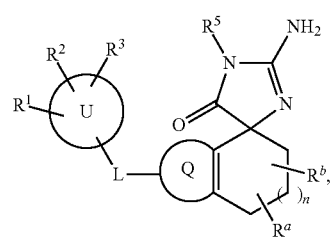
(I-3)

Wherein $R^1$, $R^2$, $R^3$, $R^a$, $R^b$, U, Q, L, X, n and Y are as above defined.

Compounds of Formula (I) and related Formulae also encompass the enantiomers A and B and mixtures of enantiomers A and B in all ratios.

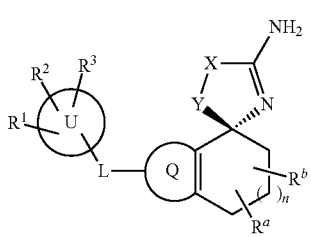
(A)

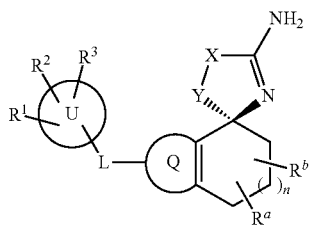
(B)

Wherein $R^1$, $R^2$, $R^3$, $R^a$, $R^b$, U, Q, L, X, n and Y are as above defined.

In another aspect, the present invention provides the use of the compounds of Formula (I) as a medicament. In particular, compounds of Formula (I) are used in the treatment and prophylaxis of neurodegenerative diseases. Examples of neurodegenerative diseases are Alzheimer's disease, Down's syndrome. Additional neurodegenerative symptoms are memory disorders, neuropathic pain.

In another aspect, the present invention provides a kit or a set consisting of separate packs of (a) an effective amount of a compound of Formula (I) according to one or more of claims 1 to 5 and/or pharmaceutically usable derivatives, tautomers, salts, solvates and stereoisomers thereof, including mixtures thereof in all ratios, and (b) an effective amount of a further medicament active ingredient.

In a specific embodiment, the group

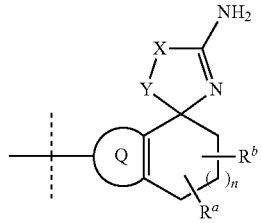

denotes one of the following groups:

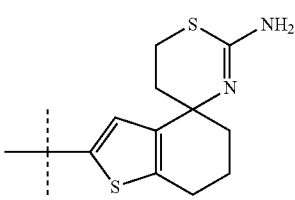

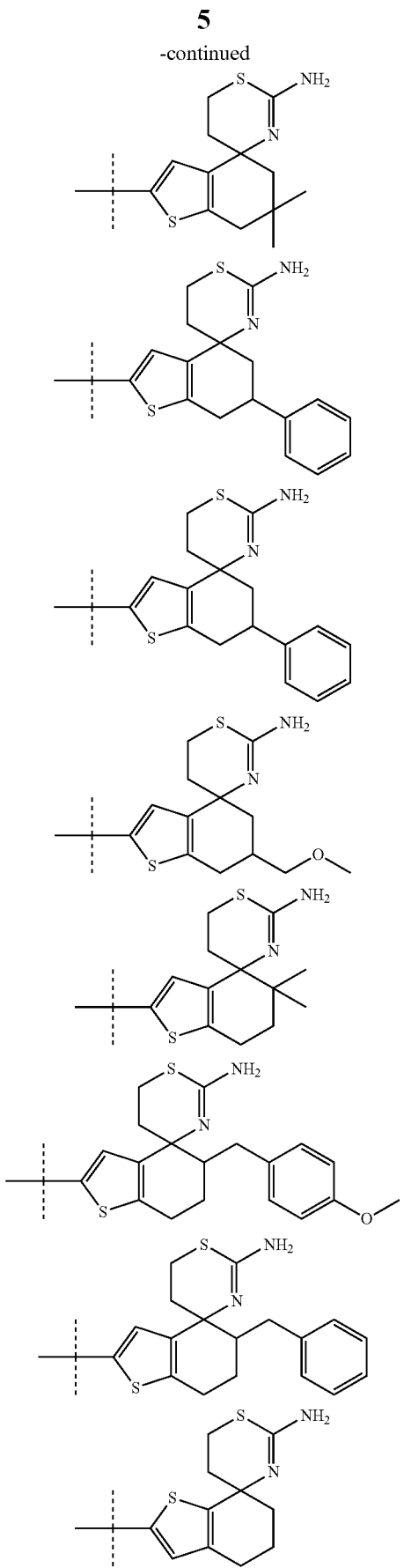
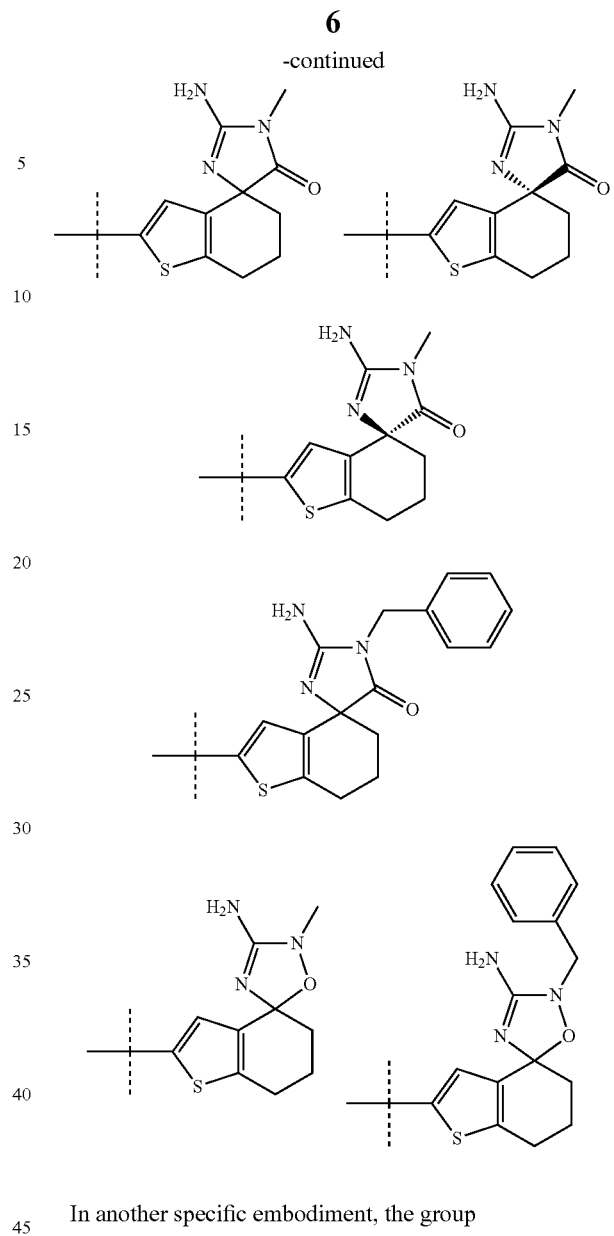
In another specific embodiment, the group
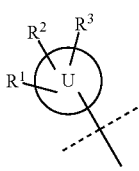
denotes one of the following groups:
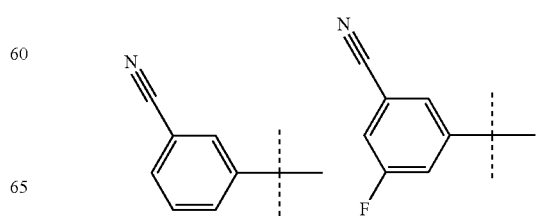

-continued
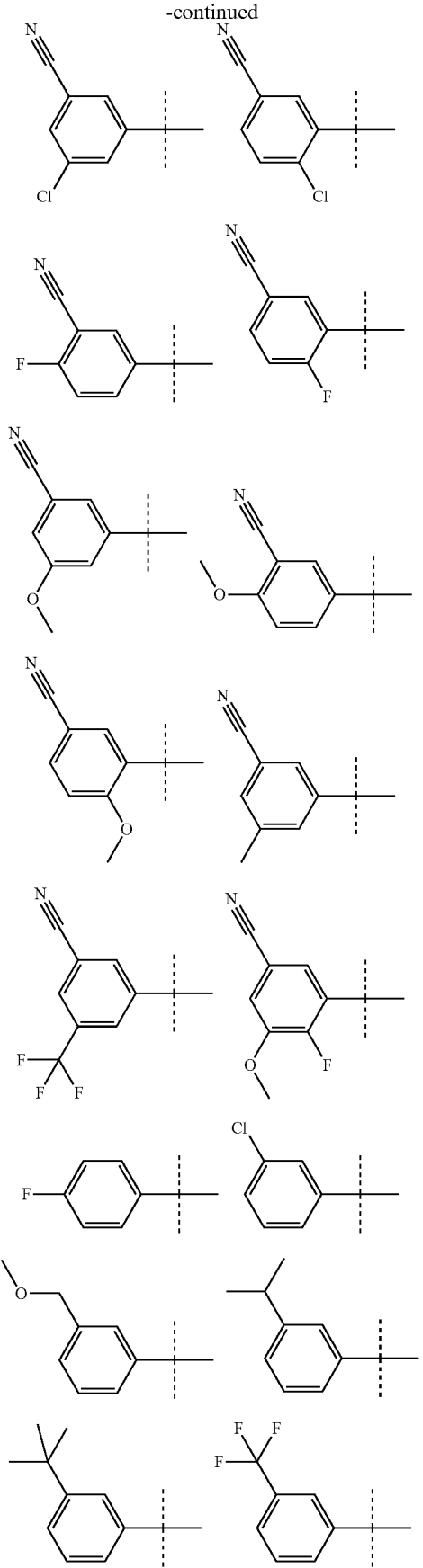
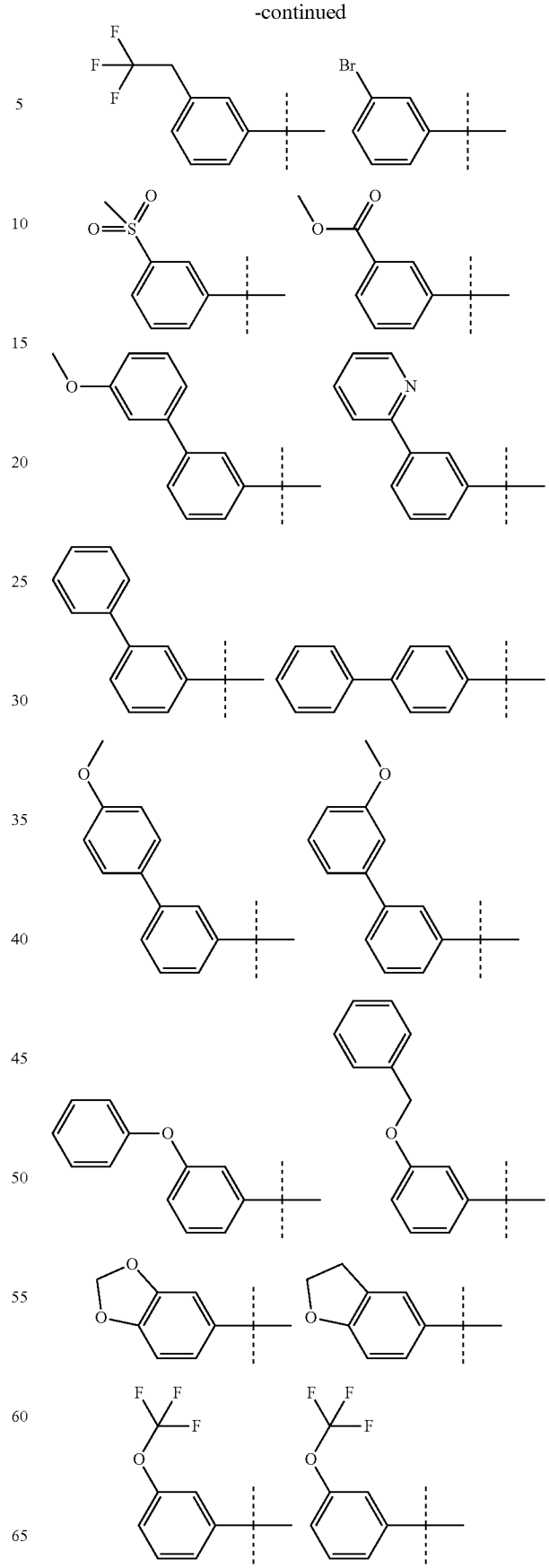

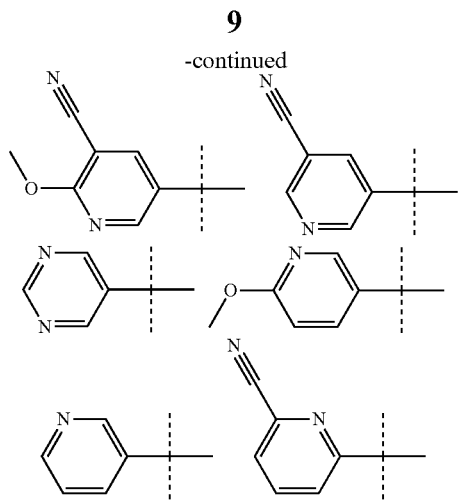
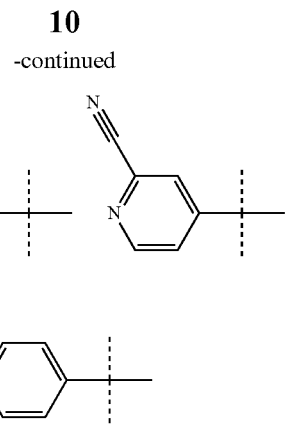
The preferred compounds of the present invention are the following:
| Ex | Compound | Ex | Compound |
|---|---|---|---|
| 1 | | 2 | |
| 3 | | 4 | |
| 5 | | 6 | |
| 7 | | 8 | |
| 9 | | 10 | |

-continued

| Ex | Compound | Ex | Compound |
|---|---|---|---|
| 11 | | 12 | |
| 13 | | 14 | |
| 15 | | 16 | |
| 17 | | 18 | |
| 19 | | 20 | |
| 21 | | 22 | |
| 23 | | 24 | |

| Ex | Compound | Ex | Compound |
|----|----------|----|----------|
| 25 | 3-(trifluoromethyl)phenyl-substituted spiro thiophene thiazine compound | 26 | 3-phenoxyphenyl-substituted spiro thiophene thiazine compound |
| 27 | 3-isopropylphenyl-substituted spiro thiophene thiazine compound | 28 | 3-chlorophenyl-substituted spiro thiophene thiazine compound |
| 29 | 4-biphenyl-substituted spiro thiophene thiazine compound | 30 | 3-(benzyloxy)phenyl-substituted spiro thiophene thiazine compound |
| 31 | 6-cyanopyridin-2-yl-substituted spiro thiophene thiazine compound | 32 | 3-cyano-5-(trifluoromethyl)phenyl-substituted spiro thiophene thiazine compound |
| 33 | 4'-methoxybiphenyl-3-yl-substituted spiro thiophene thiazine compound | 34 | 3-cyano-5-chlorophenyl-substituted spiro thiophene thiazine compound |
| 35 | 3-cyano-5-methylphenyl-substituted spiro thiophene thiazine compound | 36 | 3-(pyridin-2-yl)phenyl-substituted spiro thiophene thiazine compound |

-continued

| Ex | Compound | Ex | Compound |
|---|---|---|---|
| 37 | | 38 | |
| 39 | | 40 | |
| 41 | | 42 | |
| 43 | | 44 | |
| 45 | | 46 | |
| 47 | | 48 | |

-continued

| Ex | Compound | Ex | Compound |
| --- | --- | --- | --- |
| 49 | | 50 | |
| 51 | | 52 | |
| 53 | | 54 | |
| 55 | | 56 | |
| 57 | | 58 | |
| 59 | | 60 | |

| Ex | Compound | Ex | Compound |
|---|---|---|---|
| 61 | | 62 | |

GENERAL DESCRIPTION OF METHODS

The following abbreviations refer respectively to the definitions below:

aq (aqueous), h (hour), g (gram), L (liter), mg (milligram), MHz (Megahertz), μM (micromolar) min. (minute), mm (millimeter), mmol (millimole), mM (millimolar), m.p. (melting point), eq (equivalent), mL (milliliter), μL (microliter), ACN (acetonitrile), BINAP (2,2'-bis(disphenylphosphino)-1,1'-binaphthalene, BOC (tert-butoxy-carbonyl), CBZ (carbobenzoxy), CDCl3 (deuterated chloroform), CD$_3$OD (deuterated methanol), CH$_3$CN (acetonitrile), c-hex (cyclohexane), DCC (dicyclohexyl carbodiimide), DCM (dichloromethane), dppf (1,1'-bis(diphenylphosphino)ferrocene), DIC (diisopropyl carbodiimide), DIEA (diisopropylethyl-amine), DMF (dimethylformamide), DMSO (dimethylsulfoxide), DMSO-d$_6$ (deuterated dimethylsulfoxide), EDC (1-(3-dimethyl-amino-propyl)-3-ethylcarbodiimide), ESI (Electro-spray ionization), EtOAc (Ethyl acetate), Et$_2$O (diethyl ether), EtOH (ethanol), FMOC (fluorenylmethyloxycarbonyl), HATU (dimethylamino-([1,2,3]triazolo[4,5-b]pyridin-3-yloxy)-methylene]-dimethyl-ammonium hexafluorophosphate), HPLC (High Performance Liquid Chromatography), i-PrOH (2-propanol), K$_2$CO$_3$ (potassium carbonate), LC (Liquid Chromatography), MD Autoprep (Mass directed Autoprep), MeOH (methanol), MgSO$_4$ (magnesium sulfate), NMI (N-methyl imidazole), MS (mass spectrometry), MTBE (Methyl tert-butyl ether), Mtr. (4-Methoxy-2,3,6-trimethylbenzensulfonyl), MW (microwave), NBS (N-bromo succinimide), NaHCO$_3$ (sodium bicarbonate), NaBH$_4$ (sodium borohydride), NMM (N-methyl morpholine), NMR (Nuclear Magnetic Resonance), POA (phenoxyacetate), Py (pyridine), PyBOP® (benzotriazole-1-yloxy-tris-pyrrolidino-phosphonium hexafluorophosphate), RT (room temperature), Rt (retention time), SFC (supercritical fluid chromatography), SPE (solid phase extraction), T3P (propylphosphonic anhydride), TBAF (tetra-n-butylammonium fluoride), TBTU (2-(1-H-benzotriazole-1-yl)-1,1,3,3-tetramethyluromium tetrafluoro borate), TEA (triethylamine), TFA (trifluoroacetic acid), THF (tetrahydrofurane), TLC (Thin Layer Chromatography), UV (Ultraviolet).

In general, the compounds according to Formula (I) and related formulae of this invention may be prepared from readily available starting materials. If such starting materials are not commercially available, they may be prepared by standard synthetic techniques. In general, the synthesis pathways for any individual compound of Formula (I) and related formulae will depend on the specific substituents of each molecule, such factors being appreciated by those of ordinary skill in the art. The following general methods and procedures described hereinafter in the examples may be employed to prepare compounds of Formula (I) and related formulae. Reaction conditions depicted in the following schemes, such as temperatures, solvents, or co-reagents, are given as examples only and are not restrictive. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures. For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3$^{rd}$ Edition 1999.

The general method to synthesize a compound of Formula (I) and related Formulae is depicted in Scheme A, starting from ketone derivatives of Formula (II), following methods that are described hereinafter or procedures well known to those skilled in the art.

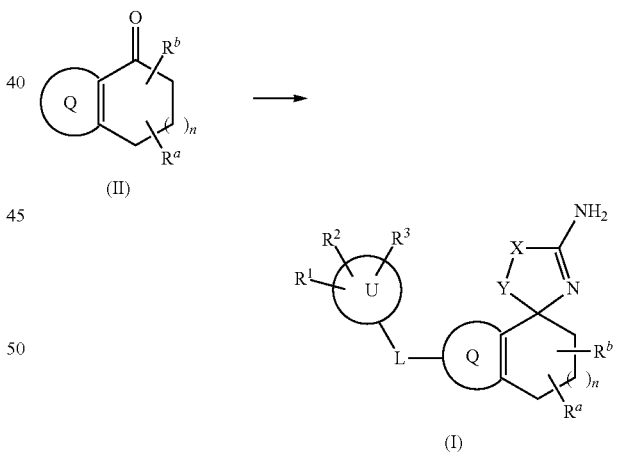

Scheme A

Different synthetic strategies may be selected for the synthesis of compounds of Formula (I). Starting materials can be a suitably substituted thiophene ketone (IIa), where the ring-fused carbocycle attached to the thiophene ring can be different ring sizes. The carbocyclic ring can be substituted alpha or beta to the ketone with a suitable alkyl or aryl group. The ketone can be reacted with a vinyl Grignard reagent, typically in THF at a temperature comprised between about −78° C. and about 0° C., to produce a vinyl carbinol product (III). The vinyl alcohol can be reacted with thiourea in acetic acid at temperatures between about 25° C. and about 40° C. to produce an isothiouronium derivative (IV), which can be further cyclised to the spirocyclic aminothiazine (Ia) wherein $R^a$ and $R^b$ are as above defined. Such cyclisation can be performed for instance in concentrated HCl at about 25° C. In some cases, the spirocyclic aminothiazine (Ia) can be prepared directly from the vinyl alcohol (III) by reaction with thiourea in concentrated HCl. Substitution of the thiophene can be achieved usually after protection of the aminothiazine (Ia) with a protecting group (PG), affording compounds of formula (Va). The protecting group (PG) can be for instance a tert-butyloxycarbonyl group or a benzyloxycarbonyl group. The compound (Va) is transformed in compound (Vb) wherein T is selected from, but not limited to, halogen, nitro, carboxy, boronic acid or boronate ester. Bromination (T=Br), for example, can be achieved with N-bromosuccinimide in dichloromethane, or bromine in a suitable solvent, such as acetic acid or chloroform at temperatures between about 0° C. and about 25° C., yielding compounds of Formula (Vb). The group T can then be substituted with an aromatic or heteroaryl group. Such a substitution can be performed for example by using a suitable aromatic boronic acid or boronate ester with a palladium catalyst in dimethylformamide or dioxan at temperatures between about 80° C. and about 100° C., yielding a compound of Formula (Vc), wherein L is a single bond and wherein U, $R^1$, $R^2$, and $R^3$ are as above defined. Compounds of formula (Ib) are then obtained by removal of PG, using conditions well known to those skilled in the art (Scheme 1).

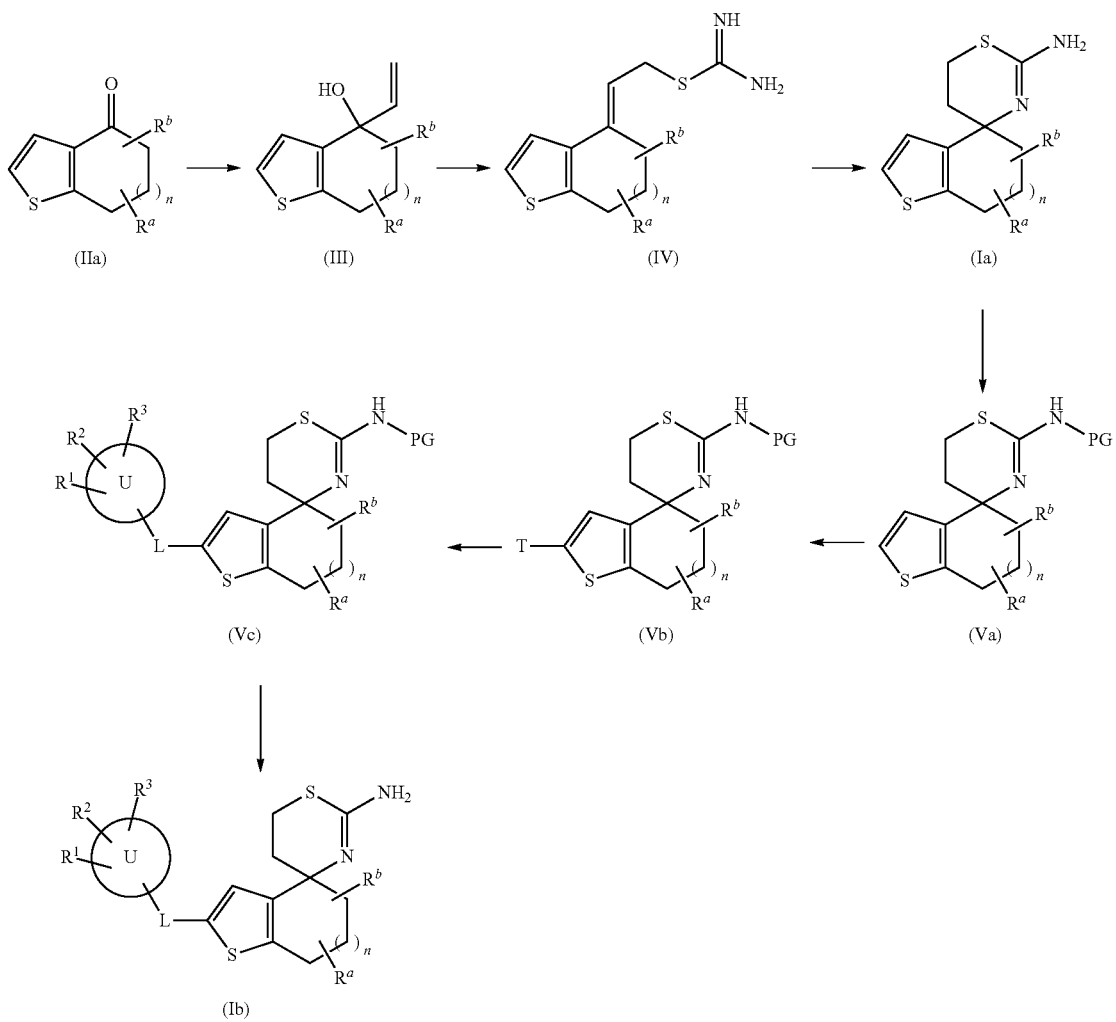

Scheme 1

Alternatively, the halogen derivative (Vb) can be reacted with a boronate ester, such as bis(pinacolato)diboron, to form a thiophene substituted boronate. This reaction can be achieved with a suitable palladium catalyst in a solvent such as DMF at temperatures between about 80° C. and about 100° C. The thiophene substituted boronate can be reacted with an aryl or heteroaryl bromide with a suitable palladium catalyst in a solvent such as DMF at temperatures between about 80° C. and about 100° C., affording compounds of Formula (Vc).

Various other spirocyclic rings other than aminothiazine can be prepared from the ketones of Formula (IIa) described here. For example, aminoimidazolone derivatives can be prepared by reacting a suitable thiophene ketone (IIa) with potassium or sodium cyanide in the presence of ammonium carbonate in a solvent such as aqueous ethanol at about 80° C. (Scheme 2). The hydantoin derivative (VI) obtained, wherein $R^a$ and $R^b$ are as above defined, can be converted into the thiohydantoin derivative (VII). Such a reaction can be performed by example by treating (VI) with Lawesson's reagent in toluene, dioxan or THF with heating. Alkylation on sulfur can be achieved with an alkyl or aryl halide and a base such as sodium hydroxide in a solvent like methanol or ethanol, yielding derivative (VIII). The aminoimidazolone spirocycle of Formula (Ic) can be formed by displacement of the thiomethyl group with ammonia in the presence of ammonium iodide in methanol in a sealed tube at 90° C. Substitution of the thiophene can be achieved with or without protection of the aminoimidazolone group as described for the aminothiazine compounds above, affording compounds of Formula (Id) wherein L, U, $R^1$, $R^2$ and $R^3$ are as defined for scheme 1.

Scheme 3

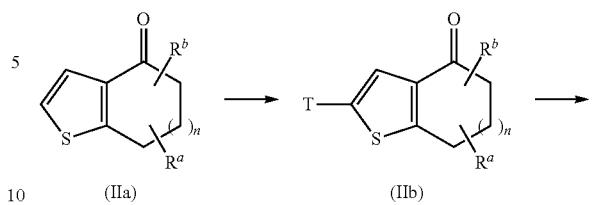

Scheme 2

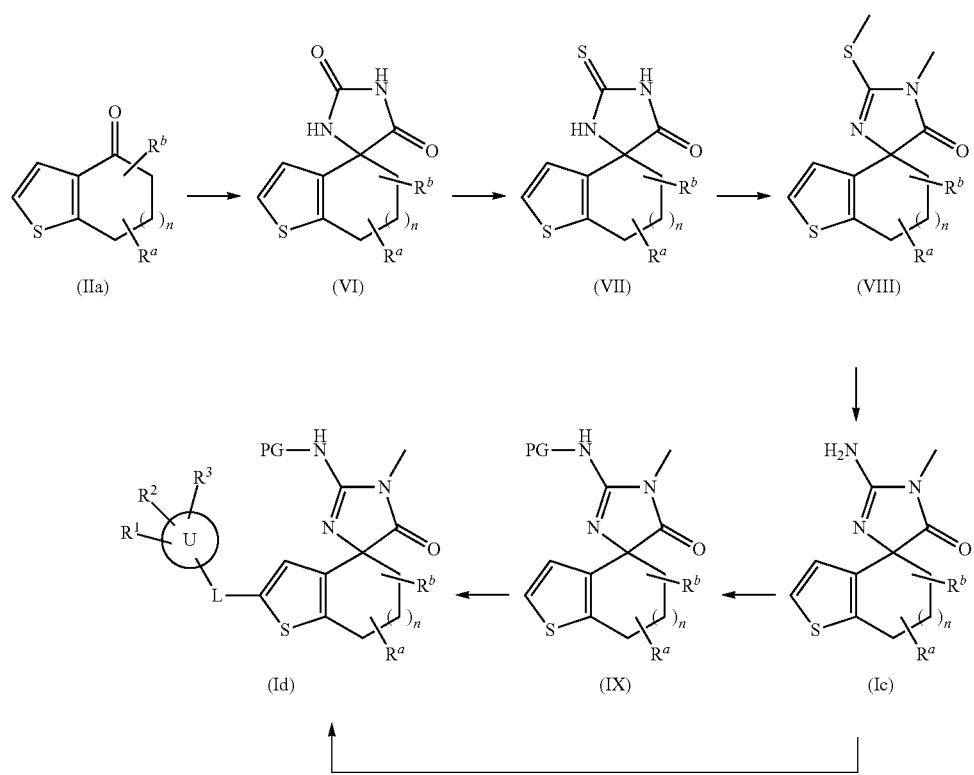

Aminooxazine spirocycles of Formula (Ie) can be prepared from the corresponding thiophene carbocyclic ketones (IIa) (Scheme 3). The compound of Formula (IIa) is transformed in a compound of Formula (IIb) wherein $R^a$ and $R^b$ are as above defined and wherein T is selected from, but not limited to, halogen, nitro, carboxy, boronic acid or boronate ester. Bromination (T=Br), for example, can be achieved with bromine in acetic acid or chloroform at about 0° C. The group T can then be substituted with an aromatic or heteroaryl group using a suitable aromatic boronic acid or boronate ester with a palladium catalyst in dimethylformamide or dioxan at temperatures between about 80° C. and about 100° C., yielding compounds of Formula (IIc) wherein U, L, $R^1$, $R^2$, $R^3$, $R^a$ and $R^b$ are as defined for scheme 1. The N-cyanoimine of Formula (X) can be prepared by the treatment of the compound of Formula (IIc) with bis-trimethylsilylcarbodiimide in the presence of titanium tetrachloride in anhydrous dichloromethane. Reaction of the compound of Formula (X) with various hydroxylamine reagents in methanol or ethanol at about 25° C. affords the spirocyclic aminooxazine derivatives of Formula (Ie).

-continued

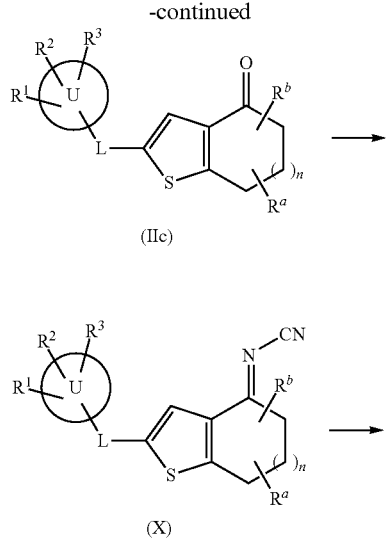

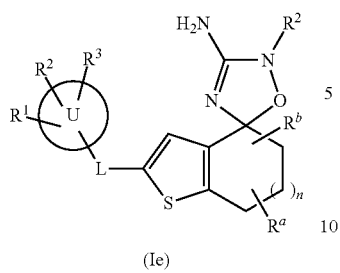

(Ie)

The formation of the spirocyclic rings can take place after the functionalisation of the thiophene ring. For example, a nitro group can be introduced into a suitable ketone (IIa) using concentrated nitric acid in sulphuric acid at temperatures between about 0° C. and about 5° C. (Scheme 4). The nitro group of compound of Formula (IId) can then be reduced to amino using gaseous hydrogen at pressures between 1 and 20 bar, using a suitable catalyst such as palladium or platinum, in a solvent such as ethanol or DMF. The amino group of compound of Formula (IIe) can be reacted with acid chlorides in a solvent such as dichloromethane at about 25° C. with a suitable base such as triethylamine. Alternatively, the amino group can be reacted with carboxylic acids and employing a suitable peptide coupling agent, such as (2-(7-Aza-1H-benzotriazole-1-yl)-1,1,3,3-tetramethyluronium hexafluorophosphate) in a solvent such as DMF at about 25° C., yielding compounds of Formula (IIf) wherein L denotes —NR$^5$—CO— and wherein U, R$^1$, R$^2$ and R$^3$ are as above defined.

Scheme 4

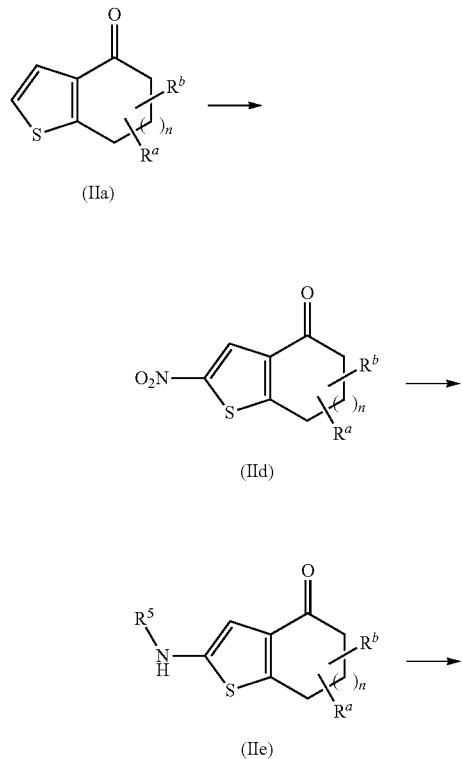

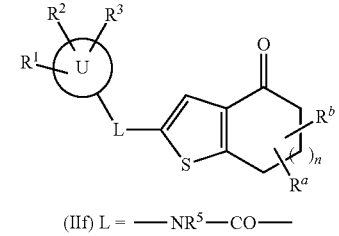

(IIf) L = —NR$^5$—CO—

A compound of Formula (IIg) can be manufactured by reacting a 1,3-dione of Formula (XI), wherein R$^a$ and R$^b$ are as above defined, with a suitably aryl substituted bromo acetophenone in a solvent such as chloroform with a base such as potassium carbonate at about 25° C. (Scheme 5). The 1,3-dione of Formula (XI) can be for example but not limited to dimedone. Ring closure of the triketone to the thiophene derivative can be achieved with Lawesson's reagent in toluene or THF at about 80° C. to about 100° C., yielding compound of Formula (IIg) wherein U, R$^1$, R$^2$, R$^3$, R$^a$ and R$^b$ are as above defined.

Scheme 5

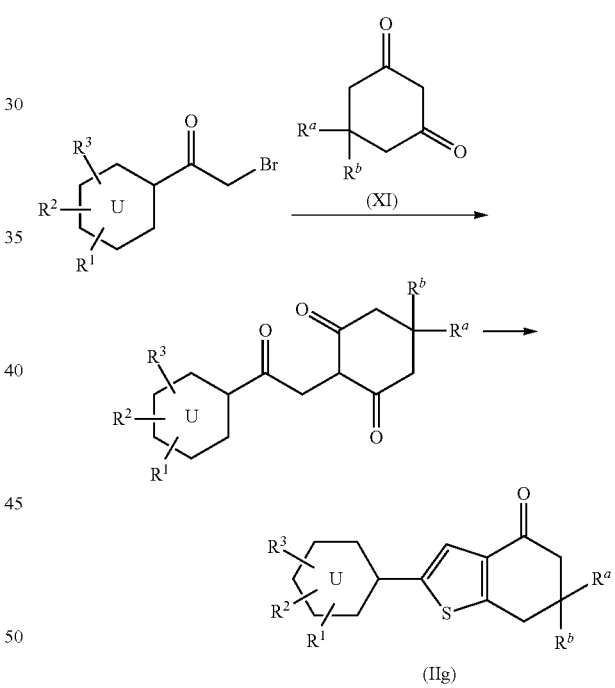

(IIg)

Alternatively, substitution beta to the ketone can be achieved by reacting a suitable thiophene ketone of Formula (IIh), (IIh') or (IIh") wherein the group W is an ester, aldehyde or alcohol. Such starting materials are either commercially available or synthesized following conditions well known to those skilled in the art. Such compounds can be manipulated to provide appropriate substitution at the beta position. For example, 4-Oxo-4,5,6,7-tetrahydro-benzo[b]thiophene-6-carboxylic acid ethyl ester (IIh) wherein the alkyl is ethyl, can be reduced to the corresponding diol of Formula (IIh''') with lithium aluminium hydride or diborane in a solvent such as THF or diethyl ether (Scheme 6). Oxidation of the benzylic alcohol to the ketone (IIh") can be accomplished with manganese dioxide in dichloromethane or dioxan at about 25° C.

Functionalisation of the alcohol group, for example etherification, can be achieved with an alkyl halide and a suitable base such as sodium hydride in a solvent such as THF or DMF at about 0° C., affording ketone of formula (IIi). Mesylation of the alcohol with methane sulfonic anhydride in DCM with a suitable base such as triethylamine allows displacement with a range of nucleophiles Nu, such as amines, alkoxides and organometallic reagents, yielding compounds of Formula (IIj).

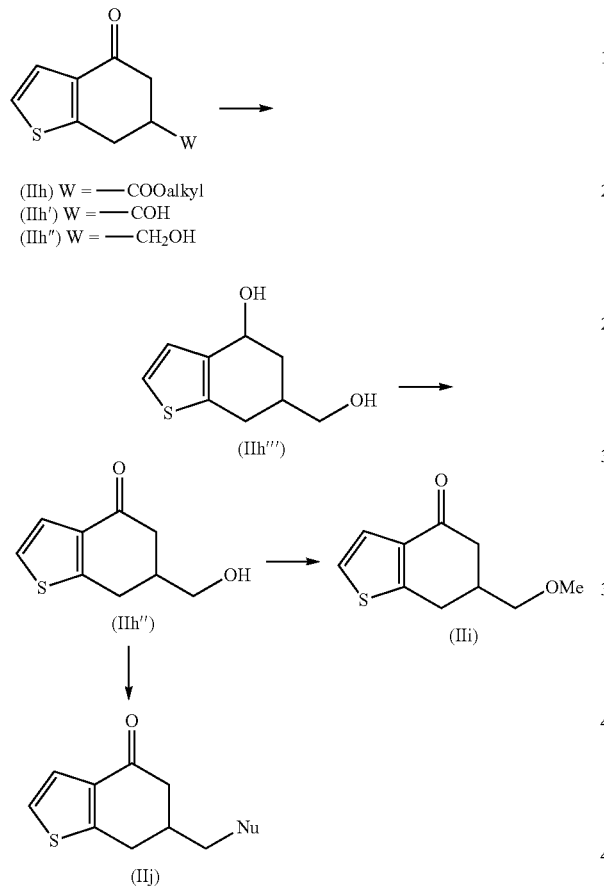

Substitution alpha to the ketone (IIa*) can be achieved by reacting a suitable thiophene ketone with a base such as sodium hydride in DMF or LDA in THF and quenching the resultant enolate with an alkyl halide (Scheme 7). Mono and disubstituted ketones of Formula (IIk) and (IIm) respectively can be achieved with the appropriate quantities of base and electrophile.

Compounds of this invention can be isolated in association with solvent molecules by crystallization from evaporation of an appropriate solvent. The pharmaceutically acceptable acid addition salts of the compounds of formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compounds of formula (I), which contain an acid center, with a suitable base. Both types of salts may be formed or interconverted using ion-exchange resin techniques.

Depending on the conditions used, the reaction times are generally between a few minutes and 14 days, and the reaction temperature is between about −30° C. and 140° C., normally between −10° C. and 90° C., in particular between about 0° C. and about 70° C.

Compounds of the formula (I) can furthermore be obtained by liberating compounds of the formula (I) from one of their functional derivatives by treatment with a solvolysing or hydrogenolysing agent.

Preferred starting materials for the solvolysis or hydrogenolysis are those which conform to the formula (I), but contain corresponding protected amino and/or hydroxyl groups instead of one or more free amino and/or hydroxyl groups, preferably those which carry an amino-protecting group instead of an H atom bound to an N atom, in particular those which carry an R'—N group, in which R' denotes an amino-protecting group, instead of an HN group, and/or those which carry a hydroxyl-protecting group instead of the H atom of a hydroxyl group, for example those which conform to the formula (I), but carry a —COOR" group, in which R" denotes a hydroxyl protecting group, instead of a —COOH group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from

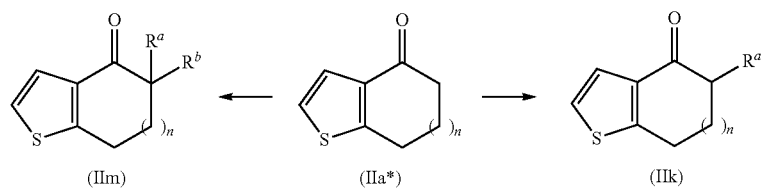

aliphatic, araliphatic, aromatic or heterocyclic carboxylic acids or sulfonic acids, and, in particular, alkoxy-carbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxy-carbonyl, ethoxycarbonyl, 2,2,2-trichloroethoxycarbonyl, BOC (tert-butoxy-carbonyl) and 2-iodoethoxycarbonyl; aralkoxycarbonyl, such as CBZ ("carbo-benz-oxy"), 4-methoxybenzyloxycarbonyl and FMOC; and aryl-sulfonyl, such as Mtr. Preferred aminoprotecting groups are BOC and Mtr, furthermore CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, benzyl, 4-methoxybenzyl, p-nitro-benzoyl, p-toluenesulfonyl, tert-butyl and acetyl, where benzyl and tert-butyl are particularly preferred.

The term "solvates of the compounds" is taken to mean adductions of inert solvent molecules onto the compounds which form owing to their mutual attractive force. Solvates are, for example, mono- or dihydrates or alcoholates.

The compounds of the formula (I) are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as THF or dioxane, amides, such as DMF, halogenated hydrocarbons, such as DCM, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50° C., preferably between 15 and 30° C. (RT).

The BOC, OBut and Mtr groups can, for example, preferably be cleaved off using TFA in DCM or using approximately 3 to 5N HCl in dioxane at 15-30° C., and the FMOC group can be cleaved off using an approximately 5 to 50% solution of dimethylamine, diethylamine or piperidine in DMF at 15-30° C.

Protecting groups which can be removed hydrogenolytically (for example CBZ, benzyl or the liberation of the amidino group from the oxadiazole derivative thereof) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° C. and pressures between about 1 and 200 bar, preferably at 20-30° C. and 1-10 bar. Hydrogenolysis of the CBZ group succeeds well, for example, on 5 to 10% Pd/C in methanol or using ammonium formate (instead of hydrogen) on Pd/C in methanol/DMF at 20-30° C.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, tri-fluoro-methylbenzene, chloroform or DCM; alcohols, such as methanol, ethanol, isopropanol, n-propanol, n-butanol or tert-butanol; ethers, such as diethyl ether, diisopropyl ether, tetrahydrofurane (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, N-methylpyrrolidone (NMP) or dimethyl-formamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as EtOAc, or mixtures of the said solvents.

Esters can be saponified, for example, using LiOH, NaOH or KOH in water, water/THF, water/THF/ethanol or water/dioxane, at temperatures between 0 and 100° C. Furthermore, ester can be hydrolysed, for example, using acetic acid, TFA or HCL.

Free amino groups can furthermore be acylated in a conventional manner using an acyl chloride or anhydride or alkylated using an unsubstituted or substituted alkyl halide or reacted with CH3-C(=NH)—OEt, advantageously in an inert solvent, such as DCM or THF and/or in the presence of a base, such as triethylamine or pyridine, at temperatures between −60° C. and +30° C.

Throughout the specification, the term leaving group preferably denotes Cl, Br, I or a reactively modified OH group, such as, for example, an activated ester, an imidazolide or alkylsulfonyloxy having 1 6 carbon atoms (preferably methylsulfonyloxy or trifluoromethylsulfonyloxy) or arylsulfonyloxy having 6 10 carbon atoms (preferably phenyl- or p tolylsulfonyloxy).

Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart).

Activated esters are advantageously formed in situ, for example through addition of HOBt or N hydroxysuccinimide.

The term "pharmaceutically usable derivatives" is taken to mean, for example, the salts of the compounds of the formula I and so-called prodrug compounds.

The term "prodrug derivatives" is taken to mean compounds of the formula I which have been modified with, for example, alkyl or acyl groups, sugars or oligopeptides and which are rapidly cleaved in the organism to form the active compounds.

These also include biodegradable polymer derivatives of the compounds according to the invention, as described, for example, in Int. J. Pharm. 115, 61-67 (1995).

Pharmaceutical Salts and Other Forms

The said compounds of the formula (I) can be used in their final non-salt form. On the other hand, the present invention also relates to the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains an acidic center, such as a carboxyl group, one of its suitable salts can be formed by reacting the compound with a suitable base to give the corresponding base-addition salt. Such bases are, for example, alkali metal hydroxides, including potassium hydroxide and sodium hydroxide; alkaline earth metal hydroxides, such as magnesium hydroxide and calcium hydroxide; and various organic bases, such as piperidine, diethanolamine and N-methyl-glucamine (meglumine), benzathine, choline, diethanolamine, ethylenediamine, benethamine, diethylamine, piperazine, lysine, L-arginine, ammonia, triethanolamine, betaine, ethanolamine, morpholine and tromethamine. In the case of certain compounds of the formula I, which contain a basic center, acid-addition salts can be formed by treating these compounds with pharmaceutically acceptable organic and inorganic acids, for example hydrogen halides, such as hydrogen chloride or hydrogen bromide, other mineral acids and corresponding salts thereof, such as sulfate, nitrate or phosphate and the like, and alkyl- and monoaryl-sulfonates, such as methanesulfonate, ethanesulfonate, toluenesulfonate and benzene-sulfonate, and other organic acids and corresponding salts thereof, such as carbonate, acetate, trifluoro-acetate, tartrate, maleate, succinate, citrate, benzoate, salicylate, ascorbate and the like. Accordingly, pharmaceutically acceptable acid-addition salts of the compounds of the formula I include the following: acetate, adipate, alginate, aspartate, benzoate, benzene-sulfonate (besylate), bisulfate, bisulfite, bromide, camphorate, camphor-sulfonate, caprate, caprylate, chloride, chlorobenzoate, citrate, cyclamate, cinnamate, digluconate, dihydrogen-phosphate, dinitrobenzoate, dodecyl-sulfate, ethanesulfonate, formate, glycolate, fumarate, galacterate (from mucic acid), galacturonate, glucoheptanoate, gluconate, glutamate, glycerophosphate, hemi-succinate, hemisulfate, heptanoate, hexanoate, hippurate, hydrochloride, hydrobromide, hydroiodide, 2-hydroxy-ethanesulfonate, iodide, isethionate, isobutyrate, lactate, lactobionate, malate, maleate, malonate, mandelate, metaphosphate, methanesulfonate, methylbenzoate, mono-hydrogen-phosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction. Both types of salts may be formed or interconverted preferably using ion-exchange resin techniques.

Furthermore, the base salts of the compounds of the formula I include aluminium, ammonium, calcium, copper, iron (III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzyl-ethylenediamine (benzathine), dicyclohexylamine, diethanol-amine, diethylamine, 2-diethyl-amino-ethanol, 2-dimethyl-amino-ethanol, ethanolamine, ethylenediamine, N-ethylmorpholine, N-ethyl-piperidine, glucamine, glucosamine, histidine, hydrabamine, isopropyl-amine, lidocaine, lysine, meglumine (N-methyl-D-glucamine), morpholine, piperazine, piperidine, polyamine resins, procaine, purines, theobromine, tri- ethanol-amine, triethylamine, trimethylamine, tripropylamine and tris(hydroxy-methyl)-methylamine (tromethamine), but this is not intended to represent a restriction.

Compounds of the formula I of the present invention which contain basic N2-containing groups can be quaternised using agents such as (C1-C4)-alkyl halides, for example methyl, ethyl, isopropyl and tert-butyl chloride, bromide and iodide; di(C1-C4)alkyl sulfates, for example dimethyl, diethyl and diamyl sulfate; (C10-C18)alkyl halides, for example decyl, do-decyl, lauryl, myristyl and stearyl chloride, bromide and iodide; and aryl-(C1-C4)alkyl halides, for example benzyl chloride and phenethyl bromide. Both water- and oil-soluble compounds of the formula I can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tro-meth-amine, but this is not intended to represent a restriction.

The acid-addition salts of basic compounds of the formula (I) are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts other-wise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanol-amine, ethylenediamine, N-methyl-D-glucamine and procaine.

The base-addition salts of acidic compounds of the formula I are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts other-wise correspond to the respective free acid forms thereof.

If a compound of the formula (I) contains more than one group which is capable of forming pharmaceutically acceptable salts of this type, the formula I also encompasses multiple salts. Typical multiple salt forms include, for example, bitartrate, diacetate, difumarate, dimeglumine, di-phosphate, disodium and trihydrochloride, but this is not intended to represent a restriction.

With regard to that stated above, it can be seen that the term "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Owing to their molecular structure, the compounds of the formula (I) can be chiral and can accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the Intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the (R) and (S) forms of tartaric acid, diacetyltartaric acid, dibenzoyltartaric acid, mandelic acid, malic acid, lactic acid, suitable N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

The invention furthermore relates to the use of compounds of formula I, and related formulae in combination with at least one further medicament active ingredient, preferably medicaments used in the treatment of multiple sclerosis such as cladribine or another co-agent, such as interferon, e.g. pegylated or non-pegylated interferons, preferably interferon beta and/or with compounds improving vascular function or in combination with immunomodulating agents for example Fingolimod; cyclosporins, rapamycins or ascomycins, or their immunosuppressive analogs, e.g. cyclosporin A, cyclosporin G, FK-506, ABT-281, ASM981, rapamycin, 40-O-(2-hydroxy)ethyl-rapamycin etc.; corticosteroids; cyclophosphamide; azathioprene; methotrexate; leflunomide; mizoribine; mycophenolic add; mycophenolate mofetil; 15-deoxyspergualine; diflucortolone valerate; difluprednate; Alclometasone dipropionate; amcinonide; amsacrine; asparaginase; azathioprine; basiliximab; beclometasone dipropionate; betamethasone; betamethasone acetate; betamethasone dipropionate; betamethasone phosphate sodique; betamethasone valerate; budesonide; captopril; chlormethine chlorhydrate; cladribine; clobetasol propionate; cortisone acetate; cortivazol; cyclophosphamide; cytarabine; daclizumab; dactinomycine; desonide; desoximetasone; dexamethasone; dexamethasone acetate; dexamethasone isonicotinate; dexamethasone metasulfobenzoate sodique; dexamethasone phosphate; dexamethasone tebutate; dichlorisone acetate; doxorubicine chlorhydrate; epirubicine chlorhydrate; fluclorolone acetonide; fludrocortisone acetate; fludroxycortide; flumetasone pivalate; flunisolide; fluocinolone acetonide; fluocinonide; fluocortolone; fluocortolone hexanoate; fluocortolone pivalate; fluorometholone; fluprednidene acetate; fluticasone propionate; gemcitabine chlorhydrate; halcinonide; hydrocortisone; hydrocortisone acetate, hydrocortisone butyrate, hydrocortisone hemisuccinate; melphalan; meprednisone; mercaptopurine; methylprednisolone; methylprednisolone acetate; methylprednisolone hemisuccinate; misoprostol; muromonabcd3; mycophenolate mofetil; paramethasone acetate; prednazoline, prednisolone; prednisolone acetate; prednisolone caproate; prednisolone metasulfobenzoate sodique; prednisolone phosphate sodique; prednisone; prednylidene; rifampicine; rifampicine sodique; tacrolimus; teriflunomide; thalidomide; thiotepa; tixocortol pivalate; triamcinolone; triamcinolone acetonide hemisuccinate; triamcinolone benetonide; triamcinolone diacetate; triamcinolone hexacetonide; immunosuppressive monoclonal antibodies, e.g., monoclonal antibodies to leukocyte receptors, e.g., MHC, CD2, CD3, CD4, CD7, CD25, CD28, B7, CD40, CD45 or CD58 or their ligands; or other immunomodulatory compounds, e.g. CTLA4Ig, or other adhesion molecule inhibitors, e.g. mAbs or low molecular weight inhibitors including Selectin antagonists and VLA-4 antagonists. A preferred composition is with Cyclosporin A, FK506, rapamycin or 40-(2-hydroxy)ethyl-rapamycin and Fingolimod. These further medicaments, such as interferon beta, may be administered concomitantly or sequentially, e.g. by subcutaneous, intramuscular or oral routes.

These compositions can be used as medicaments in human and veterinary medicine.

Pharmaceutical formulations can be administered in the form of dosage units, which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process, which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinyl-pyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The active ingredients can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compounds. Syrups can be prepared by dissolving the compounds in an aqueous solution with a suitable flavour, while elixirs are prepared using a non-toxic alcoholic vehicle. Suspensions can be formulated by dispersion of the compounds in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula (I) and salts, solvates and physiologically functional derivatives thereof and the other active ingredients can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula (I) and the salts, solvates and physiologically functional derivatives thereof and the other active ingredients can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropyl-methacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, poly-orthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I and of the other active ingredient depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se.

The present invention furthermore relates to a method for treating a subject suffering from a sphingosine 1-phosphate associated disorder, comprising administering to said subject an effective amount of a compounds of formula (I). The present invention preferably relates to a method, wherein the sphingosine 1-phosphate-1 associated disorder is an autoimmune disorder or condition associated with an overactive immune response.

LIST OF ANALYTICAL METHODS

All NMRs were obtained at 400 MHz on a Bruker instrument.

Names were generated using the Cambridgesoft Chemistry Cartridge (v. 9.0.0.182) software.

All reactions involving air- or moisture-sensitive reagents were performed under a nitrogen atmosphere using dried solvents and glassware.

HPLC conditions were as follows:

Method A: Column: —Supelco, Ascentis® Express C18 or Hichrom Halo C18, 2.7 μm C18, 150×4.6 mm with a gradient of ACN/water/0.1% formic acid (4% to 100% over 6 min with a flow rate of 1 mL/min)

Method B: Column: Column: —Phenomenex Luna 5 μm C18 (2), 100×4.6 mm with a gradient of ACN/water/0.1% formic acid (5% to 95% over 3.5 min with a flow rate of 2 mL/min)

Method C: Column: —Phenomenex, Gemini NX, 3 μm C18, 150×4.6 mm with a gradient of ACN/10 mM Ammonium Bicarbonate in water (4% to 100% over 6 min with a flow rate of 1 mL/min)

Method D: Column: —Waters Xterra MS 5 μm C18, 100×4.6 mm with a gradient of ACN/aqueous 10 mM ammonium bicarbonate (5% to 95% over 3.5 min with a flow rate of 2 mL/min)

Method E: Column: Column: —Phenomenex Luna 5 μm C18 (2), 100×4.6 mm with a gradient of ACN/water/0.1% formic acid (5% to 95% over 4 min with a continuation of ACN at this concentration for a further 4 min; flow rate of 2 mL/min)

Method F: Column: —Waters Xterra MS 5 μm C18, 100×4.6 mm with a gradient of ACN/aqueous 10 mM ammonium bicarbonate (5% to 95% over 3.5 min with a continuation of ACN at this concentration for a further 4 min, flow rate of 2 mL/min).

Chiral Purification

Chiral purification was carried out using either:
1. Chiralpak IA column (25 cm×4.6 mm) eluting with a solvent of heptane (80%) and 1:1 IPA/MeOH/0.1% DEA (20%) at a flow rate of 1.5 mL/min.
2. Chiralpak IB column (25 cm×4.6 mm) eluting with a solvent of heptane (75%) and ethanol (25%) at a flow rate of 1.5 mL/min.

Analytical methods A-F are referred to in the tables of data outlined in the document below.

Example 1

3-(2'-amino-5',6,6',7-tetrahydro-5H-spiro[benzo[b]thiophene-4,4'-[1,3]thiazine]-2-yl)benzonitrile, Formate Salt Method 1

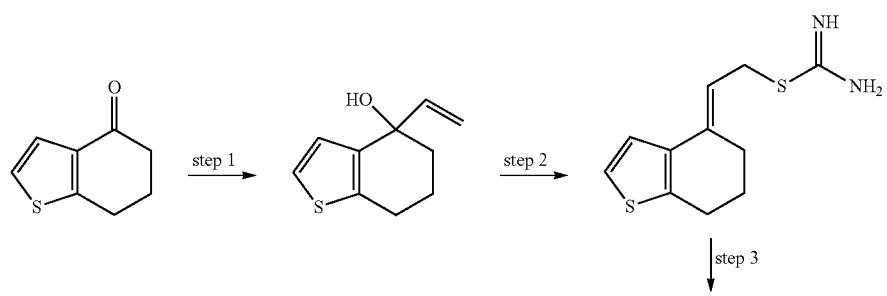

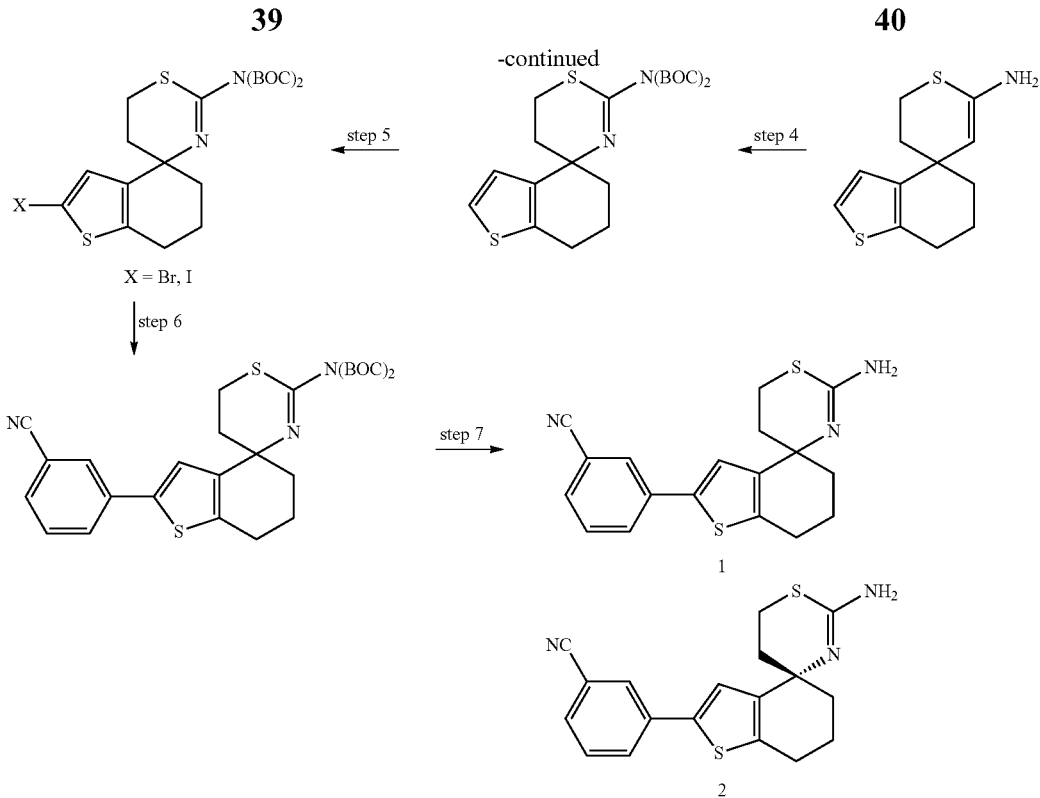

Step 1: 4-vinyl-4,5,6,7-tetrahydrobenzo[b]thiophen-4-ol 6,7-Dihydrobenzo[b]thiophen-4(5H)-one (8.48 g, 56 mmol) was dissolved in anhydrous diethyl ether (200 mL) and the solution was cooled to −30° C. Vinyl magnesium chloride (60 mL, 1.6 M solution in THF, 96 mmol) was added to the ketone portion-wise whilst maintaining the temperature at −30° C. Upon completion of the addition, the reaction was stirred at −30° C. for 30 min and then allowed to warm to 25° C. Stirring was continued overnight and the solution was then treated with saturated ammonium chloride solution. The product was extracted into dichloromethane and this was back extracted with water and saturated brine. The dichloromethane solution was dried (MgSO$_4$), filtered and concentrated in vacuo to afford the title compound as a crude, yellow oil (10.1 g, 100%). This compound was used directly in the next step without further purification.

Step 2: 2-(6,7-dihydrobenzo[b]thiophen-4(5H)-ylidene)ethyl carbamimidothioate 4-Vinyl-4,5,6,7-tetrahydrobenzo[b]thiophen-4-ol (10.1 g, 56 mmol) was dissolved in acetic acid (70 mL) and thiourea (4.3 g, 56 mmol) was added in one portion. The reaction was stirred at 25° C. for 2 hours and then the majority of the acetic acid was removed in vacuo. The residue was diluted with diethyl ether to afford a white solid. This was filtered off and washed with additional ether before being dried in vacuo. The title compound was isolated as the acetate salt (13.8 g, 83%).

Step 3: 5',6',7-tetrahydro-5H-spiro[benzo[b]thiophene-4,4'-[1,3]thiazin]-2'-amine 2-(6,7-Dihydrobenzo[b]thiophen-4(5H)-ylidene)ethyl carbamimidothioate (13.8 g, 46 mmol) was suspended in concentrated HCl (150 mL) and stirred at 25° C. until all the solid dissolved. The reaction was monitored by LC/MS until no more starting material remained. The mixture was then neutralised with aqueous 2 M NaOH solution and ice whereupon a solid precipitated out. This was filtered off, washed with water and dried in vacuo to yield the title compound as a white solid (10.35 g, 93%). $^1$H NMR δ (ppm)(CHCl$_3$-d): 7.05 (1H, d, J=5.25 Hz), 6.88 (1H, d, J=5.24 Hz), 4.79 (2H, s), 3.20-3.01 (2H, m), 2.90-2.74 (2H, m), 2.10-1.98 (2H, m), 1.96-1.77 (4H, m). LCMS (Method f) Rt 2.83 (min) m/z 239 (MH$^+$).

Step 4: di-tert-butyl-5',6,6',7-tetrahydro-5H-spiro[benzo[b]thiophene-4,4'-[1,3]thiazine]-2'-ylcarbamate 5',6,6',7-Tetrahydro-5H-spiro[benzo[b]thiophene-4,4'-[1,3]thiazin]-2'-amine (13.1 g, 55 mmol) was dissolved in dichloromethane (300 mL) and di-tert-butyl dicarbonate (48 g, 220 mmol) and dimethylaminopyridine (13.4 g, 110 mmol) were added. The reaction was stirred at 25° C. overnight and it was then concentrated in vacuo. The residue was taken up in diethyl ether and the resultant solid was removed by filtration. The filtrate was evaporated to a crude residue that was purified on silica gel using 40-60 petroleum ether:ethyl acetate (3:1) to yield the title compound as a yellow oil (21.6 g, 89%).

Step 5: Bromination or Iodination di-tert-butyl 2-bromo-5',6,6',7-tetrahydro-5H-spiro[benzo[b]thiophene-4,4'-[1,3]thiazine]-2'-yliminodicarbonate Di-tert-butyl-5',6,6',7-tetrahydro-5H-spiro[benzo[b]thiophene-4,4'-[1,3]thiazine]-2'-ylcarbamate (6.0 g, 13.7 mmol) was dissolved in dichloromethane (130 mL) and cooled to −5° C. N-Bromosuccinimide (2.56 g, 14.4 mmol) was added in one portion and the reaction was stirred for 1 hr followed by a further 1 hr at 25° C. The dichloromethane solution was then washed with water, dried (MgSO$_4$), filtered and concentrated in vacuo. The crude residue was then purified on silica gel using a gradient elution of 0-50% ethyl acetate in 40-60 petroleum ether, affording the title compound (4.02 g, 57%). $^1$H NMR δ (ppm)(CDCl$_3$): 6.79 (1H, s), 3.28-3.17 (1H, m), 3.12-3.04 (1H, m), 2.80-2.68 (2H, m), 2.09-1.86 (6H, m), 1.52 (18H, s). LCMS (Method d) Rt 4.47 (min) m/z 539 (MH$^+$).

di-tert-butyl 2-iodo-5',6',7-tetrahydro-5H-spiro[benzo[b]thiophene-4,4'-[1,3]thiazine]-2'-ylcarbamate Di-tert-butyl-5',6',7-tetrahydro-5H-spiro[benzo[b]thiophene-4,4'-[1,3]thiazine]-2'-ylcarbamate (2.55 g, 5.8 mmol) was dissolved in dichloromethane (60 mL) and cooled to 0° C. N-Iodosuccinimide (1.38 g, 6.11 mmol) was added in one portion and the reaction was warmed to room temperature and stirred for 1 hr. A further portion of N-iodosuccinimide (1.38 g, 6.11 mmol) was added and the mixture was stirred for a further 18 hr at room temperature. The dichloromethane solution was then washed with water, dried (MgSO$_4$), filtered and concentrated in vacuo. The crude residue was purified on silica gel using a gradient elution of 0-50% ethyl acetate in 40-60 petroleum ether (2.46 g, 75%).

Step 6: di-tert-butyl 2-(3-cyanophenyl)-5',6',7-tetrahydro-5H-spiro[benzo[b]thiophene-4,4'-[1,3]thiazine]-2'-yliminodicarbonate Di-tert-butyl 2-bromo-5',6',7-tetrahydro-5H-spiro[benzo[b]thiophene-4,4'-[1,3]thiazine]-2'-ylcarbamate (0.51 g, 1 mmol) was dissolved in DMF (15 mL). Aqueous Cs$_2$CO$_3$ (3.7 M, 0.6 mL) and 3-cyanophenyl boronic acid (0.147 g, 1 mmol) was added and the solution was degassed under a stream of nitrogen for 10 min. Pd(dppf)Cl$_2$ (0.082 g, 0.1 mmol) was added and the reaction was heated at 90° C. for 2 hr. The reaction was cooled and evaporated in vacuo to leave a residue that was purified on silica gel using a gradient elution of 0-75% ethyl acetate in 40-60 petroleum ether (0.41 g, 76%). $^1$H NMR δ (ppm)(CHCl$_3$-d): 7.80 (1H, t, J=1.68 Hz), 7.71 (1H, dt, J=7.86, 1.53 Hz), 7.54-7.42 (2H, m), 7.17 (1H, s), 3.28 (1H, ddd, J=12.69, 10.13, 4.84 Hz), 3.12 (1H, dt, J=12.72, 4.72 Hz), 2.96-2.81 (2H, m), 2.13-1.86 (5H, m), 1.87-1.78 (1H, m), 1.53 (18H, s). LCMS (Method e) Rt 5.12 (min) m/z 562 (MH$^+$).

Step 7: 3-(2'-amino-5',6',7-tetrahydro-5H-spiro[benzo[b]thiophene-4,4'-[1,3]thiazine]-2-yl)benzonitrile, Formate Salt Di-tert-butyl 2-(3-cyanophenyl)-5',6',7-tetrahydro-5H-spiro[benzo[b]thiophene-4,4'-[1,3]thiazine]-2'-yliminodicarbonate (0.084 g, 0.25 mmol) was stirred in trifluoroacetic acid (1 mL) for 18 hr at room temperature. The reaction was evaporated in vacuo to leave a residue that was purified using preparative HPLC to give the title compound as off-white solid and formate salt (21 mg, 25%). $^1$H NMR δ (ppm) (CHCl$_3$-d): 8.45 (1H, s), 7.80 (1H, s), 7.74 (1H, dt, J=7.87, 1.53 Hz), 7.53 (1H, dt, J=7.71, 1.38 Hz), 7.46 (1H, t, J=7.78 Hz), 7.15 (1H, s), 3.26-3.13 (2H, m), 3.01-2.91 (1H, m), 2.81 (1H, dt, J=16.94, 5.24 Hz), 2.44-2.36 (1H, m), 2.28-2.09 (3H, m), 2.01-1.89 (2H, m). No NH$_2$ peak observed. HPLC (Method a) Rt 7.75 (min) m/z 340 (MH$^+$).

Example 2

(R)-3-(2'-amino-5',6',7-tetrahydro-5H-spiro[benzo[b]thiophene-4,4'-[1,3]thiazine]-2-yl)benzonitrile 3-(2'-amino-5',6',7-tetrahydro-5H-spiro[benzo[b]thiophene-4,4'-[1,3]thiazine]-2-yl)benzonitrile was purified using chiral preparative HPLC to give the title compound as white solid (5.9 mg, retention time=10.68 min) and its enantiomer as white solid, (S)-3-(2'-amino-5',6',7-tetrahydro-5H-spiro[benzo[b]thiophene-4,4'-[1,3]thiazine]-2-yl)benzonitrile (3.9 mg, retention time=13.66 min) (R)-enantiomer: $^1$H NMR δ (ppm)(CHCl$_3$-d): 7.79 (1H, s), 7.73 (1H, dt, J=7.85, 1.52 Hz), 7.52-7.40 (2H, m), 7.13 (1H, s), 3.24-3.15 (1H, m), 3.07 (1H, ddd, J=12.47, 6.49, 4.13 Hz), 2.93-2.77 (2H, m), 2.10-1.95 (3H, m), 1.95-1.78 (3H, m). No NH$_2$ peak observed. LCMS (Method e) Rt 2.67 (min) m/z 340 (MH$^+$).

(S)-enantiomer: $^1$H NMR δ (ppm)(CHCl$_3$-d): 7.79 (1H, t, J=1.68 Hz), 7.73 (1H, dt, J=7.84, 1.55 Hz), 7.52-7.41 (2H, m), 7.13 (1H, s), 3.20 (1H, ddd, J=12.43, 9.74, 4.38 Hz), 3.06 (1H, ddd, J=12.45, 6.23, 4.26 Hz), 2.92-2.77 (2H, m), 2.09-1.93 (3H, m), 1.94-1.80 (3H, m). No NH2 peak observed. LCMS (Method e) Rt 2.67 (min) m/z 340 (MH$^+$).

Similarly prepared using Method 1 with different boronic acid or ester derivatives, were:

| Structure | MH$^+$ | HPLC Rt | NMR |
|---|---|---|---|
| (4-fluorophenyl substituted spiro compound, 3) | 333 | 7.87$^a$ | $^1$H NMR δ (ppm) (CHCl$_3$-d): 7.51-7.44 (2 H, m), 7.05-6.98 (3 H, m), 4.28 (2 H, s), 3.19 (1 H, ddd, J = 12.41, 10.00, 4.04 Hz), 3.07 (1 H, ddd, J = 12.41, 6.44, 4.12 Hz), 2.91-2.75 (2 H, m), 2.09-1.97 (2 H, m), 1.98-1.78 (4 H, m). (off-white solid) |

| Structure | MH+ | HPLC Rt | NMR |
|---|---|---|---|
| 4 | 316 | 6.7[a] | ¹H NMR δ (ppm) (CHCl₃-d): 8.69 (1 H, d, J = 2.36 Hz), 8.35 (1 H, dd, J = 4.85, 1.57 Hz), 7.80 (1 H, dt, J = 8.00, 1.95 Hz), 7.29-7.14 (1 H, m, overlapping with solvent peak), 7.02 (1 H, s), 3.09-3.00 (1 H, m), 2.91 (1 H, ddd, J = 12.47, 6.35, 4.07 Hz), 2.79-2.63 (2 H, m), 1.95-1.64 (6 H, m). No NH₂ peak observed. (off-white solid) |
| 5 formate salt | 346 | 2.15[b] | ¹H NMR δ (ppm) (CHCl₃-d): 8.48 (1 H, s), 8.34 (1 H, d, J = 2.52 Hz), 7.73 (1 H, dd, J = 8.62, 2.56 Hz), 6.99 (1 H, s), 6.76 (1 H, d, J = 8.61 Hz), 3.96 (3 H, s), 3.21 (2 H, t, J = 6.02 Hz), 3.00-2.89 (1 H, m), 2.79 (1 H, dt, J = 16.85, 5.19 Hz), 2.45-2.37 (1 H, m), 2.25 (1 H, t, J = 12.27 Hz), 2.18-2.08 (2 H, m), 2.00-1.89 (2 H, m). No NH₂ peak observed. (off-white solid) |
| 6 formate salt | 357 | 2.29[b] | ¹H NMR δ (ppm) (CHCl₃-d): 8.45 (1 H, s), 7.31 (1 H s), 7.21 (1 H, dd, J = 8.44, 2.28), 6.94 (1 H, s), 6.77 (1 H, d, J = 8.29 Hz), 4.60 (2 H, t, J = 8.68 Hz), 3.28-3.14 (4 H, m), 2.92 (1 H, ddd, J = 16.94, 8.30, 5.79 Hz), 2.78 (1 H, dt, J = 16.84, 5.30 Hz), 2.47-2.38 (1 H, m), 2.21-2.02 (3 H, m), 2.00-1.87 (2 H, m). No NH₂ peak observed. (off-white solid) |
| 7 | 317 | 8.92[c] | ¹H NMR δ (ppm) (CHCl₃-d): 9.07 (1 H, s), 8.88 (2 H, s), 7.19 (1 H, s), 3.22 (1 H, ddd, J = 12.45, 9.24, 5.07 Hz), 3.07 (1 H, dt, J = 12.48, 5.13 Hz), 2.92-2.81 (2 H, m), 2.11-1.82 (6 H, m). No NH₂ peak observed. (off-white solid) |
| 8 | 359 | 2.29[b] | ¹H NMR δ (ppm) (CHCl₃-d): 8.36 (0.5 H, s), 7.0-6.88 (2 H, m), 6.87 (1 H, s), 6.73 (1 H, d, J = 8.07 Hz), 5.90 (2 H, s), 3.23-3.11 (2 H, m), 2.89-2.78 (1 H, m), 2.70 (1 H, d, J = 16.70 Hz), 2.38-2.29 (1 H, m), 2.08 (2 H, t, J = 13.81 Hz), 2.00 (1 H, s), 1.85 (2 H, s). No NH₂ peak observed. (off-white solid) |
| 9 | 393 | 2.07[b] | ¹H NMR δ (ppm) (CHCl₃-d): 8.08 (1 H, t, J = 1.88 Hz), 7.78 (2 H, d, J = 7.76 Hz), 7.56-7.49 (1 H, m), 7.21-7.17 (1 H, m), 3.21 (1 H, ddd, J = 12.44, 9.25, 5.18 Hz), 3.12-3.02 (4 H, m), 2.94-2.78 (2 H, m), 2.10-1.79 (6 H, m). No NH₂ peak observed. (off-white solid) |

-continued

| Structure | MH+ | HPLC Rt | NMR |
|---|---|---|---|
| 10 formate salt | 370 | 2.69[e] | ¹H NMR δ (ppm) (CHCl₃-d): 8.48 (1 H, s), 7.84 (1 H, d, J = 2.09 Hz), 7.54 (1 H, dd, J = 8.59, 2.12 Hz), 7.30 (1 H, s), 7.03-6.96 (1 H, m), 3.98 (3 H, s), 3.25-3.18 (2 H, m), 3.01-2.90 (1 H, m), 2.82 (1 H, dt, J = 17.24, 4.97 Hz), 2.46-2.37 (1 H, m), 2.27 (1 H, t, J = 12.42 Hz), 2.19-2.07 (2 H, m), 2.01-1.90 (2 H, m). No NH₂ peak observed. (off-white solid) |
| 11 formate salt | 388 | 7.83[a] | ¹H NMR δ (ppm) (CHCl₃-d): 8.39 (1 H, s), 7.45 (1 H, dd, J = 6.00, 1.92 Hz), 7.27 (1 H, s, obscured by solvent peak), 7.10-7.05 (1 H, m), 3.91 (3 H, s), 3.25-3.10 (2 H, m), 3.00-2.88 (2 H, m), 2.85-2.74 (1 H, m), 2.41-2.32 (1 H, m), 2.22-2.06 (2 H, m), 2.00-1.86 (2 H, m). No NH₂ peak observed. (off-white solid) |
| 12 formate salt | 358 | 3.37[d] | ¹H NMR δ (ppm) (CHCl₃-d): 8.38 (1 H, s), 7.61-7.57 (1 H, m), 7.45 (1 H, dt, J = 9.54, 1.98 Hz), 7.24-7.15 (2 H, m), 3.23 (1 H, ddd, J = 12.94, 9.58, 3.61 Hz), 3.15-3.06 (1 H, m), 3.03-2.90 (1 H, m), 2.83-2.72 (2 H, m), 2.39-2.30 (1 H, m), 2.20-2.03 (2 H, m), 1.99-1.85 (2 H, m). No NH₂ peak observed. (white solid) |
| 13 formate salt | 373 | 3.36[d] | ¹H NMR δ (ppm) (CHCl₃-d): 8.46 (1 H, s), 8.19 (1 H, t, J = 1.76 Hz), 7.92 (1 H, d, J = 7.78 Hz), 7.73-7.69 (1 H, m), 7.43 (1 H, t, J = 7.78 Hz), 7.15 (1 H, s), 3.95 (3 H, s), 3.21 (2 H, t, J = 6.02 Hz), 3.01-2.91 (1 H, m), 2.81 (1 H, dt, J = 16.82, 5.22 Hz), 2.47-2.39 (1 H, m), 2.31-2.23 (1 H, m), 2.18-2.08 (2 H, m), 2.00-1.88 (2 H, m). No NH₂ peak observed. (white solid) |
| 14 formate salt | 358 | 7.86[a] | ¹H NMR δ (ppm) (CHCl₃-d): 8.43 (1 H, s), 7.78-7.68 (2 H, m), 7.24-7.14 (1 H, m), 7.08 (1 H, s), 3.27-3.11 (2 H, m), 3.00-2.89 (1 H, m), 2.80 (1 H, dt, J = 16.97, 5.27 Hz), 2.43-2.34 (1 H, m), 2.25-2.08 (3 H, m), 2.02-1.88 (2 H, m). No NH₂ peak observed. (off-white solid) |
| 15 formate salt | 358 | 7.76[a] | ¹H NMR δ (ppm) (CHCl₃-d): 8.46 (1 H, s), 7.87 (1 H, dd, J = 7.04, 2.09 Hz), 7.53 (1 H, ddd, J = 8.55, 4.45, 2.11 Hz), 7.31 (1 H, s), 7.24-7.18 (1 H, m), 3.27-3.15 (2 H, m), 3.03-2.93 (1 H, m), 2.83 (1 H, dt, J = 17.01, 5.25 Hz), 2.44-2.36 (1 H, m), 2.30-2.21 (1 H, m), 2.19-2.08 (2 H, m), 2.01-1.90 (2 H, m). No NH₂ peak observed. (off-white solid) |

| Structure | MH+ | HPLC Rt | NMR |
| --- | --- | --- | --- |
| 16 formate salt | 374 | 7.91[a] | $^{1}$H NMR δ (ppm) (CHCl$_3$-d): 8.39 (1 H, s), 7.75 (1 H, d, J = 1.97 Hz), 7.52 (1 H, t, J = 8.30 Hz), 7.50-7.44 (1 H, m), 7.15 (1 H, s), 3.25-3.11 (2 H, m), 3.00-2.87 (2 H, m), 2.84-2.74 (1 H, m), 2.41-2.32 (1 H, m), 2.21-2.05 (2 H, m), 1.97-1.86 (2 H, m). No NH$_2$ peak observed. (off-white solid) |
| 17 formate salt | 370 | 2.76[e] | $^{1}$H NMR δ (ppm) (CHCl$_3$-d): 8.41 (1 H, s), 7.39 (1 H, t, J = 1.43 Hz), 7.25-7.22 (1 H, m), 7.11 (1 H, s), 7.04-6.99 (1 H, m), 3.87 (3 H, s), 3.28-3.15 (2 H, m), 3.01-2.91 (1 H, m), 2.81 (1 H, dt, J = 17.06, 5.23 Hz), 2.46-2.37 (1 H, m), 2.27-2.09 (3 H, m), 2.00-1.89 (2 H, m). No NH$_2$ peak observed. (off-white solid) |
| 18 formate salt | 371 | 7.76[a] | $^{1}$H NMR δ (ppm) (CHCl$_3$-d): 8.49 (1 H, d, J = 2.50 Hz), 8.36 (1 H, s), 8.00 (1 H, d, J = 2.51 Hz), 7.04 (1 H, s), 4.07 (3 H, s), 3.29-3.13 (2 H, m), 3.01-2.90 (1 H, m), 2.80 (1 H, dd, J = 17.32, 0.04 Hz), 2.45-2.36 (1 H, m), 2.28-2.08 (3 H, m), 1.98-1.90 (2 H, m). No NH$_2$ peak observed. (white solid) |
| 19 formate salt | 341 | 7.35[a] | $^{1}$H NMR δ (ppm) (CHCl$_3$-d): 8.91 (1 H, d, J = 2.27 Hz), 8.67 (1 H, d, J = 1.87 Hz), 8.27 (1 H, s), 8.08 (1 H, t, J = 2.08 Hz), 7.25 (1 H, s), 3.28-3.19 (1 H, m), 3.15-3.07 (1 H, m), 3.00-2.89 (1 H, m), 2.78 (1 H, dt, J = 17.22, 5.49 Hz), 2.37 (1 H, ddd, J = 14.34, 9.84, 3.73 Hz), 2.24-2.04 (3 H, m), 1.96-1.85 (2 H, m). No NH$_2$ peak observed. (off-white solid) |
| 20 | 341 | 2.49[e] | $^{1}$H NMR δ (ppm) (CHCl$_3$-d): 8.65 (1 H, d, J = 5.26 Hz), 7.80 (1 H, d, J = 1.77 Hz), 7.58 (1 H, dd, J = 5.25, 1.87 Hz), 7.35-7.30 (1 H, m), 3.33-3.17 (2 H, m), 3.04-2.97 (1 H, m), 2.87 (1 H, dt, J = 17.64, 5.20 Hz), 2.49-2.41 (1 H, m), 2.29-2.14 (3 H, m), 2.04-1.96 (2 H, m). No NH$_2$ peak observed. (off-white solid) |
| 21 formate salt | 391 | 3.05[a] | $^{1}$H NMR δ (ppm) (CHCl$_3$-d): 8.44 (1 H, s), 7.70 (1 H, s), 7.61-7.56 (2 H, m), 7.54-7.32 (6 H, m), 7.11 (1 H, s), 3.24-3.10 (2 H, m), 2.93 (1 H, ddd, J = 17.04, 8.37, 5.79 Hz), 2.78 (1 H, dt, J = 17.15, 5.58 Hz), 2.44-2.34 (1 H, m), 2.21-2.04 (3 H, m), 1.99-1.82 (2 H, m). No NH$_2$ peak observed. (off-white solid) |

-continued

| Structure | MH+ | HPLC Rt | NMR |
|---|---|---|---|
| 22 formate salt | 370 | 7.78[a] | ¹H NMR δ (ppm) (CHCl₃-d): 8.39 (1 H, s), 7.72-7.66 (2 H, m), 7.03-6.95 (2 H, m), 3.96 (3 H, s), 3.27-3.16 (2 H, m), 3.00-2.89 (1 H, m), 2.80 (1 H, dt, J = 16.92, 5.15 Hz), 2.47-2.38 (1 H, m), 2.28-2.09 (3 H, m), 1.99-1.90 (2 H, m). No NH₂ peak observed. (off-white solid) |
| 23 formate salt | 359 | 7.79[a] | ¹H NMR δ (ppm) (CHCl₃-d): 8.48 (1 H, s), 7.54-7.40 (2 H, m), 7.42-7.28 (1 H, m), 7.29-7.20 (1 H, m), 7.09 (1 H, s), 4.51-4.42 (2 H, m), 3.43-3.33 (3 H, m), 3.17 (2 H, s), 2.99-2.88 (1 H, m), 2.78 (1 H, d, J = 16.74 Hz), 2.44-2.35 (1 H, m), 2.28-2.15 (1 H, m), 2.14-2.05 (2 H, m), 1.91 (2 H, s). No NH₂ peak observed. (off-white solid) |
| 24 formate salt | 399 | 3.33[d] | ¹H NMR δ (ppm) (CHCl₃-d): 8.46 (1 H, s), 7.47 (1 H, d, J = 7.88 Hz), 7.42-7.34 (2 H, m), 7.15-7.11 (2 H, m), 3.25-3.13 (2 H, m), 3.01-2.91 (1 H, m), 2.80 (1 H, dt, J = 16.95, 5.21 Hz), 2.46-2.37 (1 H, m), 2.27-2.07 (3 H, m), 2.01-1.89 (2 H, m). No NH₂ peak observed. (off-white solid) |
| 25 formate salt | 383 | 3.87[d] | ¹H NMR δ (ppm) (CHCl₃-d): 8.48 (1 H, s), 7.79-7.66 (2 H, m), 7.54-7.44 (2 H, m), 7.15 (1 H, s), 3.24-3.12 (2 H, m), 2.97 (1 H, ddd, J = 17.11, 8.46, 5.92 Hz), 2.81 (1 H, dt, J = 16.99, 5.25 Hz), 2.46-2.36 (1 H, m), 2.28-2.08 (3 H, m), 2.02-1.88 (2 H, m). No NH₂ peak observed. (brown solid) |
| 26 formate salt | 407 | 2.6[b] | ¹H NMR δ (ppm) (CHCl₃-d): 8.46 (1 H, s), 7.41-7.25 (5 H, m), 7.22 (1 H, s), 7.16-7.02 (3 H, m), 6.90-6.85 (1 H, m), 3.20 (2 H, t, J = 6.01 Hz), 3.00-2.89 (1 H, m), 2.79 (1 H, dt, J = 16.99, 5.31 Hz), 2.46-2.38 (1 H, m), 2.26 (1 H, t, J = 12.20 Hz), 2.20-2.06 (2 H, m), 1.93 (2 H, dd, J = 12.72, 5.43 Hz). No NH₂ peak observed. (off-white solid) |
| 27 formate salt | 357 | 3.59[d] | ¹H NMR δ (ppm) (CHCl₃-d): 8.51 (1 H, s), 7.36 (2 H, d, J = 8.83 Hz), 7.31-7.24 (1 H, m), 7.14 (1 H, d, J = 7.63 Hz), 7.07 (1 H, s), 3.15 (2 H, t, J = 6.04 Hz), 3.00-2.87 (2 H, m), 2.78 (1 H, dt, J = 16.84, 5.11 Hz), 2.42-2.32 (1 H, m), 2.29-2.15 (1 H, m), 2.15-1.97 (2 H, m), 1.96-1.86 (2 H, m), 1.28 (6 H, d, J = 6.92 Hz). No NH₂ peak observed. (brown solid) |

-continued

| Structure | MH+ | HPLC Rt | NMR |
|---|---|---|---|
| 28 | 349 | 2.43[b] | ¹H NMR δ (ppm) (CHCl₃-d): 8.45 (1 H, s), 7.52 (1 H, s), 7.41 (1 H, d, J = 7.64 Hz), 7.36-7.18 (2 H, m), 7.10 (1 H, s), 3.21 (2 H, t, J = 5.97 Hz), 3.02-2.92 (1 H, m), 2.85-2.74 (1 H, m), 2.47-2.39 (1 H, m), 2.25 (1 H, d, J = 12.76 Hz), 2.20-2.09 (2 H, m), 1.94 (2 H, dd, J = 13.27, 6.45 Hz). No NH₂ peak observed. (off-white solid) |
| 29 formate salt | 391 | 8.99[a] | ¹H NMR δ (ppm) (CHCl₃-d): 8.49 (1 H, s), 7.65-7.58 (6 H, m), 7.46 (2 H, t, J = 7.56 Hz), 7.37 (1 H, d, J = 7.35 Hz), 7.13 (1 H, s), 3.24 (1 H, dt, J = 7.65, 4.02 Hz), 2.28 (1 H, s), 2.21-2.09 (6 H, m), 2.00-1.91 (2 H, m). No NH₂ peak observed. (off-white solid) |
| 30 formate salt | 421 | 2.62[b] | ¹H NMR δ (ppm) (CHCl₃-d): 8.48 (1 H, s), 7.49-7.32 (5 H, m), 7.31-7.23 (1 H, m, obscured by solvent peak), 7.15 (2 H, t, J = 5.22 Hz), 7.06 (1 H, s), 6.89 (1 H, dd, J = 8.21, 2.44 Hz), 5.11 (2 H, s), 3.23-3.17 (2 H, m), 2.93 (1 H, t, J = 8.04 Hz), 2.82 (1 H, t, J = 5.29 Hz), 2.47-2.39 (1 H, m), 2.25 (1 H, d, J = 13.13 Hz), 2.16-2.06 (2 H, m), 1.97-1.90 (2 H, m). No NH₂ peak observed. (off-white solid) |

[a-f]Rt refers to HPLC method A to F

Method 2:

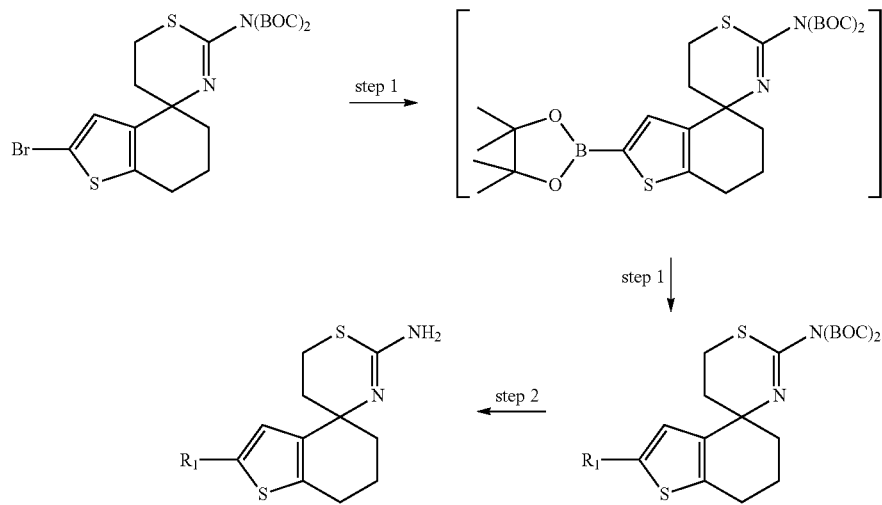

Step 1

Di-tert-butyl 2-bromo-5',6,6',7-tetrahydro-5H-spiro[benzo[b]thiophene-4,4'-[1,3]thiazine]-2'-ylcarbamate (0.1 g, 0.2 mmol) was dissolved in DMF (1 mL), bis(pinacolato) diboron (90 mg, 0.4 mmol), potassium acetate (59 mg, 0.6 mmol) and Pd(dppf)Cl$_2$ (16 mg, 0.02 mmol) were added and the solution was degassed under a stream of nitrogen for 10 min. The reaction was heated for 15 min at 80° C. The mixture was cooled and an aromatic or heteroaromatic bromide or chloride (0.2 mmol) and aqueous Cs$_2$CO$_3$ (0.15 mL, 3.7 M, 0.55 mmol) were added and the solution was degassed again under a stream of nitrogen for 10 min Pd(dppf)Cl$_2$ (16 mg, 0.02 mmol) was added and the solution was heated for 2 hr at 80° C. The reaction was then cooled and evaporated in vacuo to leave a residue that was used directly in the next step without further purification.

Step 2

Di-tert-butyl protected intermediate from step 1 (0.2 mmol) was stirred in trifluoroacteic acid (2 mL) for 18 hr at room temperature. The reaction mixture was evaporated in vacuo to leave a residue that was purified using preparative HPLC to give the desired product. Similarly prepared using Method 2, with different aryl or heteroaryl bromide, were:

| Structure | MH$^+$ | HPLC Rt | NMR |
|---|---|---|---|
| 31 | 341 | 7.84$^a$ | $^1$H NMR δ (ppm) (DMSO-d$_6$): 8.27-8.16 (1 H, m), 8.05 (1 H, t, J = 7.90 Hz), 7.90-7.81 (2 H, m), 3.30 (1 H, t, J = 12.22 Hz), 3.16 (1 H, d, J = 13.32 Hz), 2.88-2.73 (2 H, m), 2.20 (1 H, t, J = 11.83 Hz), 2.10 (1 H, d, J = 11.07 Hz), 1.91 (3 H, s), 1.83 (1 H, d, J = 13.17 Hz). No NH$_2$ peak observed. (off-white solid) |
| 32 | 408 | 2.91$^e$ | $^1$H NMR δ (ppm) (CHCl$_3$-d): 8.42 (1 H, s), 7.95 (2 H, d, J = 9.31 Hz), 7.76 (1 H, s), 7.23 (1 H, s), 3.27 (1 H, t, J = 10.76 Hz), 3.21-3.13 (1 H, m), 3.05-2.95 (1 H, m), 2.88-2.78 (1 H, m), 2.44-2.35 (1 H, m), 2.30-2.10 (3 H, m), 1.96 (2 H, t, J = 11.28 Hz). No NH$_2$ peak observed. (brown solid) |
| 33 formate salt | 421 | 3.07$^e$ | $^1$H NMR δ (ppm) (CHCl$_3$-d): 8.51 (1 H, s), 7.68 (1 H, s), 7.56 (2 H, d, J = 8.37 Hz), 7.48-7.37 (3 H, m), 7.10 (1 H, s), 7.00 (2 H, d, J = 8.23 Hz), 3.86 (3 H, s), 3.20 (2 H, s), 3.02-2.74 (2H, m), 2.44-2.03 (4 H m), 1.94 (2 H, s). No NH$_2$ peak observed. (brown solid) |
| 34 formate salt | 374 | 7.93$^a$ | $^1$H NMR δ (ppm) (CHCl$_3$-d): 8.43 (1 H, s), 7.70 (2 H, dt, J = 14.93, 1.68 Hz), 7.50 (1 H, t, J = 1.60 Hz), 7.16 (1 H, s), 3.27-3.14 (2 H, m), 3.00-2.93 (1 H, m), 2.84 (1 H, t, J = 5.30 Hz), 2.42-2.35 (1 H, m), 2.23 (1 H, d, J = 10.17 Hz), 2.16 (2 H, ddd, J = 14.41, 7.84, 3.84 Hz), 1.94 (2 H, dd, J = 13.36, 6.80 Hz). No NH$_2$ peak observed. (brown solid) |

-continued

| Structure | MH+ | HPLC Rt | NMR |
|---|---|---|---|
| 35 formate salt | 354 | 7.84[a] | 1H NMR δ (ppm) (CHCl3-d): 8.46 (1 H, s), 7.60 (1 H, s), 7.54 (1 H, s), 7.34 (1 H, s), 7.11 (1 H, s), 3.25-3.17 (2 H, m), 2.99-2.90 (1 H, m), 2.83 (1 H, s), 2.49-2.31 (3 H, m), 2.25 (1 H, t, J = 12.12 Hz), 2.18-2.10 (2 H, m), 1.94 (3 H, d, J = 11.98 Hz). No NH2 peak observed. (beige solid) |
| 36 formate salt | 392 | 2.16[b] | 1H NMR δ (ppm) (CHCl3-d): 8.71 (1 H, d, J = 4.88 Hz), 8.47 (1 H, s), 8.15 (1 H, s), 7.86 (1 H, d, J = 7.88 Hz), 7.77 (2 H, s), 7.58 (1 H, d, J = 7.83 Hz), 7.53-7.41 (1 H, m), 7.17 (2 H, s), 3.19 (2 H, s), 3.02-2.90 (1 H, m), 2.80 (1 H, d, J = 17.26 Hz), 2.48-2.38 (1 H, m), 2.25 (1 H, t, J = 12.30 Hz), 2.17-2.07 (2 H, m), 1.93 (2 H, t, J = 6.83 Hz). No NH2 peak observed. (yellow solid) |
| 37 formate salt | 371 | 2.65[b] | 1H NMR δ (ppm) (CHCl3-d): 8.48 (1 H, s), 7.52 (1 H, s), 7.40-7.24 (3 H, m, overlapping with solvent peak), 7.05 (1 H, s), 3.20 (2 H, s), 3.00-2.90 (1 H, m), 2.84-2.74 (1 H, m), 2.47-2.38 (1 H, m), 2.26 (1 H, t, J = 11.75 Hz), 2.17-2.04 (2 H, m), 1.94 (2 H, t, J = 11.26 Hz), 1.35 (9 H, s). No NH2 peak observed. (brown solid) |
| 38 formate salt | 421 | 2.59[b] | 1H NMR δ (ppm) (CHCl3-d): 8.47 (1 H, s), 7.71 (1 H, s), 7.51-7.34 (4 H, m), 7.20 (1 H, d, J = 7.93 Hz), 7.13 (2 H, d, J = 12.05 Hz), 6.98-6.88 (1H, m), 3.88 (3 H, s), 3.31-3.16 (2 H, m), 3.04-2.89 (1 H, m), 2.87-2.76 (1 H, m), 2.54-2.39 (1 H, m), 2.34-2.21 (1 H, m), 2.20-2.06 (2 H, m), 1.99-1.88 (2 H, m). No NH2 peak observed. (brown solid) |
| 39 formate salt | 397 | 2.46[b] | 1H NMR δ (ppm) (CHCl3-d): 8.49 (0.25 H, s), 7.52 (1 H, d, J = 7.89 Hz), 7.46 (1 H, s), 7.37 (1 H, t, J = 7.73 Hz), 7.23 (1 H, d, J = 7.68 Hz), 7.08 (1 H, s), 3.42 (2 H, q, J = 10.77 Hz), 3.22 (2 H, d, J = 6.37 Hz), 3.02-2.91 (1 H, m), 2.87-2.78 (1 H, m), 2.49-2.40 (1 H, m), 2.25 (1 H, t, J = 12.53 Hz), 2.17-2.08 (2 H, m), 2.00-1.93 (2 H, m). No NH2 peak observed. (yellow solid) |

[a-f]Rt refers to HPLC method A to F

Method 3:

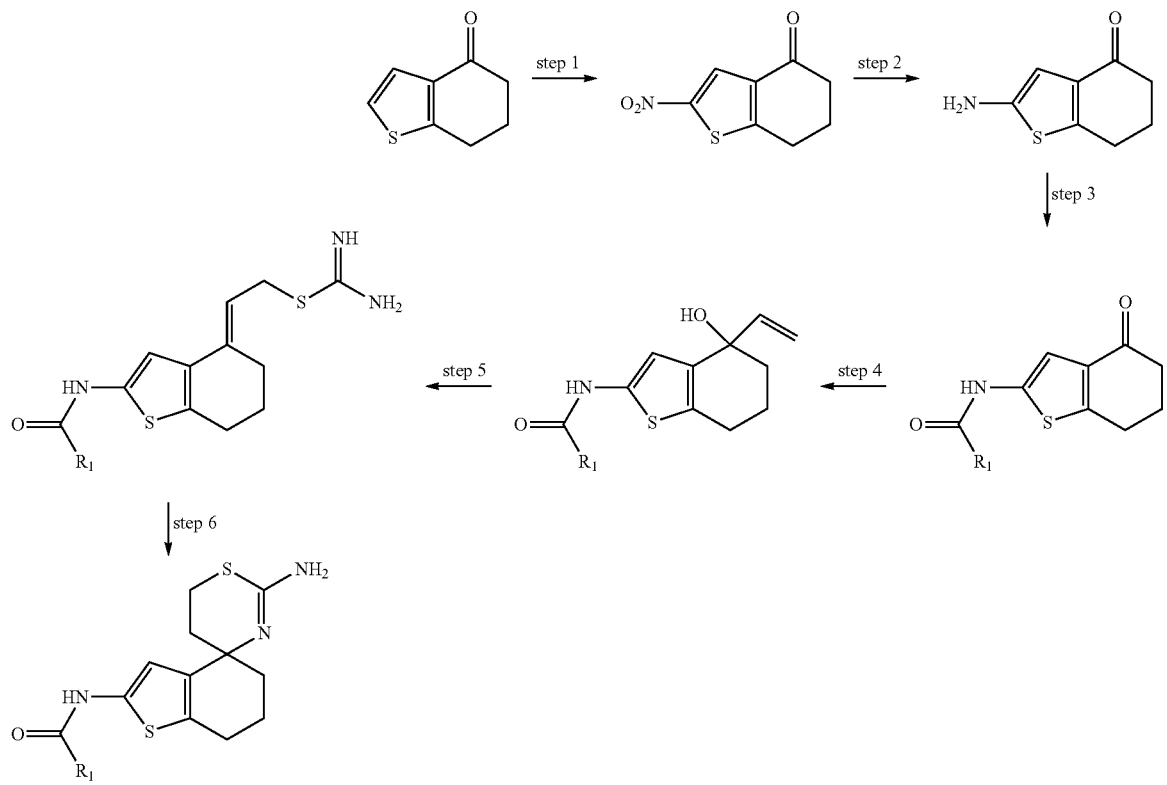

Step 1:
2-nitro-6,7-dihydrobenzo[b]thiophen-4(5H)-one 6,7-Dihydrobenzo[b]thiophen-4(5H)-one (5 g, 32.9 mmol) was dissolved in concentrated sulphuric acid (30 mL) and cooled to 0° C. in an ice/salt bath. Concentrated nitric acid (3.5 mL) in concentrated sulphuric acid (20 mL) was added drop-wise keeping the temperature of the reaction below 0° C. The reaction mixture was stirred at 0-5° C. for 1 hr. The solution was poured onto ice and the resulting solid filtered, washed with water and dried in a vacuum oven, affording the title compound (5.68 g, 88%).

Step 2:
2-amino-6,7-dihydrobenzo[b]thiophen-4(5H)-one

2-Nitro-6,7-dihydrobenzo[b]thiophen-4(5H)-one (3.6 g, 18.2 mmol) was dissolved in DMF (50 mL) and stirred under an atmosphere of hydrogen (300 psi) for 18 hr with 10% palladium on carbon. The mixture was filtered through celite and used directly in the next step as a solution in DMF.

Step 3

2-Amino-6,7-dihydrobenzo[b]thiophen-4(5H)-one (0.4 g, 2.7 mmol) in DMF (10 mL) was treated with a carboxylic acid (2.7 mmol), HATU (0.91 g, 2.7 mmol) and di-isopropylethylamine (1.24 g, 1.7 mL, 9.6 mmol). The resulting mixture was stirred at room temperature for 1 hr. The mixture was concentrated in vacuo to leave a residue that was purified on silica gel using a gradient elution of 0-100% ethyl acetate in 40-60 petroleum ether to afford the desired ketone.

Step 4

Ketone derivative obtained in Step 3 (0.7 mmol) was dissolved in anhydrous THF (20 mL) and the solution was cooled to −40° C. under a nitrogen atmosphere. Vinyl magnesium chloride (2.55 mL, 1.6 M solution in THF, 4.2 mmol) was added to the ketone portion-wise whilst maintaining the temperature at −40° C. Upon completion of the addition, the reaction was stirred at −30° C. for 30 min and then allowed to warm to 25° C. The solution was then treated with saturated aqueous ammonium chloride solution. The product was extracted into ethyl acetate and this was back extracted with water and saturated brine. The ethyl acetate solution was dried (MgSO$_4$), filtered and concentrated in vacuo to afford the desired product as a crude, yellow oil which crystallised on standing. Trituration with diethyl ether provided the desired product as solid.

Step 5

Product obtained in Step 4 (0.17 mmol) was suspended in acetic acid (0.35 mL). Thiourea (14 mg, 0.19 mmol) was added and the reaction was stirred at 25° C. for 2 hr. The majority of the acetic acid was removed in vacuo and the residue was diluted with diethyl ether to afford an off-white solid. This was filtered off and washed with additional ether before being dried in vacuo to afford the desired product as the acetate salt.

Step 6

Product obtained in Step 5 (0.08 mmol) was suspended in concentrated HCl (1 mL) and stirred at 25° C. until all the solid dissolved. The reaction was monitored by LC/MS until no more starting material remained. The mixture was then neutralised with aqueous sat. NaHCO₃ solution. The aqueous layer was then extracted with dichloromethane (×3). The organic phases were combined, dried (MgSO₄) and concentrated in vacuo to yield the desired product. In some cases, it was further purified by preparative HPLC.

Similarly prepared using Method 3, starting from different carboxylic acid, was:

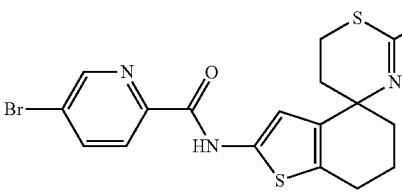

| Structure | MH+ | HPLC Rt | NMR |
|---|---|---|---|
| 40 formate salt | 437 | 2.2[b] | ¹NMR δ (ppm)(CHCl₃-d): 8.52 (1 H, s), 8.31-8.26 (1 H, m), 7.96 (1 H, d, J = 8.10 Hz), 7.89 (1 H, d, J = 7.57 Hz), 7.28-7.25 (1 H, m, overlapping with solvent peak), 6.64 (1 H, s), 3.01 (2 H, s), 2.67 (2 H, s), 2.54 (1 H, d, J = 18.32 Hz), 2.42 (1 H, s), 2.18 (1 H, s), 2.03 (1 H, t, J = 12.54 Hz), 1.91 (2 H, s), 1.77 (2 H, s). (yellow solid) |

[a-f]Rt refers to HPLC method A to F

Example 41

2-(3'-methoxybiphenyl-3-yl)-6,6-dimethyl-5',6,6',7-tetrahydro-5H-spiro[benzo[b]thiophene-4,4'-[1,3]thiazin]-2'-amine, Formate Salt Method 4

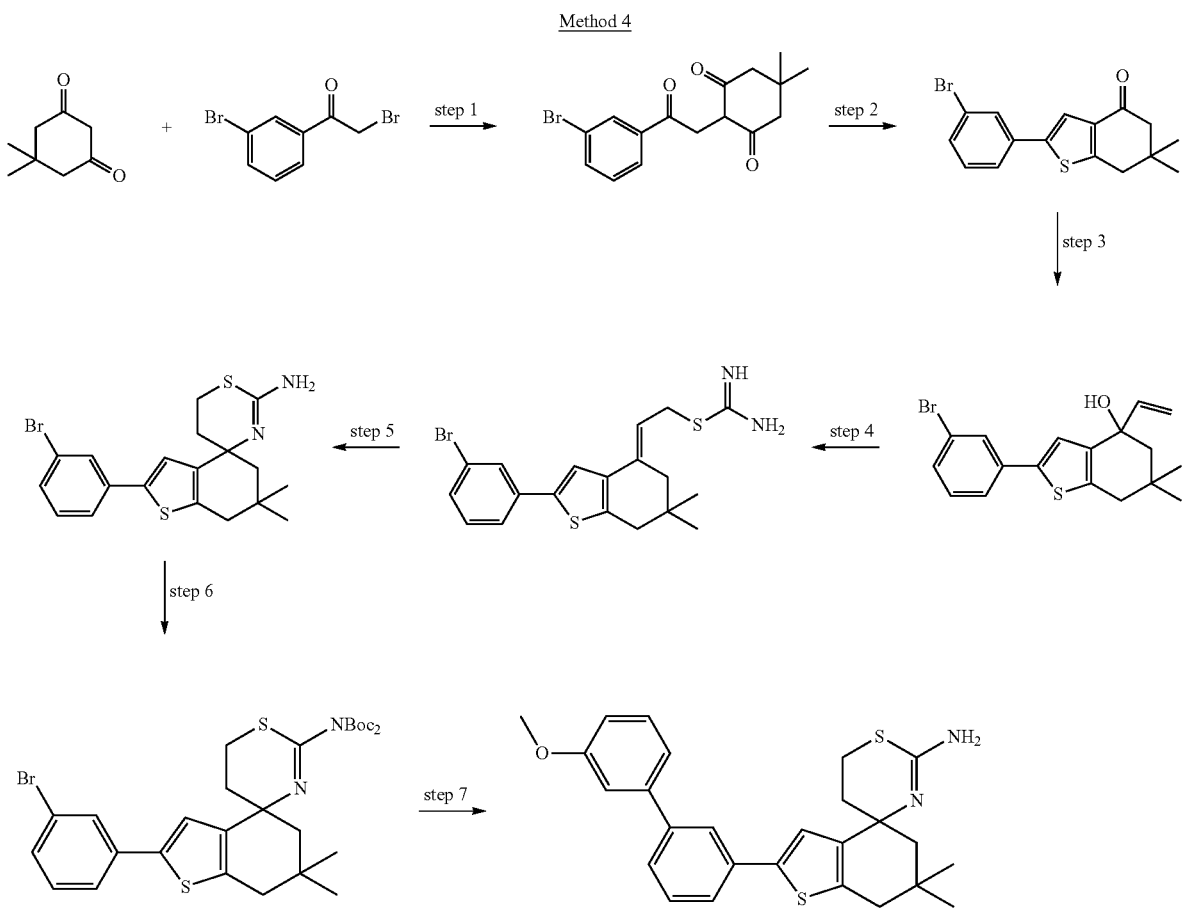

Step 1: 2-(2-(3-bromophenyl)-2-oxoethyl)-5,5-dimethylcyclohexane-1,3-dione 5,5-Dimethylcyclohexane-1,3-dione (1.4 g, 10 mmol), 2-bromo-1-(3-bromophenyl)ethanone (2.78 g, 10 mmol) and $K_2CO_3$ (1.38 g, 10 mmol) were combined in chloroform (40 mL). The mixture was stirred for 18 hr at room temperature whereupon a white precipitate formed. The solid was collected by filtration, suspended in water and acidified to pH 5 using 1M HCl (aq.). The resulting solid was filtered, washed with water and dried in vacuo to afford the title compound. The aqueous filtrate was evaporated and the crude residue purified on silica gel using a gradient elution of 0-100% ethyl acetate in 40-60 petroleum ether to yield the title product (2.77 g, 82%).

Step 2: 2-(3-bromophenyl)-6,6-dimethyl-6,7-dihydrobenzo[b]thiophen-4(5H)-one 2-(2-(3-Bromophenyl)-2-oxoethyl)-5,5-dimethylcyclohexane-1,3-dione (2.77 g, 8.2 mmol) and 2,4-bis(4-methoxyphenyl)-1,3,2,4-dithiadiphosphetane-2,4-disulfide (Lawesson's reagent) (2.29 g, 5.4 mmol) were refluxed in toluene (100 mL) for 6 hr. The reaction mixture was concentrated in vacuo and purified on silica gel using a gradient elution of 0-10% ethyl acetate in 40-60 petroleum ether to afford the title compound (0.6 g, 22%).

Step 3: 2-(3-bromophenyl)-6,6-dimethyl-4-vinyl-4,5,6,7-tetrahydrobenzo[b]thiophen-4-ol 2-(3-Bromophenyl)-6,6-dimethyl-6,7-dihydrobenzo[b]thiophen-4(5H)-one (0.36 g, 1.0 mmol) was dissolved in anhydrous THF (10 mL) and the solution was cooled to −30° C. under a nitrogen atmosphere. Vinyl magnesium chloride (2.8 mL, 1.6 M solution in THF, 5.4 mmol) was added to the ketone portion-wise whilst maintaining the temperature at −30° C. Upon completion of the addition, the reaction was allowed to warm to 25° C. and then stirred for 18 hr. Monitoring of the reaction by LC/MS indicated starting material was still present so further vinyl magnesium chloride (2.8 mL, 1.6 M solution in THF, 5.4 mmol) was added. After 2 hr the solution was treated with saturated aqueous ammonium chloride solution. The product was extracted into ethyl acetate (×3) and this was back extracted with water and saturated brine. The organic extracts were combined, dried ($MgSO_4$), filtered and concentrated in vacuo to afford the title compound (0.43 g, quant.).

Step 4: (E)-2-(2-(3-bromophenyl)-6,6-dimethyl-6,7-dihydrobenzo[b]thiophen-4(5H)-ylidene)ethyl carbamimidothioate 2-(3-Bromophenyl)-6,6-dimethyl-4-vinyl-4,5,6,7-tetrahydrobenzo[b]thiophen-4-ol (0.39 g, 1.0 mmol) was suspended in acetic acid (2.0 mL). Thiourea (83 mg, 1.0 mmol) was added and the reaction was stirred at 25° C. for 18 hr. The mixture was diluted with diethyl ether and petroleum ether yielding a solid precipitate. The solid was filtered, washed with additional diethyl ether and dried in vacuo to afford the title compound as the acetate salt (0.3 g, 60%).

Step 5: 2-(3-bromophenyl)-6,6-dimethyl-5',6,6',7-tetrahydro-5H-spiro[benzo[b]thiophene-4,4'-[1,3]thiazin]-2'-amine (E)-2-(2-(3-Bromophenyl)-6,6-dimethyl-6,7-dihydrobenzo[b]thiophen-4(5H)-ylidene)ethyl carbamimidothioate (0.31 g, 0.65 mmol) was suspended in conc. HCl (aq.) (10 mL) and iso-propanol (10 mL) and refluxed for 2 h. Further portions of iso-propanol (5 mL) and conc. HCl (aq.) (15 mL) were added and the mixture was refluxed a further 18 hr. The mixture was cooled in an ice bath and then neutralised with aqueous 2 M NaOH solution. The aqueous layer was then extracted with dichloromethane (×3). The organic phases were combined, dried ($MgSO_4$) and concentrated in vacuo to afford the title compound (0.131 g, 48%).

Step 6: Di-tert-butyl 2-(3-bromophenyl)-6,6-dimethyl-5',6,6',7-tetrahydro-5H-spiro[benzo[b]thiophene-4,4'-[1,3]thiazine]-2'-ylcarbamate 2-(3-Bromophenyl)-6,6-dimethyl-5',6,6',7-tetrahydro-5H-spiro[benzo[b]thiophene-4,4'-[1,3]thiazin]-2'-amine (0.13 g, 0.32 mmol), di-tert-butyl dicarbonate (0.27 g, 1.2 mmol), and dimethylaminopyridine (76 mg, 0.62 mmol) were stirred in dichloromethane (5 mL) at 25° C. overnight. The reaction mixture was concentrated in vacuo. The crude residue was purified on silica gel using a gradient elution of 0-50% ethyl acetate in 40-60 petroleum ether to yield the title compound as a yellow oil (0.125 g, 72%).

Step 7: 2-(3'-methoxybiphenyl-3-yl)-6,6-dimethyl-5',6,6',7-tetrahydro-5H-spiro[benzo[b]thiophene-4,4'-[1,3]thiazin]-2'-amine, Formate Salt Di-tert-butyl 2-(3-bromophenyl)-6,6-dimethyl-5',6,6',7-tetrahydro-5H-spiro[benzo[b]thiophene-4,4'-[1,3]thiazine]-2'-ylcarbamate (60 mg, 0.096 mmol) was dissolved in DMF (1 mL) and aqueous $Cs_2CO_3$ (0.1 mL, 3.7 M, 0.37 mmol). 4-Methoxyphenylboronic acid (0.0162 g, 0.10 mmol) was then added and the solution was degassed under a stream of nitrogen for 10 min. Pd(dppf)$Cl_2$ (8 mg, 0.0096 mmol) was added and the reaction was heated for 2 hr at 90° C. The reaction was then cooled and concentrated in vacuo. The crude residue was treated with trifluoroacetic acid (2 mL) and stirred for 18 hr at room temperature. The mixture was concentrated in vacuo to leave a residue that was purified using preparative HPLC to give the title compound as the formate salt as beige gum (8 mg, 19%). $^1$H NMR δ (ppm)(CHCl$_3$-d): 8.49 (1H, s), 7.81 (1H, s), 7.60 (1H, d, J=7.61 Hz), 7.53 (1H, d, J=7.71 Hz), 7.52-7.39 (2H, m), 7.29-7.25 (2H, m), 7.22 (1H, t, J=2.02 Hz), 6.99 (1H, dd, J=8.21, 2.53 Hz), 3.95 (3H, s), 3.40 (1H, dd, J=12.04, 4.06 Hz), 3.23 (1H, dt, J=12.47, 4.34 Hz), 2.81 (1H, d, J=17 Hz), 2.68 (1H, d, J=16.82 Hz), 2.40-2.30 (1H, m), 2.21 (1H, dt, J=14.11, 4.37 Hz), 2.10 (1H, d, J=14.4 Hz), 1.76 (1H, d, J=14.9 Hz), 1.23 (3H, s), 1.19 (3H, s). No NH2 peak observed. LCMS (Method b) Rt 2.72 (min) m/z 449 (MH$^+$).

Similarly prepared using Method 4, starting from different boronic acid or ester derivatives was:

| Structure | MH+ | HPLC Rt | NMR |
|---|---|---|---|
| 42 formate salt | 449 | 2.71[b] | ¹H NMR δ (ppm)(CHCl₃-d): 8.41 (1 H, s), 7.72 (1 H, s), 7.60-7.52 (2 H, m), 7.52-7.35 (3 H, m), 7.21 (1 H, s), 7.05-6.97 (2 H, m), 3.87 (3 H, s), 3.34 (1 H, td, J = 12.08, 3.99 Hz), 3.16 (1 H, dt, J = 12.51, 4.46 Hz), 2.75 (1 H, d, J = 16.6 Hz), 2.59 (1 H, d, J = 16.6 Hz), 2.36-2.26 (1 H, m), 2.16 (1 H, dt, J = 14.17, 4.35 Hz), 2.03 (1 H, d, J = 15.4 Hz), 1.70 (1 H, d, J = 14.1 Hz), 1.16 (3 H, s), 1.13 (3 H, s). No NH₂ peak observed. (beige solid) |

[a-f]Rt refers to HPLC method A to F

Similarly prepared using Method 4 starting from 5-phenyl-cyclohexane-1,3-dione and different boronic acid or ester derivatives were:

| Structure | MH+ | HPLC Rt | NMR |
|---|---|---|---|
| 43 formate salt | 469 | 2.69[b] | ¹H NMR δ (ppm)(CHCl₃-d): 8.44 (1 H, s), 7.72-7.70 (1 H, m), 7.47 (1 H, d, J = 7.86 Hz), 7.41-7.16 (8 H, m, overlapping with solvent peak), 3.57 (1 H, t, J = 12.71 Hz), 3.40 (1 H, td, J = 12.72, 3.70 Hz), 3.27 (1 H, dd, J = 16.61, 4.79 Hz), 3.13 (1 H, dt, J = 12.63, 4.15 Hz), 2.87 (1 H, dd, J = 16.61, 11.56 Hz), 2.47 (1 H, td, J = 13.48, 4.22 Hz), 2.34 (1 H, d, J = 13.05 Hz), 2.22 (1 H, dt, J = 14.23, 3.87 Hz), 1.93 (1 H, t, J = 13.00 Hz). No NH₂ peak observed. (white solid) |
| 44 HCl salt | 497 | 3.32[e] | ¹H NMR δ (ppm)(DMSO-d₆): 10.60 (1 H, s), 7.95 (2 H, d, J = 11.94 Hz), 7.75 (2 H, d, J = 8.53 Hz), 7.61 (2 H, dd, J = 7.51, 4.78 Hz), 7.53 (1 H, t, J = 7.65 Hz), 7.43 (4 H, d, J = 4.34 Hz), 7.39-7.29 (1 H, m), 7.11 (2 H, d, J = 8.53 Hz), 3.87 (3 H, s), 3.62-3.51 (1 H, m), 3.47-3.30 (1 H, m, underneath water peak), 3.26-3.18 (1 H, m), 3.01-2.91 (1 H, sm), 2.78-2.66 (1 H, m), 2.42-2.37 (3 H, dd, J = 26.26, 13.32 Hz), 2.22-2.14 (1 H, m). No NH₂ peak observed. (beige solid) |

[a-f]Rt refers to HPLC method A to F

For Examples 43 and 44, on Step 5 of Method 4, only one diastereoisomer was isolated as a racemic mixture.

Example 45

3-(2'-amino-6-(methoxymethyl)-5',6,6',7-tetrahydro-5H-spiro[benzo[b]thiophene-4,4'-[1,3]thiazine]-2-yl)benzonitrile, Hydrochloride Salt

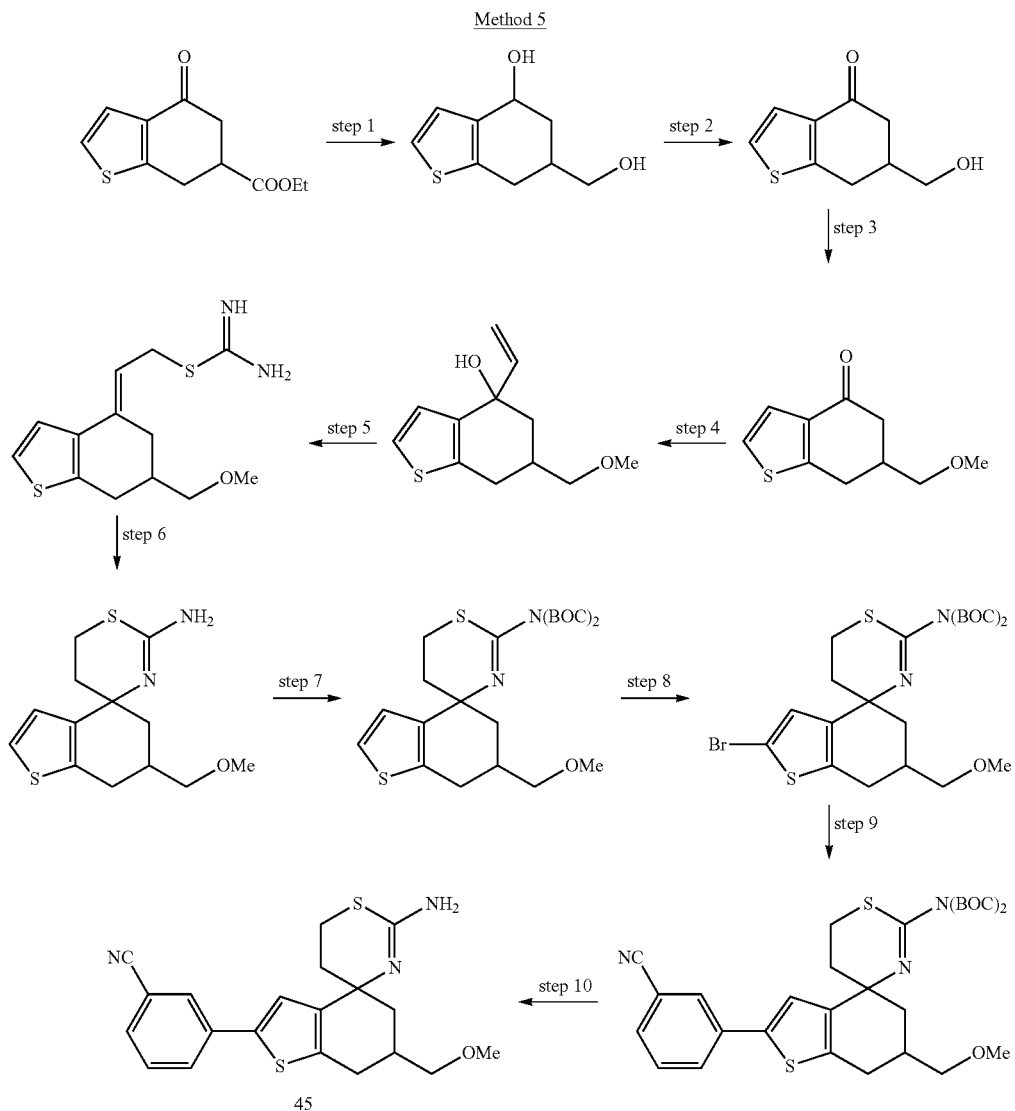

Method 5

Step 1: 6-(hydroxymethyl)-4,5,6,7-tetrahydrobenzo[b]thiophen-4-ol

Ethyl-4-oxo-4,5,6,7-tetrahydrobenzo[b]thiophene-6-carboxylate (1.5 g, 6.7 mmol) was dissolved in EtOH (20 mL). 1M NaOH (aq.) (7 mL) was added portion-wise and the mixture was stirred at room temperature for 1 hr 45 min. The mixture was concentrated in vacuo and the residue was treated with 2M HCl (aq.). The product was extracted into ethyl acetate (×3) and this was back extracted with water and saturated brine. The organic extracts were combined, dried (MgSO₄) and concentrated in vacuo to yield crude 4-oxo-4,5,6,7-tetrahydrobenzo[b]thiophene-6-carboxylic acid (1.27 g, 100%). This was dissolved in THF (15 mL) and BH₃.DMS (4.8 mL, 2M in THF, 8.7 mmol) was added drop-wise at 0° C. The mixture was warmed to room temperature and stirred for 18 hr. Methanol was added and the reaction mixture was concentrated in vacuo. The crude residue was dissolved in ethyl acetate and washed with 1M NaOH (aq.) solution, water and brine. The organic extract was dried (MgSO₄) and concentrated in vacuo to give the title compound (1.2 g, quant.).

Step 2: 6-(hydroxymethyl)-6,7-dihydrobenzo[b]thiophen-4(5H)-one 6-(Hydroxymethyl)-4,5,6,7-tetrahydrobenzo[b]thiophen-4-ol (1.2 g, 6.7 mmol) was dissolved in 1,4-dioxane (30 mL) and manganese dioxide (5.8 g, 67 mmol) was added portion-wise at room temperature. The mixture was stirred for 1 h 40 min. The solution was filtered through celite, washed with 1,4-dioxane and concentrated in vacuo. The crude residue was purified on silica gel using a gradient elution of 40-60% ethyl acetate in 40-60 petroleum ether to yield the title compound as a yellow oil (0.745 g, 62%).

Step 3:
6-(methoxymethyl)benzo[b]thiophen-4(7H)-one

Sodium hydride (60% dispersion in mineral oil, 0.2 g, 5 mmol), was washed with hexane and then suspended in THF (6 mL) under a nitrogen atmosphere at 0° C. 6-(Hydroxymethyl)-6,7-dihydrobenzo[b]thiophen-4(5H)-one (0.745 g, 4.1 mmol) was dissolved in THF (4 mL) and added drop-wise to the sodium hydride suspension. After 10 min methyl iodide (0.71 g, 0.31 mL, 5 mmol) was added and the reaction mixture was warmed to room temperature and stirred for 3 hr. Water and saturated brine solution (2 mL, 1:1) were added and the product was extracted into dichloromethane (×3). The organic layers were combined, dried (MgSO₄) and concentrated in vacuo. The crude residue was purified on silica gel using a gradient elution of 0-50% ethyl acetate in iso-hexane to afford the title compound (0.109 g, 34%).

Steps 4-10: 3-(2'-amino-6-(methoxymethyl)-5',6,6',7-tetrahydro-5H-spiro[benzo[b]thiophene-4,4'-[1,3]thiazine]-2-yl)benzonitrile, Hydrochloride Salt 3-(2'-Amino-6-(methoxymethyl)-5',6,6',7-tetrahydro-5H-spiro[benzo[b]thiophene-4,4'-[1,3]thiazin]-2-yl)benzonitrile was synthesised from 6-(methoxymethyl)benzo[b]thiophen-4(7H)-one following the procedures outlined in Method 1, steps 1-7 to yield the title compound as the HCl salt (5.7 mg). In Step 6, only one diastereoisomer was isolated as a racemic mixture as yellow solid. ¹H NMR δ (ppm) (CH₃OH-d₄): 8.06 (1H, s), 7.97 (1H, d, J=7.94 Hz), 7.74-7.60 (3H, m), 3.63 (1H, dd, J=13.21, 3.89 Hz), 3.59-3.49 (2H, m), 3.46 (3H, s), 3.44-3.39 (1H, m, overlapping with solvent peak), 3.14 (1H, dd, J=16.75, 4.63 Hz), 2.81-2.59 (2H, m), 2.39 (3H, t, J=13.47 Hz), 1.68 (1H, t, J=13.25 Hz). No NH2 peak observed. LCMS (Method d) Rt 3.13 (min) m/z 384 (MH⁺).

Example 46

5,5-dimethyl-2-(3-(trifluoromethyl)phenyl)-5',6,6',7-tetrahydro-5H-spiro[benzo[b]thiophene-4,4'-[1,3]thiazin]-2'-amine

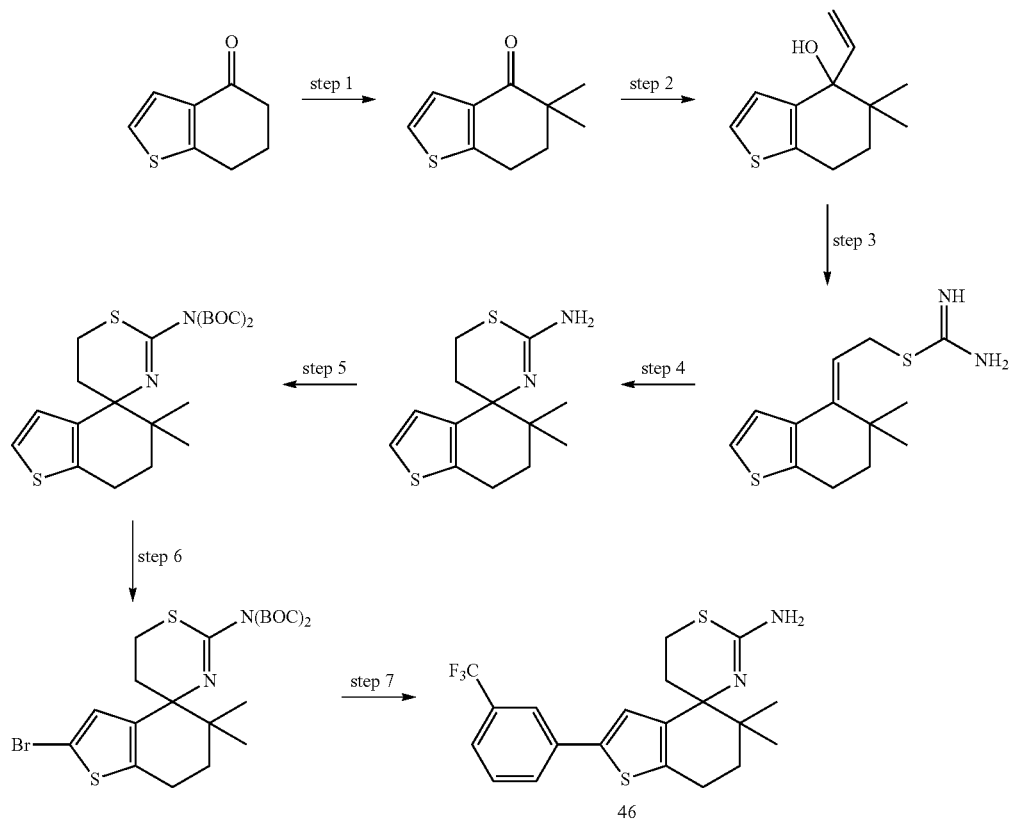

Step 1:
5,5-dimethyl-6,7-dihydrobenzo[b]thiophen-4(5H)-one 6,7-Dihydrobenzo[b]thiophen-4(5H)-one (1.0 g, 6.6 mmol) in toluene (10 mL) was added drop-wise to NaH (60% dispersion in mineral oil, 1.32 g, 32.9 mmol) in toluene (5 mL). DMF (5 mL) was added and the reaction was stirred at room temperature for 1 hr. The mixture was cooled to 0° C., methyl iodide (4.67 g, 2.1 mL, 32.9 mmol) was added drop-wise and the solution was refluxed for 3 h. The mixture was cooled and carefully treated with iso-propanol. The product was extracted into diethyl ether (×3) and this was back extracted with water and saturated brine. The diethyl ether solution was dried (MgSO₄), filtered and concentrated in vacuo. The crude residue was purified on silica gel using a gradient elution of 0-75% ethyl acetate in 40-60 petroleum ether to afford the title compound as a yellow oil (0.375 g, 32%).

Steps 2-7: 5,5-dimethyl-2-(3-(trifluoromethyl)phenyl)-5',6,6',7-tetrahydro-5H-spiro[benzo[b]thiophene-4,4'-[1,3]thiazin]-2'-amine 5,5-Dimethyl-2-(3-(trifluoromethyl)phenyl)-5',6,6',7-tetrahydro-5H-spiro[benzo[b]thiophene-4,4'-[1,3]thiazin]-2'-amine was synthesised from 5,5-dimethyl-6,7-dihydrobenzo[b]thiophen-4(5H)-one following the procedures outlined in Method 1, steps 1-7 to afford the title compound as beige gum (3.7 mg). $^1$H NMR δ (ppm)(CHCl$_3$-d): 7.75 (1H, s), 7.73-7.67 (1H, m), 7.50-7.42 (2H, m), 7.08 (1H, s), 3.15-3.06 (1H, m), 3.00-2.78 (3H, m), 2.11-1.99 (2H, m), 1.98-1.87 (1H, m), 1.72 (1H, ddd, J=13.93, 7.00, 2.17 Hz), 1.08 (3H, s), 0.99 (3H, s). No NH2 peak observed. LCMS (Method e) Rt 3.04 (min) m/z 411 (MH$^+$).

Example 47

3-(2'-amino-5-benzyl-5',6,6',7-tetrahydro-5H-spiro[benzo[b]thiophene-4,4'-[1,3]thiazine]-2-yl)benzonitrile re-cooled to −78° C. Benzyl bromide (1.17 mL, 9.9 mmol) was then added drop-wise and the mixture was gradually warmed to room temperature and stirred for 18 hr. Saturated ammonium chloride solution was added to the reaction mixture and product was extracted into ethyl acetate (×3). The combined organic extracts were combined, dried (MgSO$_4$) and concentrated in vacuo. The crude residue was purified on silica gel using a gradient elution of 0-50% ethyl acetate in iso-hexane to afford the title compound as a yellow oil (0.55 g, 62%).

Steps 2-8: 3-(2'-amino-5-benzyl-5',6,6',7-tetrahydro-5H-spiro[benzo[b]thiophene-4,4'-[1,3]thiazine]-2-yl)benzonitrile 3-(2'-Amino-5-benzyl-5',6,6',7-tetrahydro-5H-spiro[benzo[b]thiophene-4,4'-[1,3]thiazine]-2-yl)benzonitrile was synthesised from 5-benzyl-6,7-dihydrobenzo[b]thiophen-4(5H)-one following the procedures outlined in Method 1, steps 1-7 to yield the title compound (60 mg). In Step 4, only one diastereoisomer was isolated as a racemic mixture as yellow foam. $^1$H NMR δ (ppm)(CHCl$_3$-d): 7.79 (1H, s), 7.72 (1H, d, J=7.88 Hz), 7.51 (1H, d, J=7.70 Hz), 7.44 (1H, t, J=7.92 Hz), 7.32-7.15 (5H, m, overlapping with sol-

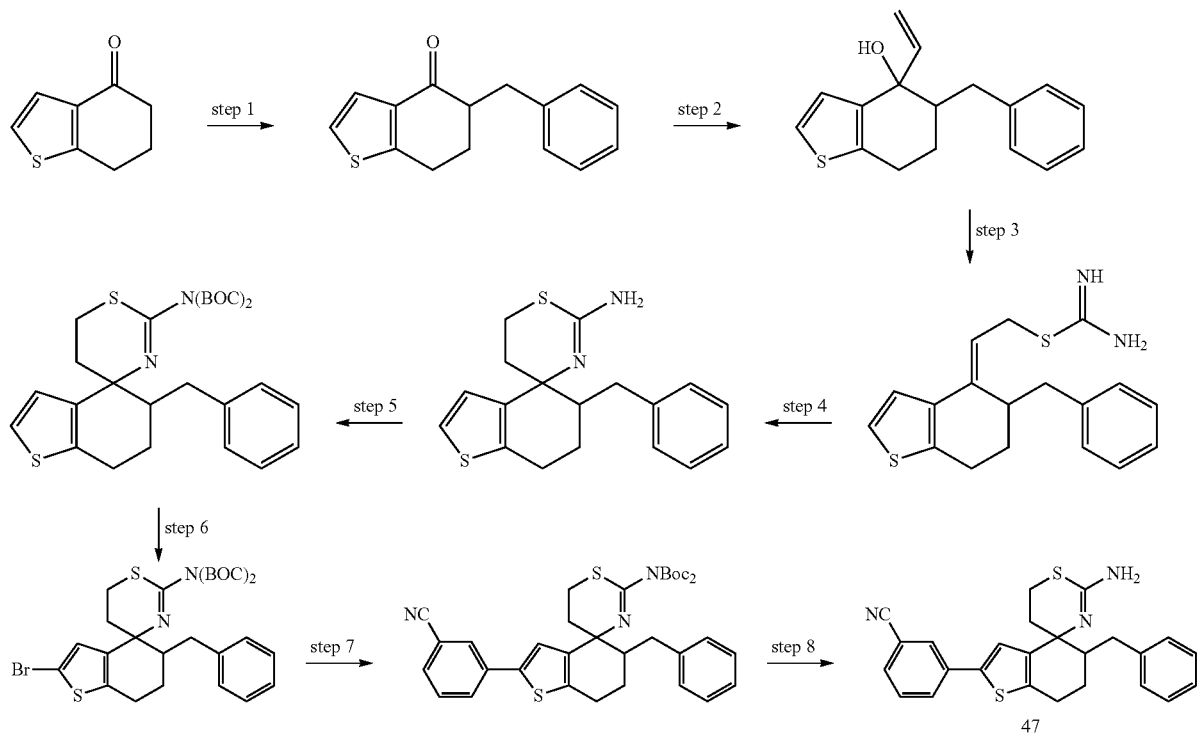

Method 7

Step 1:
5-benzyl-6,7-dihydrobenzo[b]thiophen-4(5H)-one 6,7-Dihydrobenzo[b]thiophen-4(5H)-one (0.5 g, 3.3 mmol) in THF (7.5 mL) was added drop-wise to LDA (2.2 mL, 3.67 mmol) under a nitrogen atmosphere at −78° C. The mixture was warmed to −30° C. for 10 min before being vent peak), 7.11 (1H, s), 3.23 (1H, t, J=12.62 Hz), 3.01 (2H, d, J=11.07 Hz), 2.86 (1H, dd, J=17.67, 6.12 Hz), 2.81-2.68 (1H, m), 2.29-2.14 (2H, m), 2.10 (1H, d, J=13.69 Hz), 2.02-1.81 (3H, m). No NH2 peak observed. HPLC (Method a) Rt 8.19 (min) m/z 430 (MH$^+$).

Similarly prepared using Method 7 and 1-bromomethyl-4-methoxy-benzene in the first step was:

| Structure | MH+ | HPLC Rt | NMR |
|---|---|---|---|
| 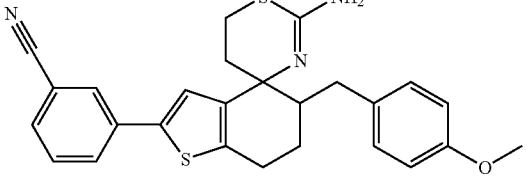<br>48 formate salt | 460 | 8.17[a] | $^1$H NMR δ (ppm)(CHCl$_3$-d): 8.63 (1 H, s), 7.84-7.70 (2 H, m), 7.56-7.42 (2 H, m), 7.31-7.24 (2 H, m, overlapping with solvent peak), 7.18-7.07 (1 H, m), 6.86 (2 H, d, J = 7.95 Hz), 3.80 (3 H, s), 3.32 (1 H, t, J = 12.63 Hz), 3.04 (2 H, t, J = 10.68 Hz), 2.88-2.70 (2 H, m), 2.49 (1 H, t, J = 12.18 Hz), 2.36-2.12 (3 H, m), 2.01 (1 H, d, J = 13.51 Hz), 1.78-1.64 (1 H, m). No NH$_2$ peak observed. (white foam) |

[a-f]Rt refers to HPLC method A to F

For Example 48, on Step 4 of Method 7, only one diastereoisomer was isolated as a racemic mixture.

Preparation of 2'-amino-1'-methyl-6,7-dihydro-5H-spiro[benzo[b]thiophene-4,4'-imidazol]-5'(1'H)-one Method 8:

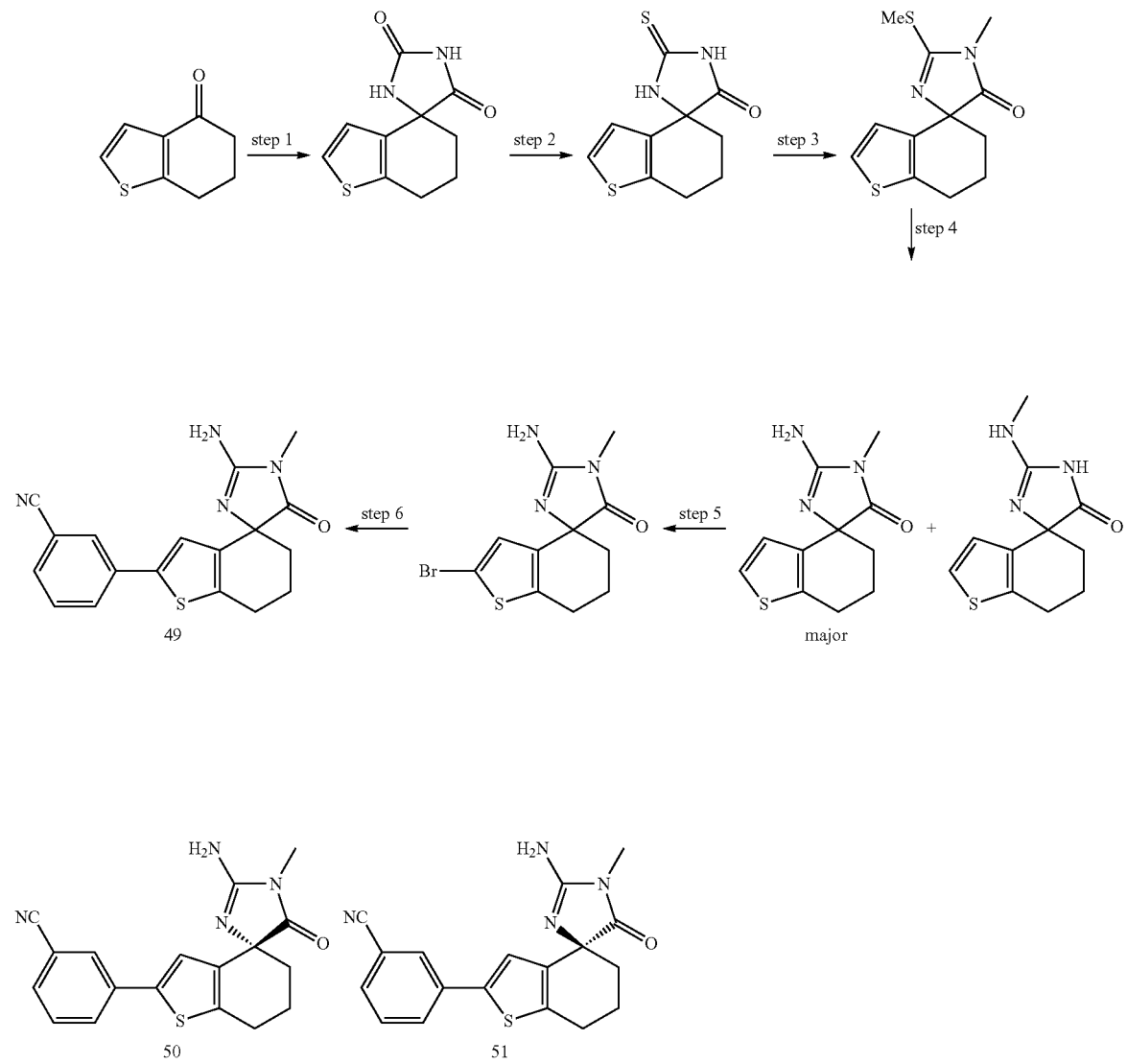

Step 1: 6,7-dihydro-5H-spiro[benzo[b]thiophene-4, 4'-imidazolidine]-2',5'-dione

50% Aqueous EtOH (35 mL) was added to 6,7-dihydrobenzo[b]thiophen-4(5H)-one (1.0 g, 6.5 mmol), KCN (0.85 g, 13 mmol) and $(NH_4)_2CO_3$ (5.36 g, 55 mmol) in a large reaction tube. The tube was sealed and heated at 80° C. for 24 hr. The mixture was cooled and poured into ice-water (100 mL). The solution was acidified using conc. aq. HCl and a solid precipitate formed. The precipitate was collected by filtration, washed with water and dried in vacuo to afford the title compound (1.33 g, 91%).

Step 2: 2'-thioxo-6,7-dihydro-5H-spiro[benzo[b]thiophene-4,4'-imidazolidin]-5'-one 6,7-Dihydro-5H-spiro[benzo[b]thiophene-4,4'-imidazolidine]-2',5'-dione (0.5 g, 2.25 mmol) and 2,4-bis(4-methoxyphenyl)-1,3,2,4-dithiadiphosphetane-2,4-disulfide (Lawesson's reagent) (0.91 g, 2.25 mmol) were suspended in 1,4-dioxane (5 mL). The mixture was heated by microwave irradiation at 120° C. for 30 min. The solution was concentrated in vacuo and the crude residue purified on silica gel using a gradient elution of 20-100% ethyl acetate in 40-60 petroleum ether. Isolated material was further purified on silica gel using a gradient elution of 2-5% methanol in dichloromethane to afford the title compound as a colourless solid (0.54 g, 100%).

Step 3: 1'-methyl-2'-(methylthio)-6,7-dihydro-5H-spiro[benzo[b]thiophene-4,4'-imidazol]-5'(1'H)-one 2'-Thioxo-6,7-dihydro-5H-spiro[benzo[b]thiophene-4,4'-imidazolidin]-5'-one (0.192 g, 0.86 mmol) was dissolved in methanol (16 mL). Methyl iodide (1.83 g, 0.8 mL, 12.9 mmol) and NaOH (aq.) (3.22 mL, 0.6 M, 1.93 mmol) were added and the mixture was heated by microwave irradiation at 60° C. for 10 min. The solution was concentrated in vacuo and the crude residue purified on silica gel using a gradient elution of 20-100% ethyl acetate in iso-hexane to afford the title compound as an off-white solid (0.26 g, 100%).

Step 4: 2'-amino-1'-methyl-6,7-dihydro-5H-spiro[benzo[b]thiophene-4,4'-imidazol]-5'(1'H)-one 1'-Methyl-2'-(methylthio)-6,7-dihydro-5H-spiro[benzo[b]thiophene-4,4'-imidazol]-5'(1'H)-one (1.5 g, 5.63 mmol), ammonium iodide (4.89 g, 33.78 mmol) and 7 N ammonia in methanol (20 mL) were heated at 90° C. for 12 h. The solvent was then evaporated under reduced pressure and the residue was partitioned between water and dichloromethane. The dichloromethane extracts were combined, dried over magnesium sulphate and evaporated under reduced pressure to give an oil. This consisted of the title compound as the major component and its minor regioisomer in a 2:1 ratio. The oil was loaded onto a Biotage SNAP cartridge and eluted with dichloromethane-dichloromethane/7N ammonia in methanol (9:1). The appropriate fractions were combined and evaporated under reduced pressure to give 2'-amino-1'-methyl-6,7-dihydro-5H-spiro[benzo[b]thiophene-4,4'-imidazol]-5'(1'H)-one as a foam (800 mg, 60%).

Step 5: 2'-amino-2-bromo-1'-methyl-6,7-dihydro-5H-spiro[benzo[b]thiophene-4,4'-imidazol]-5'(1'H)-one 2'-amino-1'-methyl-6,7-dihydro-5H-spiro[benzo[b]thiophene-4,4'-imidazol]-5'(1'H)-one (75 mg, 0.32 mmol) was dissolved in acetic acid (0.5 mL) and water (0.5 mL). The mixture was cooled to 0° C. and bromine (51 mg, 0.016 mL, 0.32 mmol) was added drop-wise. After 20 min at 0° C. the reaction was warmed to room temperature and stirred for 1 hr. Solvent was removed in vacuo to afford a yellow oil which solidified on standing. The residue was suspended in dichloromethane and treated with 7 N $NH_3$/MeOH solution yielding a precipitate that was removed by filtration. The organic mother liquor was concentrated in vacuo and the crude residue purified on silica gel using a gradient elution of 2-10% 7 N $NH_3$/methanol in dichloromethane to afford the title compound as the formate salt as a pale yellow foam (0.285 g, 95%). $^1$H NMR δ (ppm)(DMSO-d$^6$): 8.22 (1H, s), 6.71 (1H, s), 3.01-2.95 (3H, m), 2.77-2.65 (2H, m), 2.11-2.04 (1H, m), 1.87 (2H, t, J=9.50 Hz), 1.76-1.68 (1H, m). No NH2 peak observed. HPLC (Method c) Rt 8.77 (min) m/z 314 (MH$^+$).

Step 6: 3-(2'-amino-1'-methyl-5'-oxo-1',5',6,7-tetrahydro-5H-spiro[benzo[b]thiophene-4,4'-imidazole]-2-yl)benzonitrile 2'-amino-2-bromo-1'-methyl-6,7-dihydro-5H-spiro[benzo[b]thiophene-4,4'-imidazol]-5'(1'H)-one (0.127 g, 0.4 mmol), 3-cyanophenyl boronic acid (59 mg, 0.4 mmol) and Pd(dppf)Cl$_2$ (33 mg, 0.04 mmol), were suspended in DMF (1.5 mL). $Cs_2CO_3$ (0.35 mL, 3.7 M aq. solution, 1.29 mmol) was added and the solution was degassed under a stream of nitrogen for 10 min. The mixture was heated at 90° C. for 2 hr. The reaction was cooled and solvent was removed in vacuo. The crude residue was purified using preparative HPLC to give the title compound as off-white solid (14 mg, 11%). $^1$H NMR δ (ppm)(DMSO-d$^6$): 8.11 (1H, s), 7.86 (1H, d, J=8.18 Hz), 7.71 (1H, d, J=7.72 Hz), 7.57 (1H, t, J=7.85 Hz), 7.14 (1H, s), 6.41 (2H, br s), 3.02 (3H, s), 2.84-2.76 (2H, m), 2.11 (1H, d, J=13.56 Hz), 1.91 (2H, s), 1.70 (1H, s). HPLC (Method c) Rt 9.2 (min) m/z 337 (MH$^+$).

Examples 50 and 51

(R)-3-(2'-amino-1'-methyl-5'-oxo-1',5',6,7-tetrahydro-5H-spiro[benzo[b]thiophene-4,4'-imidazole]-2-yl)benzonitrile (3.7 mg) and (S)-3-(2'-amino-1'-methyl-5'-oxo-1',5',6,7-tetrahydro-5H-spiro[benzo[b]thiophene-4,4'-imidazole]-2-yl)benzonitrile Example 49 was purified by chiral preparative HPLC to give Example 50, (R)-3-(2'-amino-1'-methyl-5'-oxo-1',5',6,7-tetrahydro-5H-spiro[benzo[b]thiophene-4,4'-imidazole]-2-yl)benzonitrile as off-white solid (3.7 mg) and Example 51, (S)-3-(2'-amino-1'-methyl-5'-oxo-1',5',6,7-tetrahydro-5H-spiro[benzo[b]thiophene-4,4'-imidazole]-2-yl)benzonitrile as off-white solid (3.3 mg). Configurations were arbitrarily assigned.

Example 50

(R)-enantiomer: $^1$H NMR δ (ppm)(CH$_3$OH-d$^4$): 6.38 (1H, s), 6.30 (1H, dt, J=7.89, 1.53 Hz), 6.08-5.95 (2H, m), 5.50 (1H, s), 1.61 (3H, s), 1.39-1.31 (2H, m), 0.78-0.70 (1H, m), 0.56-0.47 (2H, m), 0.38-0.30 (1H, m). No NH$_2$ peak observed. HPLC (Method a) Rt 7.56 (min) m/z 337 (MH$^+$).

Example 51

(S)-enantiomer: $^1$H NMR δ (ppm)(CH$_3$OH-d$^4$): 6.40-6.36 (1H, m), 6.30 (1H, dt, J=7.86, 1.51 Hz), 6.10-5.97 (2H, m), 5.50 (1H, s), 1.61 (3H, s), 1.38-1.31 (2H, m), 0.78-0.71 (1H, m), 0.56-0.47 (2H, m), 0.38-0.32 (1H, m). No NH2 peak observed. LCMS (Method e) Rt 2.67 (min) m/z 337 (MH$^+$).

Similarly prepared using Method 8 with different boronic acid or ester derivatives were:

| Structure | MH+ | HPLC Rt | NMR |
|---|---|---|---|
| 52 | 313 | 6.69[a] | 1H NMR δ (ppm) (DMSO-d6): 8.80 (1 H, d, J = 2.38 Hz), 8.46 (1 H, dd, J = 4.76, 1.51 Hz), 7.96 (1 H, dt, J = 8.04, 1.93 Hz), 7.40 (1 H, dd, J = 8.02, 4.77 Hz), 7.06 (1 H, s), 3.01 (3 H, s), 2.88-2.74 (2 H, m), 2.18-2.10 (1 H, m), 1.95-1.84 (2 H, m), 1.77-1.67 (1 H, m). No NH2 peak observed. (off-white solid) |
| 53 formate salt | 396 | 10.91[a] | 1H NMR δ (ppm) (CHCl3-d): 8.50 (1 H, s), 7.45-7.31 (3 H, m), 7.12-7.09 (1 H, m), 6.80 (1 H, s), 3.28-3.19 (3 H, m), 2.93-2.82 (2 H, m), 2.38-2.28 (1 H, m), 2.25-2.14 (1 H, m), 2.06-1.95 (2 H, m). No NH2 peak observed. (off-white solid) |
| 54 | 380 | 2.4[b] | 1H NMR δ (ppm) (DMSO-d6): 7.83 (2 H, s), 7.65-7.50 (2 H, m), 7.05 (1 H, s), 6.39 (2 H, s), 2.99 (3 H, s), 2.83-2.75 (2 H, m), 2.10 (1 H, s), 1.95-1.75 (2H, m), 1.66 (1 H, d, J = 9.74 Hz). (off-white solid) |
| 55 formate salt | 367 | 2.85[b] | 1H NMR δ (ppm) (DMSO-d6): 8.18 (1 H, s), 7.64 (1 H, t, J = 1.45 Hz), 7.33-7.30 (2 H, m), 7.17 (1 H, s), 3.83 (3 H, s), 3.01 (3 H, s), 2.86-2.71 (2 H, m), 2.14-2.03 (1 H, m), 1.87 (2 H, t, J = 9.60 Hz), 1.71 (1 H, t, J = 8.95 Hz). No NH2 peak observed. (off-white solid) |
| 56 formate salt | 346 | 2.35[b] | 1H NMR δ (ppm) (DMSO-d6): 8.18 (1 H, s), 7.64 (1 H, t, J = 1.89 Hz), 7.48 (1 H, dt, J = 7.79, 1.37 Hz), 7.37 (1 H, t, J = 9.2 Hz), 7.30 (1 H, ddd, J = 7.96, 2.05, 1.06 Hz), 7.07 (1 H, s), 3.00 (3 H, s), 2.81-2.74 (2 H, m), 2.09 (1 H, s), 1.88 (2 H, d, J = 9.66 Hz), 1.76-1.65 (1 H, m). No NH2 peak observed. (off-white solid) |

[a-f]Rt refers to HPLC method A to F

Example 57

3-(2'-amino-1'-benzyl-5'-oxo-1',5',6,7-tetrahydro-5H-spiro[benzo[b]thiophene-4,4'-imidazole]-2-yl)benzonitrile in a large reaction tube. The tube was sealed and heated at 80° C. for 18 hr. The mixture was cooled and poured into ice-water (100 mL). The solution was acidified using conc. aqueous HCl and a solid precipitate formed. The precipitate was collected by filtration, washed with water and dried in vacuo to afford the title compound (1.1 g, 81%).

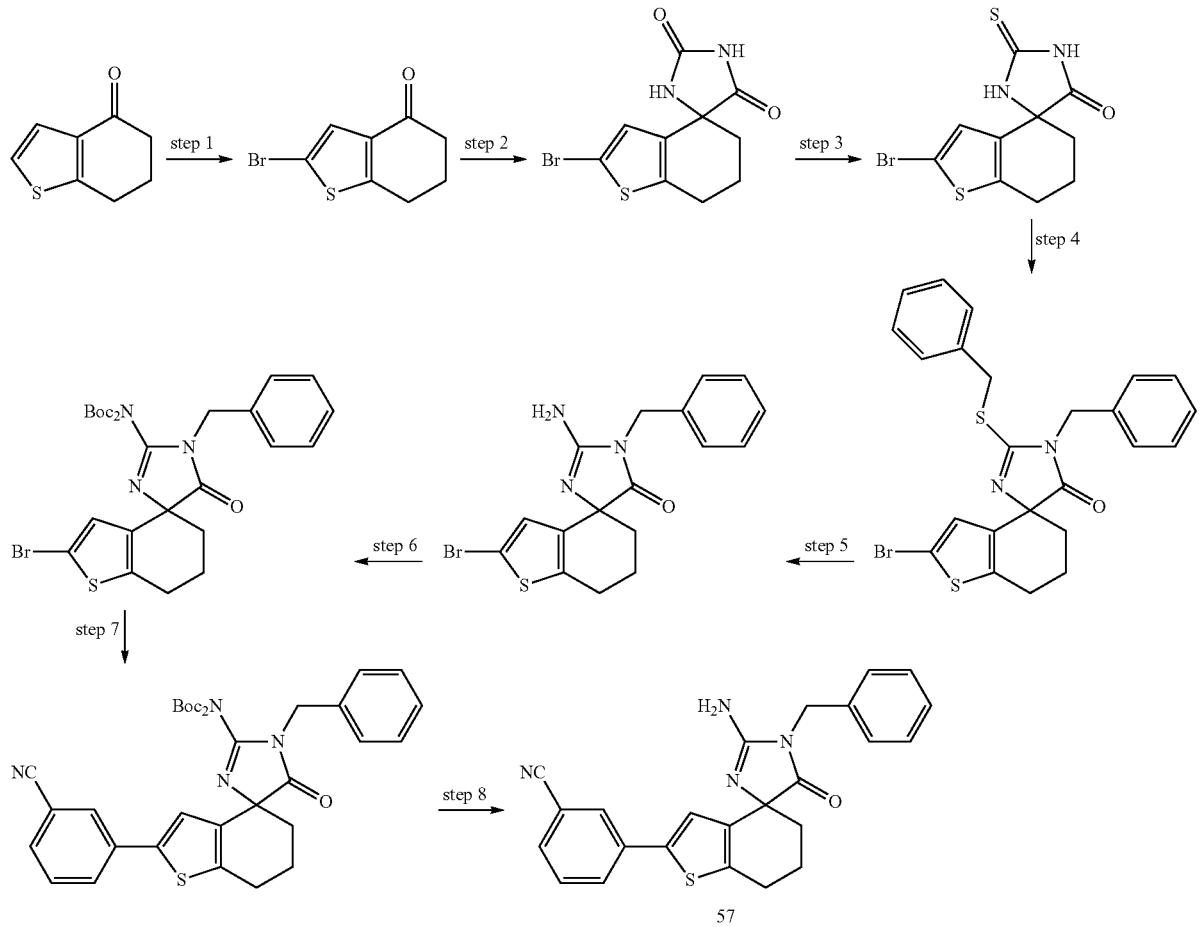

Step 1: 2-bromo-6,7-dihydrobenzo[b]thiophen-4(5H)-one 6,7-Dihydro-4-Benzo[B]thiophenone (1.5 g, 9.86 mmol) was dissolved in acetic acid (10 mL) and water (10 mL). The mixture was cooled to 0° C. and bromine (0.51 mL, 9.86 mmol) was added drop-wise. After 20 min at 0° C. the reaction was warmed to room temperature and stirred for 18 hr. The reaction mixture was cooled in ice and then treated with 1 M aqueous sodium hydroxide solution until the mixture was basic. A precipitate formed which was collected by filtration, washed with water and dried in a vacuum oven at 50° C. to afford the title compound as a grey solid (2.1 g, 96%).

Step 2: 2-bromo-6,7-dihydro-5H-spiro[benzo[b]thiophene-4,4'-imidazolidine]-2',5'-dione 50% Aqueous EtOH (20 mL) was added to 2-bromo-6,7-dihydrobenzo[b]thiophen-4(5H)-one (1.0 g, 4.5 mmol), KCN (0.586 g, 9 mmol) and $(NH_4)_2CO_3$ (3.68 g, 38.2 mmol)

Step 3: 2-bromo-2'-thioxo-6,7-dihydro-5H-spiro[benzo[b]thiophene-4,4'-imidazolidin]-5'-one 2-Bromo-6,7-dihydro-5H-spiro[benzo[b]thiophene-4,4'-imidazolidine]-2',5'-dione (0.5 g, 1.67 mmol) and 2,4-bis(4-methoxyphenyl)-1,3,2,4-dithiadiphosphetane-2,4-disulfide (Lawesson's reagent) (0.371 g, 0.91 mmol) were suspended in 1,4-dioxane (5 mL). The mixture was heated by microwave irradiation at 110° C. for 2×30 min. The solution was concentrated in vacuo and the crude residue purified on silica gel using ethyl acetate in 40-60 petroleum ether (1:1) to afford the title compound as a colourless solid (0.28 g, 53%).

Step 4: 1'-benzyl-2'-(benzylthio)-2-bromo-6,7-dihydro-5H-spiro[benzo[b]thiophene-4,4'-imidazol]-5'(1'H)-one 2-Bromo-2'-thioxo-6,7-dihydro-5H-spiro[benzo[b]thiophene-4,4'-imidazolidin]-5'-one (0.285 g, 0.9 mmol) was dissolved in THF (20 mL) and cooled to 0° C. in an ice bath.

Sodium hydride (50% dispersion in oil, 26 mg, 1.08 mmol) was added and the mixture was stirred for 15 min. Benzyl bromide (0.13 ml, 1.08 mmol) was added and the reaction mixture was stirred at room temperature for 1 h. The mixture was cooled to 0° C. again and a further portion of sodium hydride (50% dispersion in oil, 26 mg, 1.08 mmol) was added. The mixture was stirred for 15 min, benzyl bromide (0.13 mL, 1.08 mmol) was added and the reaction mixture was stirred at room temperature for 18 hr. Solvent was evaporated under reduced pressure. The residue was dissolved in water and extracted with dichloromethane (×3). The organic extracts were combined, dried (MgSO$_4$), and concentrated in vacuo. The crude residue purified on silica gel using ethyl acetate in iso-hexane (1:1) to afford the title compound as a colourless oil (0.25 g, 56%).

Step 5: 2'-amino-1'-benzyl-2-bromo-6,7-dihydro-5H-spiro[benzo[b]thiophene-4,4'-imidazol]-5'(1'H)-one 1'-Benzyl-2'-(benzylthio)-2-bromo-6,7-dihydro-5H-spiro[benzo[b]thiophene-4,4'-imidazol]-5'(1'H)-one (0.25 g, 0.5 mmol) and ammonium iodide (0.43 g, 3 mmol) were suspended in 7 N NH$_3$/methanol solution (10 mL). The mixture was heated at 90° C. for 18 hr. The solution was concentrated in vacuo and the crude residue partitioned between water and dichloromethane. The product was extracted into dichloromethane (×3), the organic extracts were combined, dried (MgSO$_4$) and concentrated in vacuo. The crude residue was purified on silica gel using 7 N NH$_3$/methanol in dichloromethane (1:9) to afford the title compound as a foam (80 mg, 41%).

Step 6: di-tert-butyl 1'-benzyl-2-bromo-5'-oxo-1',5',6,7-tetrahydro-5H-spiro[benzo[b]thiophene-4,4'-imidazole]-2'-yliminodicarbonate The title compound was prepared according to Method 1, step 7. It was used without further purification.

Step 7: di-tert-butyl 1'-benzyl-2-(3-cyanophenyl)-5'-oxo-1',5',6,7-tetrahydro-5H-spiro[benzo[b]thiophene-4,4'-imidazole]-2'-ylcarbamate Di-tert-butyl 1'-benzyl-2-bromo-5'-oxo-1',5',6,7-tetrahydro-5H-spiro[benzo[b]thiophene-4,4'-imidazole]-2'-yliminodicarbonate (80 mg, 0.14 mmol), 3-cyanophenyl boronic acid (30 mg, 0.2 mmol) and Na$_2$CO$_3$ (0.2 mL, 2M aq. solution, 0.4 mmol) were suspended in 1,4-dioxane (4 mL). The solution was degassed under a stream of nitrogen for 10 min Pd(dppf)Cl$_2$ (11 mg, 0.013 mmol) was added and the mixture was heated at 100° C. for 18 hr. The reaction was cooled and poured into water. The product was extracted with ethyl acetate (×3). The organic layers were combined, dried (MgSO$_4$) and concentrated in vacuo. The crude residue was used directly in the next step without further purification.

Step 8: 3-(2'-amino-1'-benzyl-5'-oxo-1',5',6,7-tetrahydro-5H-spiro[benzo[b]thiophene-4,4'-imidazole]-2-yl)benzonitrile Di-tert-butyl 1'-benzyl-2-(3-cyanophenyl)-5'-oxo-1',5',6,7-tetrahydro-5H-spiro[benzo[b]thiophene-4,4'-imidazole]-

2'-ylcarbamate (0.13 mmol) was stirred in dichloromethane (1 mL) and trifluoroacetic acid (1 mL) for 18 hr at room temperature.

The reaction was evaporated in vacuo to leave a residue that was dissolved in dichloromethane. The organic layer was washed with sat. Na$_2$CO$_3$ (aq.) solution. The organic extracts were combined, dried (MgSO$_4$) and concentrated in vacuo. The crude residue was purified using preparative HPLC to give the title compound as off-white solid and as formate salt (21.4 mg, 38%). $^1$H NMR δ (ppm)(DMSO-d$^6$): 8.18 (1H, s), 7.89 (1H, t, J=1.72 Hz), 7.75-7.69 (2H, m), 7.56 (1H, t, J=7.83 Hz), 7.40-7.28 (5H, m), 6.86 (1H, s), 4.74 (2H, q, J=7.38 Hz), 2.82-2.72 (2H, m), 2.15-2.04 (1H, m), 1.91 (2H, d, J=9.98 Hz), 1.76 (1H, t, J=9.53 Hz). HPLC (Method a) Rt 7.91 (min) m/z 413 (MH$^3$).

Example 58

2'-methyl-2-(3-(trifluoromethyl)phenyl)-6,7-dihydro-2'H,5H-spiro[benzo[b]thiophene-4,5'-[1,2,4]oxadiazol]-3'-amine

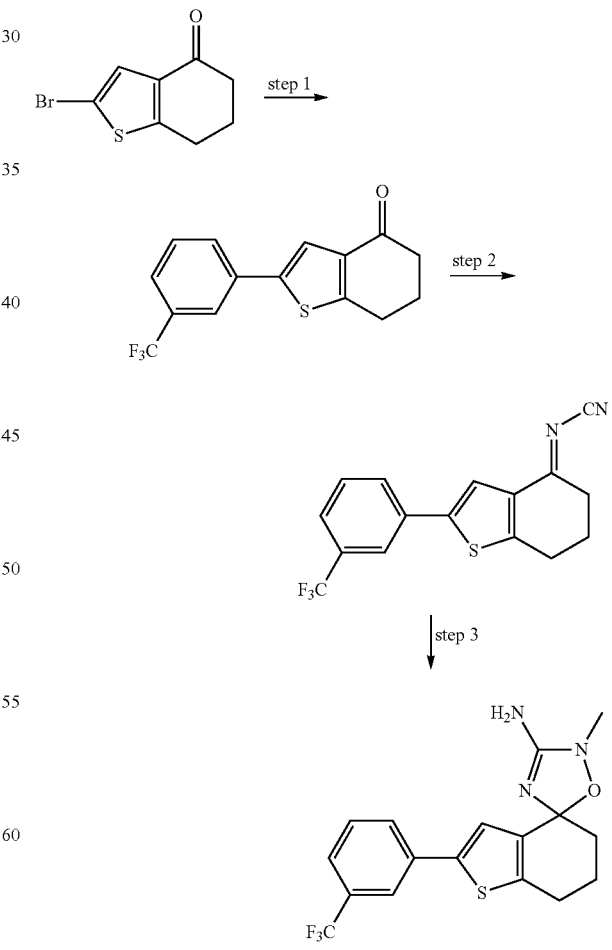

Method 10

58

Step 1: 2-(3-(trifluoromethyl)phenyl)-6,7-dihydrobenzo[b]thiophen-4(5H)-one

2-Bromo-6,7-dihydrobenzo[b]thiophen-4(5H)-one (0.118 g, 0.48 mmol), 3-trifluoromethyl boronic acid (0.137 g, 0.72 mmol) and $Cs_2CO_3$ (0.313 g, 0.96 mmol) were suspended in 1,4-dioxane (5 mL) and water (0.5 mL). The solution was degassed under a stream of nitrogen for 10 min $Pd(PPh_3)_2Cl_2$ (17 mg, 0.024 mmol) was added and the mixture was heated by microwave irradiation at 110° C. for 30 min. The reaction was cooled and poured into water. The product was extracted with dichloromethane (×3). The organic layers were combined, dried ($MgSO_4$) and concentrated in vacuo. The crude residue purified on silica gel using ethyl acetate in iso-hexane (1:3) to afford the title compound as a solid (93 mg, 65%).

Step 2: (E)-N-(2-(3-(trifluoromethyl)phenyl)-6,7-dihydrobenzo[b]thiophen-4(5H)-ylidene)cyanamide 2-(3-(Trifluoromethyl)phenyl)-6,7-dihydrobenzo[b]thiophen-4(5H)-one (0.252 g, 0.85 mmol) was dissolved in dichloromethane (2 mL). Titanium tetrachloride (1.7 mL, 1.0 M solution in dichloromethane, 1.7 mmol) was added and the reaction mixture was stirred at room temperature for 1 hr. Bis-trimethylsilylcarbodiimide (0.42 mL, 1.87 mmol) was then added and the mixture was stirred at room temperature for 18 hr. The reaction mixture was poured onto ice/water and the product was extracted with dichloromethane. This was back extracted with water and saturated sodium carbonate (aq.) solution. The organic extracts were combined, dried ($MgSO_4$) and concentrated in vacuo to give the title compound as a cream solid (0.27 g, 99%).

Step 3: 2'-methyl-2-(3-(trifluoromethyl)phenyl)-6,7-dihydro-2'H,5H-spiro[benzo[b]thiophene-4,5'-[1,2,4]oxadiazol]-3'-amine To a solution of methylhydroxylamine hydrochloride (23 mg, 0.28 mmol) in methanol (2 mL) was added potassium carbonate (44 mg, 0.32 mmol) followed by (E)-N-(2-(3-(trifluoromethyl)phenyl)-6,7-dihydrobenzo[b]thiophen-4(5H)-ylidene)cyanamide (50 mg, 0.16 mmol). The reaction mixture was stirred at room temperature for 1 hr. The mixture was concentrated in vacuo and the crude residue partitioned between dichloromethane and water. The product was extracted into dichloromethane (×3). The organic extracts were combined, dried ($MgSO_4$) and concentrated under reduced pressure. The crude residue was purified using preparative HPLC to give the title compound as yellow solid (34.2 mg, 58%). (regioisomeric mix with 2'-methyl-2-(3-(trifluoromethyl)phenyl)-6,7-dihydro-2'H, 5H-spiro[benzo[b]thiophene-4,3'-[1,2,4]oxadiazol]-5'-amine). $^1$H NMR δ (ppm)(DMSO-d$^6$): 7.87-7.80 (2H, m), 7.64-7.58 (2H, m), 7.34 (1H, s), 6.12 (2H, s), 2.94 (3H, s), 2.80-2.60 (2H, m), 1.93-1.80 (3H, m), 1.80-1.69 (1H, m). HPLC (Method a) Rt 8.05 (min) m/z 368 (MH$^+$).

Similarly prepared using Method 10 and N-benzylhydroxylamine hydrochloride in step 3:

| Structure | MH+ | HPLC Rt | NMR |
|---|---|---|---|
| 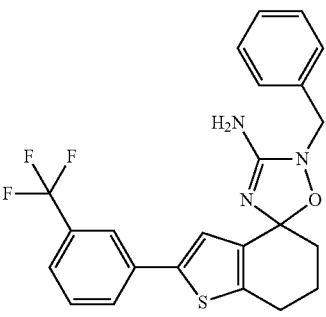 | 444 | 8.46[a] | $^1$H NMR δ (ppm)(CHCl$_3$-d): 7.71 (1 H, s), 7.63 (1 H, d, J = 7.47 Hz), 7.50-7.40 (4 H, m), 7.38-7.25 (3 H, m, overlapping with solvent peak), 6.88 (1 H, s), 4.44 (2 H, s), 4.17 (2 H, s), 2.84-2.67 (2 H, m), 2.06-1.96 (2 H, m), 1.95-1.87 (1 H, m), 1.86-1.78 (1 H, m). (off-white solid) |
| 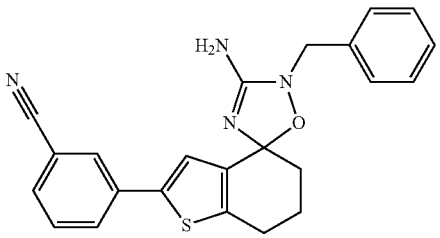 [SMILES: N#Cc1cccc(-c2cc3c(s2)CCCC32N=C(N)N(Cc3ccccc3)C2=O)c1] | 401 | 8.08[a] | $^1$H NMR δ (ppm)(CHCl$_3$-d): 7.74-7.73 (1 H, m) 7.67 (1 H, dt, J = 7.87, 1.51 Hz), 7.54-7.40 (4 H, m), 7.39-7.30 (3 H, m), 6.87 (1 H, s), 4.44 (2 H, s), 4.24 (2 H, s), 2.85-2.67 (2 H, m), 2.05-1.94 (2 H, m), 1.96-1.77 (2 H, m). (off-white solid) |

[a-f] Rt refers to HPLC method A to F

Similarly prepared using Method 1 and starting from 5,6-dihydrobenzo[b]thiophen-7(4H)-one and diverse boronic acid or ester derivatives were:

Compounds with activity in the LanthaScreen™ BACE-1 biochemical assay were progressed for testing in the HTRF cell based assay.

| Structure | MH+ | Rt | NMR |
|---|---|---|---|
| 61 formate salt | 391 | 8.26$^a$ | $^1$H NMR δ (ppm)(CHCl$_3$-d): 8.58 (1 H, s), 7.83 (1 H, s), 7.72-7.67 (2 H, m), 7.63-7.40 (5 H, m), 7.34 (1 H, s), 7.13 (1 H, s), 3.45-3.37 (1 H, m), 3.27 (1 H, ddd, J = 12.77, 8.67, 3.64 Hz), 2.89 (1 H, dt, J = 16.68, 6.75 Hz), 2.71 (1 H, dt, J = 16.54, 5.66 Hz), 2.53-2.44 (1 H, m), 2.38-2.11 (3 H, m), 1.99 (2 H, t, J = 9.98 Hz). No NH$_2$ peak observed. (off-white solid) |
| 62 formate salt | 340 | 7.59$^a$ | $^1$H NMR δ (ppm)(CHCl$_3$-d): 8.46 (1 H, s), 7.81 (1 H, t, J = 1.68 Hz), 7.76 (1 H, dt, J = 7.89, 1.49 Hz), 7.54 (1 H, dt, J = 7.72, 1.37 Hz), 7.46 (1 H, t, J = 7.79 Hz), 7.05 (1 H, s), 3.37-3.20 (2 H, m), 2.82 (1 H, dt, J = 16.79, 6.64 Hz), 2.64 (1 H, dt, J = 16.80, 5.75 Hz), 2.46-2.37 (1 H, m), 2.32-2.16 (2 H, m), 2.16-2.07 (1 H, m), 1.97-1.86 (2 H, m). No NH$_2$ peak observed. (off-white solid) |

$^{a\text{-}f}$Rt refers to HPLC method A to F

Example 63

In Vitro Assays

Biochemical Assay to Assess Compounds for Inhibition of BACE-1

The LanthaScreen™ BACE1 assay kit from Invitrogen (Catalogue number PV4748) was used as the primary assay in the screening cascade.

The assay principle is such that a fluorescently labelled biotinylated substrate exhibits FRET in the presence of a Terbium labelled anti-biotin antibody. In the presence of active BACE1 enzyme, the FRET signal decreases as a result of substrate cleavage and this can be inhibited by a β-secretase inhibitor IV (Calbiochem 565788) with an IC$_{50}$ of 15-30 nM. Compounds capable of inhibiting BACE-1 protease activity are therefore associated with high FRET values.

The assay was performed in a 384-well microplate according to the manufacturer's instructions using an enzyme concentration of 700 mU/ml, equivalent to 20 nM (BACE1 EC$_{50}$ was 0.106 U/ml) and a substrate concentration of 200 nM. As the program progressed the enzyme concentration was reduced to 10 nM to reflect the improved potency of the test compounds. Briefly, the test compound was incubated with the enzyme and substrate for 1 hour at room temperature in a reaction volume of 15 μl and then 5 nM terbium labelled anti-biotin antibody was added to stop the reaction and the solution incubated for a further 1 hour at room temperature. The microplate was read on an Envision plate reader fitted with a photometric 340 nm excitation filter and the amount of substrate that had been cleaved was represented by the TR-FRET ratio, calculated by dividing the Fluorescein emission signal (520 nm) by the Terbium emission signal (495 nm).

Cell Based Assay to Assess Compounds for Inhibition of BACE-1

The cell based assay used to support the program utilized HTRF assay reagents from Cisbio (Catalogue number 62B40PEB) to quantify the amount of Aβ1-40 peptide secreted by recombinant HEK293 cells. The cells were engineered to produce high quantities of APP, the precursor for Aβ1-40 peptide, under hygromycin selection pressure. Briefly, cells were plated into 384-well microplates and allowed to settle for 2 hours prior to compound addition. Following overnight treatment with compound, the media containing secreted peptide was transferred into a low volume assay plate for quantification with HTRF immunoassay reagents. Adhering to the manufacturers protocol for quantification, a TR-FRET signal is obtained in the presence of the Aβ1-40 peptide following addition of a cryptate conjugated antibody and an XL665 conjugated antibody, each raised to a different epitope of the Aβ1-40 peptide. A low FRET signal is obtained when cells are treated with compounds that inhibit APP cleavage and peptide secretion.

The concentration of Aβ1-40 peptide secreted by 30,000 cells in an assay well was approximately 7500 pg/ml and the secretion was inhibited by treatment with a γ-secretase inhibitor (Calbiochem 565789) with an IC$_{50}$ of 200 pM.

Inhibition of secretion resulting from compound toxicity was assessed using the CellTiter-Glo® luminescent cell viability assay from Promega (Catalogue number G7570). By quantitating the ATP generated by metabolically active cells, it is possible to confirm that active compounds were not exerting their effect by inducing cell death.

Results are given in the following table I:

| Ex | Compound | Enzymatic assay IC50 Ranges | Cellular assay EC50 Ranges |
|---|---|---|---|
| 1 | | b | a |
| 2 | | a | a |
| 3 | | c | c |
| 4 | | c | c |
| 5 | | c | c |
| 6 | | c | c |
| 7 | | c | c |

-continued

| Ex | Compound | Enzymatic assay IC50 Ranges | Cellular assay EC50 Ranges |
|---|---|---|---|
| 8 | | c | c |
| 9 | | c | b |
| 10 | | b | a |
| 11 | | c | b |
| 12 | | c | b |
| 13 | | c | c |
| 14 | | b | b |

-continued

| Ex | Compound | Enzymatic assay IC50 Ranges | Cellular assay EC50 Ranges |
|---|---|---|---|
| 15 | | b | a |
| 16 | | b | a |
| 17 | | b | b |
| 18 | | c | b |
| 19 | | c | b |
| 20 | | c | b |
| 21 | | b | c |

-continued
| Ex | Compound | Enzymatic assay IC50 Ranges | Cellular assay EC50 Ranges |
|---|---|---|---|
| 22 | 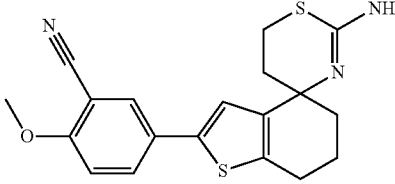 | c | b |
| 23 | 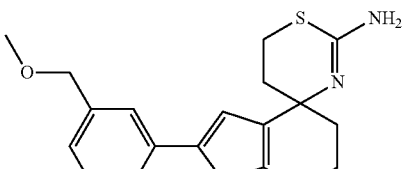 | c | b |
| 24 | 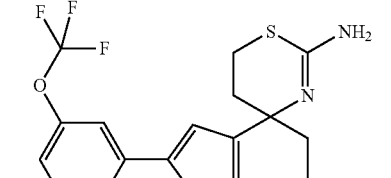 | b | c |
| 25 | 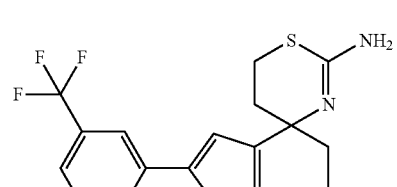 | b | c |
| 26 | 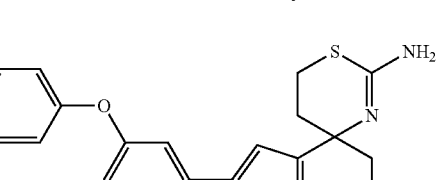 | b | c |
| 27 | 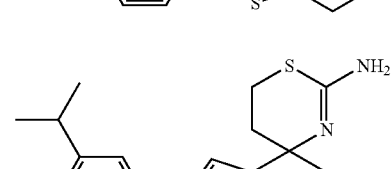 | b | c |
| 28 | 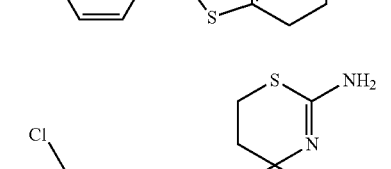 | b | c |

-continued
| Ex | Compound | Enzymatic assay IC50 Ranges | Cellular assay EC50 Ranges |
|---|---|---|---|
| 29 | 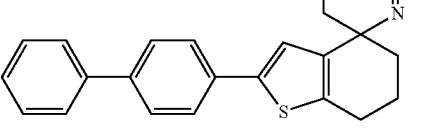 | b | c |
| 30 |  | b | c |
| 31 | 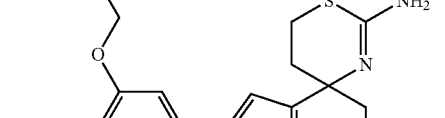 | b | b |
| 32 | 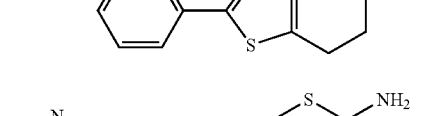 | b | c |
| 33 | 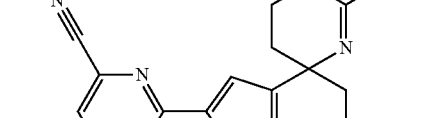 | b | c |
| 34 | 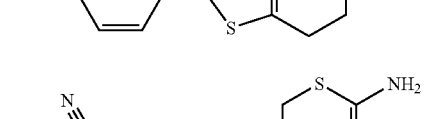 | b | b |

| Ex | Compound | Enzymatic assay IC50 Ranges | Cellular assay EC50 Ranges |
|---|---|---|---|
| 35 | | b | b |
| 36 | | c | c |
| 37 | | c | c |
| 38 | | b | c |
| 39 | | c | c |
| 40 | | c | c |
| 41 | | b | c |

-continued

| Ex | Compound | Enzymatic assay IC50 Ranges | Cellular assay EC50 Ranges |
|---|---|---|---|
| 42 | | b | c |
| 43 | | c | c |
| 44 | | b | c |
| 45 | | c | b |
| 46 | | c | c |
| 47 | | c | b |

-continued

| Ex | Compound | Enzymatic assay IC50 Ranges | Cellular assay EC50 Ranges |
|---|---|---|---|
| 48 | | b | c |
| 49 | | a | a |
| 50 | | c | b |
| 51 | | a | a |
| 52 | | c | b |
| 53 | | b | c |
| 54 | | a | b |

-continued

| Ex | Compound | Enzymatic assay IC50 Ranges | Cellular assay EC50 Ranges |
|---|---|---|---|
| 55 | | b | b |
| 56 | | b | b |
| 57 | | a | c |
| 58 | | b | c |
| 59 | | b | c |

| Ex | Compound | Enzymatic assay IC50 Ranges | Cellular assay EC50 Ranges |
|---|---|---|---|
| 60 | | a | c |
| 61 | | b | c |
| 62 | | c | c |

Enzymatic assay IC50 Ranges
a: IC50 ≤ 1 uM
b: 1 uM < IC50 ≤ 5 uM
c: 5 uM < IC50 ≤ 65 uM
Cellular assay EC50 Ranges
a: EC50 ≤ 1 uM
b: 1 uM < EC50 ≤ 5 uM
c: 5 uM < EC50 ≤ 50 uM

Example 64

Preparation of a Pharmaceutical Formulation

Formulation 1—Tablets

A compound of formula (I) is admixed as a dry powder with a dry gelatin binder in an approximate 1:2 weight ratio. A minor amount of magnesium stearate is added as a lubricant. The mixture is formed into 240-270 mg tablets (80-90 mg of active compound according to the invention per tablet) in a tablet press.

Formulation 2—Capsules

A compound of formula (I) is admixed as a dry powder with a starch diluent in an approximate 1:1 weight ratio. The mixture is filled into 250 mg capsules (125 mg of active compound according to the invention per capsule).

Formulation 3—Liquid

A compound of formula (I) (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A compound of formula (I) is admixed as a dry powder with a dry gelatin binder in an approximate 1:2 weight ratio. A minor amount of magnesium stearate is added as a lubricant. The mixture is formed into 450-900 mg tablets (150-300 mg of active compound according to the invention) in a tablet press.

Formulation 5—Injection

A compound of formula (I) is dissolved in a buffered sterile saline injectable aqueous medium to a concentration of approximately 5 mg/mL.

The invention claimed is:

1. A compound of Formula (I)

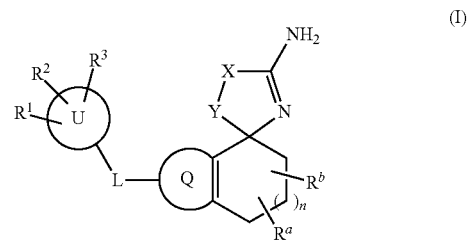

(I)

wherein

X denotes a group selected from —S—CH$_2$—, and —SO—CH$_2$—, while Y denotes a —CH$_2$— group, Q denotes a thiophene ring, L denotes a bond or —NR$^5$—CO—, U denotes a phenyl, pyridine, or pyrimidine group, R$^1$, R$^2$, R$^3$ are each independently selected from H, CN, halogen, Ar, Het, A, OA, SO$_2$A, CO$_2$A, and O(CH$_2$)Ar, or 2 of R$^1$, R$^2$ and R$^3$ are linked together to form a 5 to 8 membered ring fused to the ring U and optionally containing 1 to 3 heteroatoms independently selected from O, N or S, R$^a$ R$^b$ are each independently H, A, Ar, (CH$_2$)Ar, or (CH$_2$)Het, each R$^5$ is independently selected from H, A, and (CH$_2$)—Ar, each A is independently a linear or branched alkyl having 1 to 6 carbon atoms wherein 1 to 6 hydrogen atoms may be independently replaced by a group selected from halogen, —OC$_1$-C$_6$-alkyl, and CN, each Ar is independently a 6-membered aromatic ring which may be substituted with 1 to 3 groups selected from A, OA, phenyl, pyridine, CN, OH, and CO$_2$A, Het is a 4- to 8-membered heterocyclic ring containing 1 to 3 heteroatoms independently selected from O, S, N and CO, and optionally substituted with 1 to 3 groups selected from A, OA, phenyl, pyridine, CN, OH, and CO$_2$A, n is 0, 1 or 2, as well as enantiomers, diastereoisomers, tautomers thereof in all ratios, and salts thereof.

2. The compound according to claim 1, of Formula (I-1):

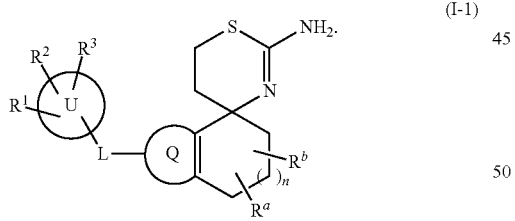
(I-1)

3. The compound of claim 1, wherein the group

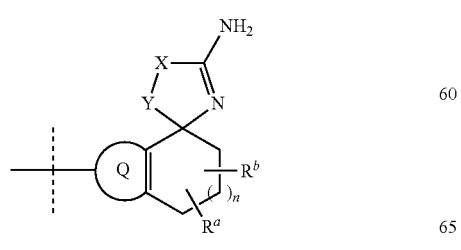

denotes one the following groups:

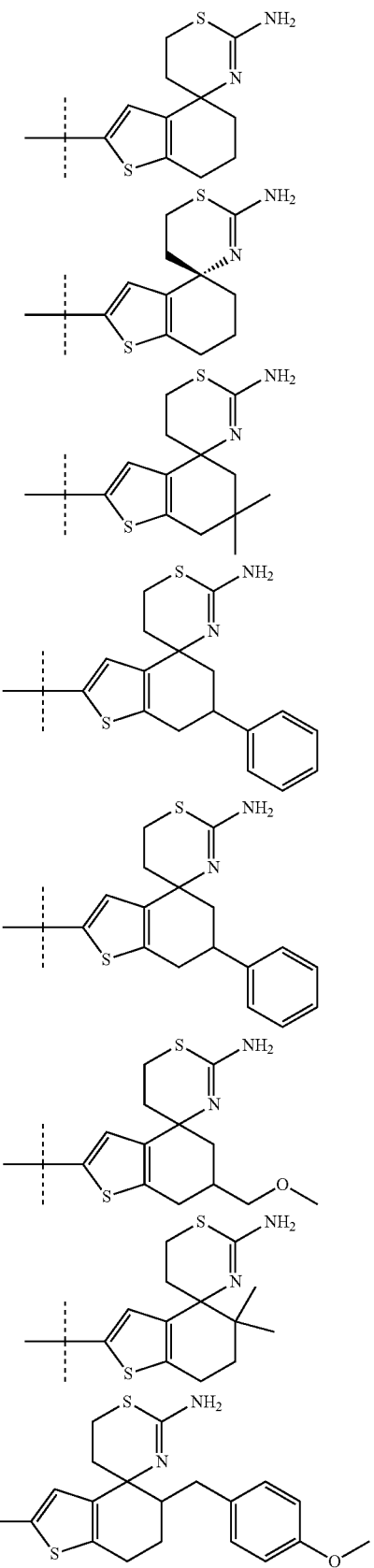

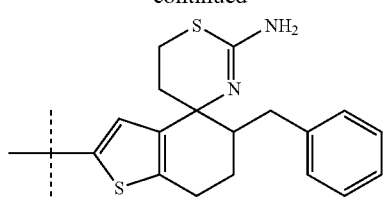
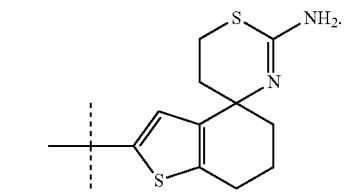
4. The compound of claim 1 wherein the group
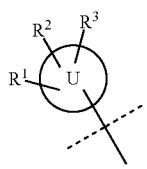
denotes one of the following groups:
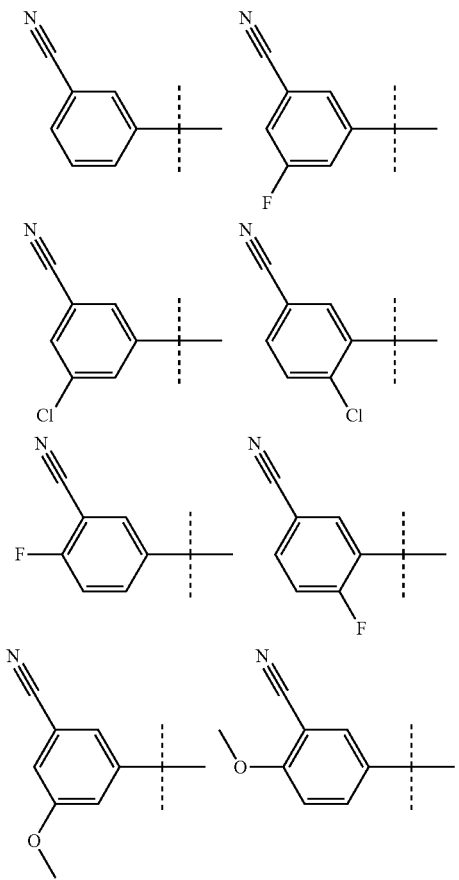
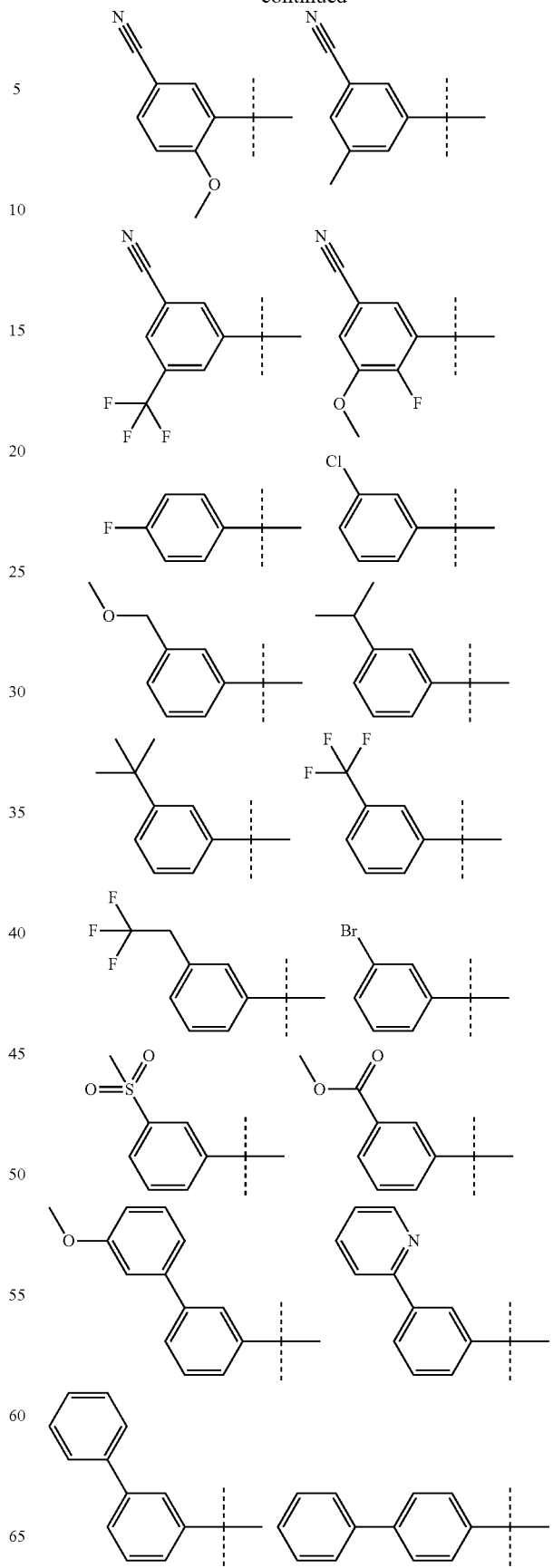

-continued
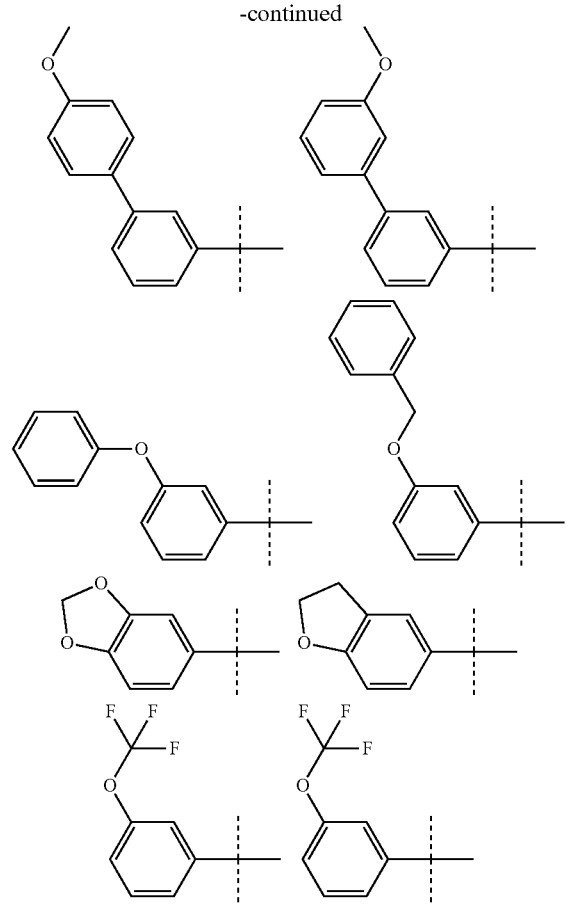
-continued
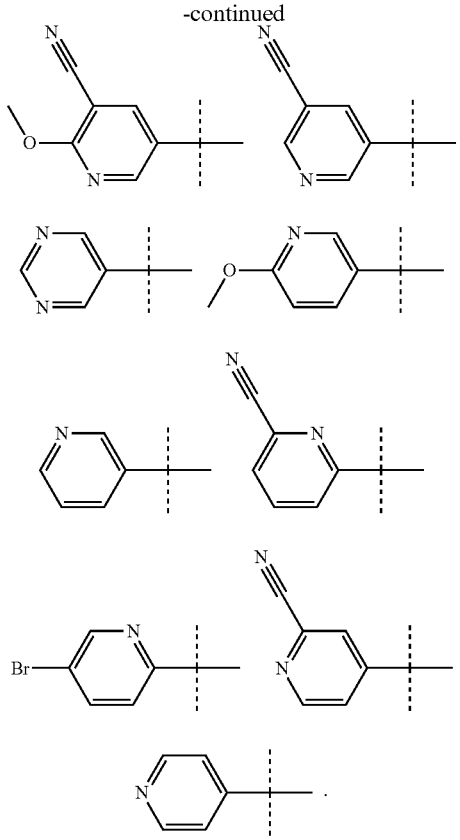
5. The compound of claim 1 wherein the compound is selected from:

-continued

| Ex | Compound | Ex | Compound |
|---|---|---|---|
| 7 | | 8 | |
| 9 | | 10 | |
| 11 | | 12 | |
| 13 | | 14 | |
| 15 | | 16 | |
| 17 | | 18 | |

-continued

| Ex | Compound | Ex | Compound |
|---|---|---|---|
| 19 | | 20 | |
| 21 | | 22 | |
| 23 | | 24 | |
| 25 | | 26 | |
| 27 | | 28 | |
| 29 | | 30 | |
| 31 | | 32 | |

-continued

| Ex | Compound | Ex | Compound |
|----|----------|----|----------|
| 33 | | 34 | |
| 35 | | 36 | |
| 37 | | 38 | |
| 39 | | 40 | |
| 41 | | 42 | |
| 43 | | 44 | |

| Ex | Compound | Ex | Compound |
|---|---|---|---|
| 45 | | 46 | |
| 47 | | 48 | |

6. A pharmaceutical composition comprising at least one compound of claim 1 and/or pharmaceutically usable derivatives, tautomers, salts, solvates and stereoisomers thereof, including mixtures thereof in all ratios, and optionally excipients and/or adjuvants.

7. A pharmaceutical composition comprising at least one compound of claim 1 and/or pharmaceutically usable derivatives, tautomers, salts, solvates and stereoisomers thereof, including mixtures thereof in all ratios, and at least one further active ingredient.

8. A kit consisting of separate packs of
  (a) an effective amount of a compound of claim 1 and/or pharmaceutically usable derivatives, tautomers, salts, solvates and stereoisomers thereof, including mixtures thereof in all ratios,
  and
  (b) an effective amount of a further medicament active ingredient.

9. A process to manufacture a compound of claim 1, wherein L is a single bond, comprising the step of reacting a compound of Formula (XX)

(XX)

wherein Q, X, Y, $R^a$, $R^b$, and n are as defined in claim 1, and wherein T is selected from halogen, nitro, carboxy, boronic acid or boronate ester, with boronate derivative

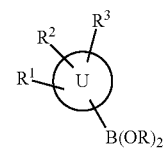

wherein U, $R^1$, $R^2$ and $R^3$ are as defined in claim 1, and wherein R is an alkyl group or hydrogen;
to produce the compound of formula (I) in claim 1.

10. The compound according to claim 1, of Formula (A):

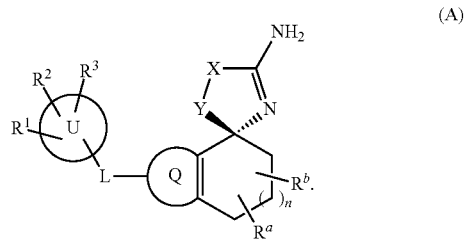

(A)

11. The compound according to claim 1, of Formula (B):

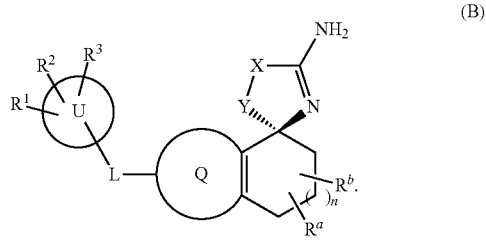

(B)

* * * * *